(12) United States Patent
Reilly et al.

(10) Patent No.: US 7,655,783 B2
(45) Date of Patent: *Feb. 2, 2010

(54) METHODS AND COMPOSITIONS FOR INCREASING ANTIBODY PRODUCTION

(75) Inventors: Dorothea Reilly, San Francisco, CA (US); Daniel Yansura, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 11/438,487

(22) Filed: May 22, 2006

(65) Prior Publication Data

US 2007/0128111 A1    Jun. 7, 2007

Related U.S. Application Data

(63) Continuation of application No. 10/697,995, filed on Oct. 30, 2003.

(60) Provisional application No. 60/422,952, filed on Oct. 31, 2002.

(51) Int. Cl.
*C07H 21/04* (2006.01)
*C12N 5/10* (2006.01)
*C12P 21/08* (2006.01)

(52) U.S. Cl. ............ 536/23.53; 435/328; 435/70.21

(58) Field of Classification Search ............... None
See application file for complete search history.

(56) References Cited

U.S. PATENT DOCUMENTS

| | | | |
|---|---|---|---|
| 4,816,567 A | 3/1989 | Cabilly et al. |
| 5,264,365 A | 11/1993 | Georgiou et al. |
| 5,264,586 A | 11/1993 | Nicolaou et al. |
| 5,348,876 A | 9/1994 | Michaelsen et al. |
| 5,500,362 A | 3/1996 | Robinson et al. |
| 5,508,192 A | 4/1996 | Georgiou et al. |
| 5,585,097 A | 12/1996 | Bolt et al. |
| 5,624,821 A | 4/1997 | Winter et al. |
| 5,639,635 A | 6/1997 | Joly et al. |
| 5,648,237 A | 7/1997 | Carter |
| 5,648,260 A | 7/1997 | Winter et al. |
| 5,677,425 A | 10/1997 | Bodmer et al. |
| 5,731,168 A | 3/1998 | Carter et al. |
| 5,807,706 A | 9/1998 | Carter et al. |
| 5,821,333 A | 10/1998 | Carter et al. |
| 5,821,337 A | 10/1998 | Carter et al. |
| 5,840,523 A | 11/1998 | Simmons et al. |
| 5,854,027 A | 12/1998 | Steipe et al. |
| 5,892,019 A | 4/1999 | Schlom et al. |
| 6,027,888 A | 2/2000 | Georgiou et al. |
| 6,083,715 A | 7/2000 | Georgiou et al. |
| 6,165,745 A | 12/2000 | Ward et al. |
| 6,331,415 B1 | 12/2001 | Cabilly et al. |
| 6,455,279 B1 | 9/2002 | Ambrosius et al. |
| 6,602,688 B1 | 8/2003 | Opper et al. |
| 2003/0118592 A1 | 6/2003 | Ledbetter et al. |
| 2005/0048572 A1* | 3/2005 | Reilly et al. .......... 435/7.1 |
| 2005/0152894 A1 | 7/2005 | Krummen et al. |
| 2005/0170464 A1* | 8/2005 | Simmons et al. ....... 435/69.1 |

FOREIGN PATENT DOCUMENTS

| | | |
|---|---|---|
| WO | WO 89/01974 | 3/1989 |
| WO | WO 92/22583 | 12/1992 |
| WO | WO 94/29531 | 12/1994 |
| WO | WO 95/14779 | 6/1995 |
| WO | WO 99/25378 | 5/1999 |
| WO | WO 99/51642 | 10/1999 |
| WO | WO 99/64460 | 12/1999 |
| WO | WO 02/056910 | 7/2002 |
| WO | WO 02/061090 | 8/2002 |
| WO | WO 03/074569 | 9/2003 |
| WO | WO 2004/042017 A2 | 5/2004 |
| WO | WO 2005/027966 A2 | 3/2005 |

OTHER PUBLICATIONS

Aruffo et al., "CD44 is the Principal Cell Surface Receptor for Hyaluronate" Cell 61:1303-1313 (Jun. 29, 1990).
Ashkenazi et al., "Immunoadhesins" Intern. Rev. Immunol. 10:219-227 (1993).
Ashkenazi et al., "Protection Against Endotoxic Shock by a Tumor Necrosis Factor Receptor Immunoadhesin" Proc. Natl. Acad. Sci. 88:10535-10539 (Dec. 1991).
Atwell et al., "Stable heterodimers from remodeling the domain interface of a homodimer using a phage display library" J.Mol.Biol. 270(1):26-35 (1997).
Bennett et al., "Extracellular Domain-IgG Fusion Proteins for Three Human Natriuretic Peptide Receptors. Hormone Pharmacology and Application to Solid Phase Screening of Synthetic Peptide Antisera" The Journal of Biological Chemistry 266(34):23060-23067 (1991).
Berg et al., "Bispecific Antibodies that Mediate Killing of Cells Infected with Human Immunodeficiency Virus of Any Strain" Proc. Natl. Acad. Sci. USA 88:4723-4727 (Jun. 1991).
Brekke O H et al., "The structural requirements for complement activation by IgG: does it hinge on the hinge?" Immunol Today 16(2):85-90 (Feb. 1995).
Brennan et al., "Preparation of bispecific antibodies by chemical recombination of monoclonal immunoglobulin G\sub I \nor fragments" Science 229:81-83 (Jul. 5, 1985).
Byrn et al., "Biological Properties of a CD4 Immunoadhesin" Nature 344:667-670 (Apr. 12, 1990).

(Continued)

*Primary Examiner*—Ilia Ouspenski
(74) *Attorney, Agent, or Firm*—Morrison & Foerster LLP

(57) ABSTRACT

The invention provides methods and compositions for improved expression and production of recombinant antibodies in host cell expression systems. In particular, prokaryotic expression and production of antibodies with modified hinge cysteine residues are provided. The invention further provides compositions, kits and articles of manufacture for practicing methods of the present invention.

26 Claims, 34 Drawing Sheets

OTHER PUBLICATIONS

Canevari et al., "Regression of advanced ovarian carcinoma by intraperitoneal treatment with autologous T lymphocytes retargeted by a bispecific monoclonal antibody" J Natl Cancer Inst. 87(19):1463-1469 (Oct. 4, 1995).
Capon et al., "Designing CD4 Immunoadhesins for AIDS Therapy" Nature 337:525-531 (Feb. 9, 1989).
Carpenter et al., "Non-Fc Receptor-Binding Humanized Anti-CD3 Antiibodies Induce Apoptosis of Activated T Cells" J. Immunol. 165:6205-6213 (2000).
Carter, "Bispecific human IgG by design" J Immunol Methods 248(1-2):7-15 (Feb. 1, 2001).
Chalupny et al., "T-cell activation molecule 4-1 BB binds to extracellular matrix proteins" Proc. Natl. Acad. Sci. USA 89(21):10360-10364 (Nov. 1992).
Cunningham and Wells, "High-Resolution Epitope Mapping of hGH-Receptor Interactions by Alanine-Scanning Mutagenesis" Science 244:1081-1085 (Jun. 2, 1989).
Davis, A. et al., "Intermolecular disulfide bonding in IgM: effects of replacing cysteine residues in the μ heavy chain", *The EMBO Journal*, 8(9):2519-2526 (1989).
Dietsch et al., "Bispecific Receptor Globulins, Novel Tools for the Study of Cellular Interactions" Journal of Immunological Methods 162:123-132 (1993).
Duncan et al., "Localization of the Binding Site for the Human High-Affinity Fc Receptor on IgG." Nature 332:563-564 (Apr. 7, 1988).
Ellman et al., "Biosynthetic Method for Introducing Unnatural Amino Acids Site-Specifically into Proteins" Meth. Enzym. 202:301-336 (1991).
Fanger et al., "Bispecific Antibodies" Critical Reviews in Immunology 12(3,4):101-124 (1992).
Gascoigne et al, "Secretion of a chimeric T-cell receptor-immunoglobulin protein" Proc Natl Acad Sci U S A. 84(9):2936-2940 (May 1987).
Gazzano-Santoro et al., "A Non-Radioactive Complement-Dependent Cytotoxicity Assay for Anti-CD20 Monoclonal Antibody" Journal of Immunological Methods. 202(2):163-171 (Mar. 28, 1997).
Gillies et al., "Antigen Binding and Biological Activities of Engineered Mutant Chimeric Antibodies with Human Tumor Specificities" Hum. Antibod. Hybridomas 1(1):47-54 (1990).
Gruber et al., "Efficient Tumor Cell Lysis Mediated by a Bispecific Single Chain Antibody Expressed in *Escherichia coli*" Journal of Immunology 152:5368-5374 (1994).
Hammerling et al., "Use of hybrid antibody with anti-\147G and anti-ferritin specificities in locating cell surface antigens by electron microscopy" Journal of Experimental Medicine 128:1461-1469 (1968).
Harris, "Production of humanized monoclonal antibodies for in vivo imaging and therapy" Biochemical Society Transactions 23:1035-1038 (1995).
Hayden et al., "Antibody engineering" Curr Opin Immunol. 9(2):201-212 (Apr. 1997).
Hollinger et al., ""Diabodies": Small Bivalent and Bispecific Antibody Fragments" Proc. Natl. Acad. Sci. USA 90:6444-6448 (Jul. 1993).
Hsieh-Ma et al., "In vitro cytotoxic targeting by human mononuclear cells and bispecific antibody 2B1, recognizing c-erbB-2 protooncogene product and Fc gamma receptor III" Cancer Research 52(24):6832-6839 (Dec. 15, 1992).
Hsu et al., "A Humanized Anti-CD3 Antibody,HuM291, With Low Mitogenic Activity, Mediates Complete And Reversible T-Cell Depletion in chimpanzees" Transplantation 68(4):545-554 (1999).
Hurle and Gross, "Protein Engineering Techniques for Antibody Humanization" Curr. Op. Biotech. 5:428-433 (1994).
Idusogie et al., "Mapping of the C1q Binding Site on Rituxan, A Chimeric Antibody with a Human IgGI Fc" J. Immunol. 164(8):4178-4184 (2000).
Jefferis et al., "Glycosylation of antibody molecules: structural and functional significance" Chem. Immunol. 65:111-128 (1997).
Jefferis et al., "IgG-Fc-mediated effector functions: molecular definition of interaction sites for effector ligands and the role of glycosylation" Immunol Rev. 163:59-76 (1998).
Jefferis et al., "Interaction sites on human IgG-Fc for FcgammaR: current models" Immunol. Lett. 82(1-2):57-65 (2002).
Karpovsky et al., "Production of target-specific effector cells using hetero-cross-linked aggregates containing anti-target cell and anti-Fc gamma receptor antibodies" J Exp Med. 160(6):1686-1701 (Dec. 1, 1984).
Klein et al., "Expression of biological effector functions by immunoglobulin G molecules lacking the hinge region" Proc. Natl. Acad. Sci. USA 78(1):524-528 (Jan. 1981).
Kon et al., "Randomised, dose-ranging, placebo-controlled study of chimeric Antibody to CD4 (keliximab) in Chronic Severe Asthma" Lancet 352:1109-1113(1998).
Kostelny et al., "Formation of a Bispecific Antibody by the Use of Leucine Zippers" Journal of Immunology 148(5):1547-1553 (Mar. 1, 1992).
Kroesen et al., "Local antitumour treatment in carcinoma patients with bispecific-monoclonal-antibody-redirected T cells" Cancer Immunol Immunother. 37(6):400-407 (Nov. 1993).
Kroesen et al., "Phase I study of intravenously applied bispecific antibody in renal cell cancer patients receiving subcutaneous interleukin 2" Br J Cancer 70(4):652-661 (Oct. 1994).
Kufer et al., "A revival of bispecific antibodies" Trends Biotechnol. 22(5):238-244 (May 2004).
Kurschner et al., "Construction, purification, and characterization of new interferon γ(IFNγ) inhibitor proteins. Three IFNγ receptor-immunoglobulin hybrid molecules" Journal of Biological Chemistry 267(13):9354-9360 (1992).
Le Doussal et al., "Bispecific Monoclonal Antibody-Mediated Targeting of an Indium-I I I-Labeled DTPA Dimer to Primary Colorectal Tumors: Pharmacokinetics, Biodistribution, Scintigraphy and Immune Response" J. Nucl. Med. 34:1662-1671 (1993).
Le Doussal et al., "Bispecific-Antibody-Mediated Targeting of Radiolabeled Bivalent Haptens: Theoretical, Experimental and Clinical Results" Int. J. Cancer Suppl. 7:58-62 (1992).
Lesslauer et al., "Recombinant Soluble Tumor Necrosis Factor Receptor Proteins Protect Mice From Lipopolysaccharide-induced Lethality" European Journal of Immunology 21:2883-2886 (1991).
Linsley et al., "Binding of the B cell activation antigen B7 to CD28 costimulates T cell proliferation and interleukin 2 mRNA accumulation" J Exp Med. 173(3):721-730 (Mar. 1, 1991).
Linsley et al., "CTLA-4 is a second receptor for the B cell activation antigen B7" J Exp Med. 174(3):561-569 (Sep. 1, 1991).
Lisowska, "The role of glycosylation in protein antigenic properties" Cell. Mol. Life Sci. 59(3):445-455 (2002).
Michaelsen T E et al., "One disulfide bond in front of the second heavy chain constant region is necessary and sufficient for effector functions of human IgG3 without a genetic hinge" Proc Natl Acad Sci U S A. 91(20):9243-9247 (Sep. 27, 1994).
Milstein and Cuello, "Hybrid Hybridomas and Their Use in Immunohistochemistry" Nature 305:537-540 (Oct. 6, 1983).
Mimura et al., "The molecular specificity of IgG-Fc interactions with Fcgamma receptors" Adv. Exp. Med. Biol. 495:49-53 (2001).
Muller et al., "The first constant domain (C(H)1 and C(L)) of an antibody used as heterodimerization domain for bispecific miniantibodies" FEBS Letters 422(2):259-264 (Jan. 30, 1998).
Nolan et al., "Bifunctional antibodies: concept, production and applications" Biochimica et Biophysica Acta 1040:1-11 (1990).
Noren et al., "A general method for site-specific incorporation of unnatural amino acids into proteins" Science 244(4901):182-188 (Apr. 14, 1989).
Pack, P. et al., "Miniantibodies: Use of Amphipathic Helices to Produce Functional, Flexibly Linked Dimeric $F_v$ Fragments with igh Avidity in *Excherichia coli*", Biochemistry, 31(6):1579-1584 (Feb. 18, 1992).
Peipp & Valerius, "Bispecific antibodies targeting cancer cells" Biochem Soc Trans. 30(4):507-511 (Aug. 2002).
Peppel et al., "A Tumor Necrosis Factor (TNF) Receptor-IgG Heavy Chain Chimeric Protein as a Bivalent Antagonist of TNF Activity" Journal of Experimental Medicine 174:1483-1489 (Dec. 1991).

Perez et al., "Specific targeting of cytotoxic T cells by anti-T3 linked to anti-target cell antibody", Nature 316:354-256 (1985).
Ponder and Richards, "Tertiary templates for proteins. Use of packing criteria in the enumeration of allowed sequences for different structural classes" J Mol Biol. 193(4):775-791 (Feb. 20, 1987).
Presta, "Engineering antibodies for therapy" Current Pharmaceutical Biotechnology 3(3):237-256 (2002).
Radaev et al., "Recognition of immunoglobulins by Fcgamma receptors" Molecular Immunology 38(14):1073-1083 (2001).
Ridgway and Gorman, "Expression and Activity of IgE Receptor Alpha Chain-IgG Chimeric Molecules" Journal of Cell Biology 115:250a (Abstract No. 1448) (1991).
Rodrigues et al., "Engineering a humanized bispecific F(ab')\sub2\nor fragment for improved binding to T cells" Int. J. Cancer (Suppl.) 7:45-50 (1992).
Rudd et al., "Glycosylation and the Immune System" Science 291:2370-2376 (2001).
Segal et al., "Introduction: Bispecific Antibodies" J Immunol Methods 248(1-2):1-6 (Feb. 1, 2001).
Segal et al., "Targeting and Activation of Cytotoxic Lymphocytes" Chem. Immunol. 47:179-213 (1989).
Shalaby, et al., "Development of Humanized Bispecific Antibodies Reactive with Cytotoxic Lymphocytes and Tumor Cells Overexpressing the HER2 Protooncogene" Journal of Experimental Medicine 175:217-225 (Jan. 1992).
Songsivilai et al., "Bispecific antibody: a tool for diagnosis and treatment of disease" Clin. Exp. Immunol. 79:315-321(1990).
Stamenkovic et al., "The B Lymphocyte Adhesion Molecule CD22 Interacts with Leukocyte Common Antigen CD45RO on T Cells and \1412-6 Sialyltransferase, CD75, on B Cells" Cell 66:1133-1144 (Sep. 20, 1991).
Stickney et al., "Bifunctional Antibody: A Binary Radiopharmaceutical Delivery System for Imaging Colorectal Carcinoma" Cancer Research 51:6650-6655 (Dec. 15, 1991).
Talac & Nelson, "Current perspectives of bispecific antibody-based immunotherapy" J Biol Regul Homeost Agents 14(3):175-181 (Jul. 2000).
Traunecker et al., "Highly Efficient Neutralization of HIV with Recombinant CD4-immunoglobulin Molecules" Nature 339:68-70 (May 4, 1989).
Valone et al., "Phase Ia/Ib trial of bispecific antibody MDX-210 in patients with advanced breast or ovarian cancer that overexpresses the proto-oncogene HER-2/neu" J Clin Oncol. 13(9):2281-2292 (Sep. 1995).
Van der Lubbe et al., "Chimeric CD4 monoclonal antibody cM-T412 as a therapeutic approach to rheumatoid arthritis" Arthritis and Rheumatism 36(10):1375-1379 (1993).
van Spriel et al, "Immunotherapeutic perspective for bispecific antibodies" Immunol Today 21(8):391-397 (Aug. 2000).
Vaswani and Hamilton, "Humanized Antibodies as Potential Therapeutic Drugs" Ann. Allergy, Asthma & Immunol. 81:105-119 (Aug. 1998).
Watson et al., "A Homing Receptor-IgG Chimera as a Probe for Adhesive Ligands of Lymph Node High Endothelial Venules" Journal of Cell Biology 110:2221-2229(1990).
Watson et al., "Neutrophil Influx into an Inflammatory Site Inhibited by a Soluble Homing Receptor-IgG Chimaera" Nature 349:164-167 (Jan. 10, 1991).
Weiner et al., "A Human Tumor Xenograft Model of Therapy with a Bispecific Monoclonal Antibody Targeting c-erbB-2 and CD16" Cancer Research 53:94-100 (Jan. 1, 1993).
Weiner et al., "Phase I trial of 2B1, a bispecific monoclonal antibody targeting c-erbB-2 and Fc gamma RIII" Cancer Research 55(20):4586-4593 (Oct. 15, 1995).
Wright and Morrison, "Effect of Glycosylation on Antibody Function: Implications for Genetic Engineering" Trends in Biotechnology 15:26-32 (1997).
Xu et al., "In vitro characterization of five humanized OKT3 effector function variant antibodies" Cellular Immunology 200(1):16-26 (2000).
Zettlmeissl et al., "Expression and Characterization of Human CD4: Immunoglobulin Fusion Proteins" DNA and Cell Biology 9(5):347-353 (1990).

International Search Report dated May 27, 2004.
Adlersberg, Ric Clin Lab (1976) 6(3):191-205.
Aric et al., Molecular Microbiology (2001) 39(1):199-210.
Armour et al., Eur. J. Immunol. (1999) 29:2613-2624.
Barbas et al., PNAS USA (1994) 91:3809-3813.
Bloom et al., Protein Science (1997) 6:407-415.
Bothmann et al., J Biol Chem (2000) 275(22):17100-17105.
Brekke et al., Nature (1993) 363:628-630.
Capel et al., Immunomethods (1994) 4:25-34.
Carter et al., Bio/Technology (1992) 10:163-167.
Carter et al., PNAS USA (1992) 89:4285-4289.
Chamow et al., J. Immunol. (1994) 153:4268-4280.
Chang et al., Gene (1987) 55:189-196.
Chen et al., J. Biol. Chem. (1999) 274(28):19601-19605.
Chen et al., J. Mol. Biol. (1999) 293:865-881.
Chothia et al., J. Mol. Biol. (1987) 196:901-917.
Clynes et al., PNAS USA (1998) 95:652-656.
Daeron et al., Annu. Rev. Immunol. (1997) 15:203-234.
De Haas et al., J. Lab. Clin. Med. (1995) 126:330-341.
Duncan et al., Nature (1988) 332:738-740.
Friend et al., Transplantation (1999) 68:1632-1637.
Guyer et al., J. Immunol. (1976) 117:587-593.
Hara et al., Microbial Drug Resistance (1996) 2(1):63-72.
Hawkins et al., J. Mol. Biol. (1992) 226:889-896.
Humphreys et al., J. Immunol. Methods (1997) 209:193-202.
Isaacs et al., Clin. Exp. Immunol. (1996) 106:427-433.
Jackson et al., J. Immunol. (1995) 154(7):3310-3319.
Joly et al., PNAS USA (1998) 95:2773-2777.
Jones et al., Nature (1986) 321:522-525.
Kelley et al., Biochemistry (1995) 34:10383-10392.
Kikuchi et al., Nucleic Acids Res. (1981) 9:5671-5678.
Kim et al., J. Immunol. (1994) 24:2429-2434.
Kim et al., Mol. Immunol. (1995) 32(7):467-475.
Kipriyanov et al., Mol. Biotech (1999) 12:173-201.
Kurokawa et al., Journal of Biological Chemistry (2001) 276(17):14393-14399.
Lee et al., Infect. Immun. (1983) 42(1):264-268.
Marks et al., Bio/Technology (1992) 10:779-783.
Merchant et al., Nat. Biotech. (1998) 16:677-681.
Missiakas et al., Journal of Bacteriology (1997) 179(8):2465-2471.
Morrison et al., PNAS USA (1984) 81(21):6851-6855.
Peters et al., PNAS USA (1993) 90:8915-8919.
Picken et al., Infect. Immun. (1983) 42(1):269-275.
Pluckthun et al., "Producing antibodies in *Escherichia coli*: from PCR to fermentation," in: Antibody Engineering: A Practical Approach, Oxford Press, Chapter 10, 1996, pp. 203-252.
Pluckthun et al., Immunotech (1997) 3:83-105.
Pluckthun et al., Pharmacol of Monoclonal Antibodies, Handbook of Exp Pharmacology (1994) 3:269-315.
Presta, Curr Op Struct Biol (1992) 2:593-596.
Presta et al., Cancer Research (1997) 57:4593-4599.
Presta et al., J. Immunol. (1993) 151(5):2623-2632.
Presta et al., Thromb Haemost (2001) 85:379-389.
Proba et al., Gene (1995) 159:203-207.
Ramm et al., J. Mol. Biol. (2000) 275(22):17106-17113.
Ravetch et al., Annu. Rev. Immunol. (1991) 9:457-492.
Reddy et al., J Immunol (2000) 164:1925-1933.
Riechmann et al., Nature (1988) 332:323-327.
Schier et al., Gene (1995) 169:147-155.
Scholtissek et al., Nucleic Acids Res. (1987) 15:3185.
Shields et al., Biol. Chem. (2001) 276:6591-6604.
Siebenlist et al., Cell (1980) 20:269-281.
Simmons et al., J. Immunol. Methods (2002) 263:133-147.
Simmons et al., Nature Biotechnology (1996) 14:629-634.
Sims et al., J. Immunol. (1993) 151:2296-2308.
Sutcliffe, DNA: Replication and Recombination, Cold Spring Harbor Symposia on Quantitative Biology, Cold Spring Harbor Laboratory (1979) XLIII:77-90.
Thompson et al., J. Immunol. Meth (1999) 227:17-29.
Verhoeyen et al., Science (1988) 239:1534-1536.
Yanofsky et al., Nucleic Acids Res (1981) 9:6647-6668.
Yansura et al., Methods: A companion to Methods in Enzymology (1992) 4:151-158.

Yelton et al., J. Immunol. (1995) 155:1994-2004.

Eccles, "Monoclonal antibodies targeting cancer: 'magic bullets' or just the trigger?", *Breast Cancer Research*, 3:86-90 (2001).

Reff et al., "A review of modifications to recombinant antibodies: attempt to increase efficacy in oncology applications", *Critical Reviews in Oncology/Hematology*, 40:25-35 (2001).

Tutt et al., "Monoclonal Antibody Therapy of B Cell Lymphoma; Signaling Activity on Tumor Cells Appears More Important Than Recruitment of Effectors", *The Journal of Immunology*, 161:3176-3185 (1998).

Yoshida et al., "Ganglioside $G_{D2}$ in Small Cell Lung Cancer Cell Lines: Enhancement of Cell Proliferation and Mediation of Apoptosis", *Cancer Research*, 61:4244-4252 (2001).

International Search Report mailed Jun. 14, 2006.

Bird and Walker, Trends in Biotechnol (1991) 9(4):132-137.

Glockshuber et al., Biochemistry (1990) 29:1362-1367.

Knappik et al., Bio/Technology (1993) 11:77-83.

Leung et al., Clin Cancer Res (1999) 5(10):3106S-3117S.

Ryabova et al., Nature Biotechnology (1997) 15:79-84.

Shuurman et al., Molec Immunol (2001) 38:1-8.

Supplementary European Search Report for EP 03781577.6, mailed May 7, 2009, 6 pages.

Wu et al., Protein Engineering (2001) 14(12):1025-1033.

Zhang et al., J Biotechnol (2002) 18(3):261-266.

* cited by examiner

```
2501  TGCCAAGACA AAGCCGCGGG AGGAGCAGTA CAACAGCACG TACCGTGTGG TCAGCGTCCT CACCGTCCTG CACCAGGACT GGCTGAATGG CAAGGAGTAC
      ACGGTTCTGT TTCGGCGCCC TCCTCGTCAT GTTGTCGTGC ATGGCACACC AGTCGCAGGA GTGGCAGGAC GTGGTCCTGA CCGACTTACC GTTCCTCATG
310    A  K  T   K  P  R  E   E  Q  Y    N  S  T   Y  R  V  V   S  V  L    T  V  L    H  Q  D  W    L  N  G    K  E  Y

2601  AAGTGCAAGG TCTCCAACAA AGCCCTCCCA GCCCCCATCG AGAAAACCAT CTCCAAAGCC AAAGGGCAGC CCGAGAACTAC ACAGTGTAC ACCCTGCCCC
      TTCAGTTCC AGAGGTTGTT TCGGGAGGGT CGGGGGTAGC TCTTTTGGTA GAGGTTTCGG TTTCCCGTCG GGCTCTTGG TGTCCACATG TGGGACGGGG
343    K  C  K  V    S  N  K   A  L  P    A  P  I  E    K  T  I    S  K  A    K  G  Q  P    R  E  P    Q  V  Y    T  L  P  P

2701  CATCCCGGGA AGAGATGACC TCAGCCTGAC CTGCCTGGTC AAAGGCTTCT ATCCCAGCGA CATCGCCGTG GAGTGGGAGA GCAATGGGCA
      GTAGGGCCCT TCTCTACTGG AGTCGGACTG GACGGACCAG TTTCCGAAGA TAGGGTCGCT GTAGCGGCAC CTCACCCTCT CGTTACCCGT
377    S  R  E    E  M  T    S  L  T     C  L  V     K  G  F  Y    P  S  D    I  A  V     E  W  E  S    N  G  Q

2801  GCCGGAGAAC AACTACAAGA CCACGCCTCC CGTGCTGGAC TCCGACGGCT CCTTCTTCCT CTACAGCAAG CTCACCGTGG ACAAGAGCAG GTGGCAGCAG
      CGGCCTCTTG TTGATGTTCT GGTGCGGAGG GCACGACCTG AGGCTGCCGA GGAAGAAGGA GATGTCGTTC GAGTGGCACC TGTTCTCGTC CACCGTCGTC
410    P  E  N    N  Y  K  T    T  P  P    V  L  D     S  D  G  S    F  F  L     Y  S  K    L  T  V  D    K  S  R     W  Q  Q

2901  GGGAACGTCT TCTCATGCTC CGTGATGCAT GAGGCTCTGC ACAACCACTA CACGCAGAAG AGCCTCTCCC TGTCTCCGGG TAAATAAGCA TGCGACGGCC
      CCCTTGCAGA AGAGTACGAG GCACTACGTA CTCCGAGACG TGTTGGTGAT GTGCGTCTTC TCGGAGAGGG ACAGAGGCCC ATTTATTCGT ACGCTGCCGG
443    G  N  V  F    S  C  S     V  M  H    E  A  L  H    N  H  Y    T  Q  K    S  L  S  L    S  P  G     K  Q

3001  CTAGAGTCCC TAACGCTCGG ATTGGCGAGC GGGTTTTTA TTGTTAACTC ATGTTTGACA GCTTATCATC GATAAGCTTT AATGCGGTAG TTTATCACAG
      GATCTCAGGG ATTGCGAGCC TAACCGCTCG CCCAAAAAAT AACAATTGAG TACAAACTGT CGAATAGTAG CTATTCGAAA TTACGCCATC AAATAGTGTC
                                                "Start Tet Resistance Coding Sequence"

3101  TTAAATTGCT AACGCAGTCA GGCACCGTGT ATGAAATCTA ACAATGCGCT CATCGTCATC CTCGGCACCG TCACCCTGGA TGCTGTAGGC ATAGGCTTGG
      AATTTAACGA TTGCGTCAGT CCGTGGCACA TACTTTAGAT TGTTACGCGA GTAGCAGTAG GAGCCGTGGC AGTGGGACCT ACGACATCCG TATCCGAACC

3201  TTATGCCGGT ACTGCCGGGC CTCTTGCGGG ATATCGTCCA TTCCGACAGC ATCGCCAGTC ACTATGCGGT GCTGCTAGCG CTATATGCGT TGATGCAATT
      AATACGGCCA TGACGGCCCG GAGAACGCCC TATAGCAGGT AAGGCTGTCG TAGCGGTCAG TGATACCGCA CGACGATCGC GATATACGCA ACTACGTTAA

```
 901 TGAATAACTT CTATCCAGAG GAGGCCAAAG TACAGTGGAA GGTGGATAAC GCCCTCCAAT CGGGTAACTC CCAGGAGAGT GTCACAGAGC AGGACAGCAA
     ACTTATTGAA GATAGGTCTC CTCCGGTTTC ATGTCACCTT CCACCTATTG CGGGAGGTTA GCCCATTGAG GGTCCTCTCA CAGTGTCTCG TCCTGTCGTT
 160  N  N  F   Y  P  R    E  A  K  V   Q  W  K    V  D  N    A  L  Q  S   G  N  S    Q  E  S    V  T  E  Q   D  S  K

1001 GGACAGCACC TACAGCCTCA GCAGCACCCT GACGCTGAGC AAAGCAGACT ACGAGAAACA CAAAGTCTAC GCCTGCGAAG TCACCCATCA GGGCCTGAGC
     CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
 193  D  S  T   Y  S  L  S    S  T    L  T  L  S   K  A  D  Y   E  K  H    K  V  Y   A  C  E  V    T  H  Q    G  L  S

1101 TCGCCCGTCA CAAAGAGCTT CAACAGGGGA GAGTGTTAAT TAAATCTCTC TAAATCCTCT ACGCCGGACG CATCGTGGCG AGCTCGGTAC CCGGGGATCT AGGCCTAACG
     AGCGGGCAGT GTTTCTCGAA GTTGTCCCCT CTCACAATTA ATTTAGAGAG ATTTAGGAGA TGCGGCCTGC GTAGCACCGC TCGAGCCATG GGCCCCTAGA TCCGGATTGC
 226  S  P  V   T  K  S  F   N  R  G    E  C  Q

1201 CTCGGTTGCC GCCGGGCGTT TTTTATTGTT GCCGACGCGC ATCTCGAATG AACTGTGTGC GCAGGTAGAA GCTTTGGAGA TTATCGTCAC TGCAATGCTT
     GAGCCAACGG CGGCCCGCAA AAAATAACAA CGGCTGCGCG TAGAGCTTAC TTGACACACG CGTCCATCTT CGAAACCTCT AATAGCAGTG ACGTTACGAA

1301 CGCAATATGG TTGATTGATC AGTAGAGGG CCAACAGCGG ATCCTCGAAGCATTCC TGAAGCATCC TCGTCAGTAA GAGGTAAAGC CATTCCTGAC GACGATACGG
     GCGTTATACC ACTAACTAG TCCATCTCCC GGTTGTCGCC TAGGAGCTTC ACTTCGTAGG AGCAGTCATT CTCCATTTCG GTAAGGACTG CTGCTATGCC

1401 AGCTGCTGCG CGATTACGTA AAGAAGTTAT TGAAGCATCC TCGTCAGTAA ACTTCGTAGG TTTCAACAG GTTGTCACGG CCGAGACTTA
     TCGACGACGC GCTAATGCAT TTCTTCAATA ACTTCGTAGG AGCAGTCATT TGAAGCATT CAACAGTGCC GGCTCTGAAT

1501 TAGTCGCTTT GTTTTTATT TTTAATGTAT TTGTAACTAG TACGCAAGTT CACGTAAAAA GGGTATCTAG AATTATGAAG AAAAACATCG CTTTTCTTCT
     ATCAGCGAAA CAAAAATAA AAATTACATA AACATTGATC ATGCGTTCAA GTGCATTTT CCCATAGATC TTAATACTTC TTTTTGTAGC GAAAAGAAGA
   1                                                                                 M  K  K  N  I  A   F  L  L
                                                                                    ^start STII signal TIR-2

1601 TGCATCTATG TTCGTTTTTT CTATTGCTAC AAACGCGGTAC AAACGCGGTAC GCTGAGGTTC AGCTGGTGGA GTCTGGCGGT GGCCTGGTGC AGCCAGGGGG CTCACTCCGT
     ACGTAGATAC AAGCAAAAAA GATAACGATG TTTGCCCATG CGACTCCAAG CGACTCCAAG TCGACCACCT CAGACCGCCA CCGGACCACG TCGGTCCCCC GAGTGAGGCA
  10  A  S  M    F  V  F  F   S  I  A  T   N  A  Y   A  E  V  Q    L  V  E    S  G  G    G  L  V  Q    P  G  G    S  L  R
                                          ^start heavy chain
```

FIG. 2B

```
1701 TTGTCCTCTG CAGCTTCTGG CTTCAATATT AAGGAGTACT ACATGCACTG GGTCCGTCAG GCCCGGGTA AGGGCCTGGA ATGGGTTGGA TTGATTGATC
     AACAGGAGAC GTCGAAGACC GAAGTTATAA TTCCTCATGA TGTACGTGAC CCAGGCAGTC CGGGCCCCAT TCCCGGACCT TACCCAACCT AACTAACTAG
 43   L  S  C   A  A  S   G  F  N   I  K  E   Y  Y  M   H  W  V   R  Q  A   P  G  K   G  L  E   W  V  G   L  I  D  P

1801 CAGAGCAAGG CAACACGATC TATGACCCGA AGTTCCAGGA CCGTGCCACT ATAAGGCTG ACAATTCCAA AAACACAGCA TACCTGCAGA TGAACAGCCT
     GTCTCGTTCC GTTGTGCTAG ATACTGGGCT TCAAGGTCCT GGCACGGTGA TATTCGGAC TGTTAAGGTT TTTGTGTCGT ATGGACGTCT ACTTGTCGGA
 77   E  Q  G   N  T  I   Y  D  P   K  F  Q   D  R  A   T  I  S   A  D  N   S  K  N   T  A  Y   L  Q  M   N  S  L

1901 GCGTGCTGAG GACACTGCCG TCTATTATTG TGCTCGAGAC ACGGCCGCTT ACTTCGACTA CTGGGGTCAA GGAACCCTGG TCACCGTCTC CTCGGCCTCC
     CGCACGACTC CTGTGACGGC AGATAATAAC ACGAGCTCTG TGCCGGCGAA TGAAGCTGAT GACCCCAGTT CCTTGGGACC AGTGGCAGAG GAGCCGGAGG
110   R  A  E   D  T  A   V  Y  Y   C  A  R   D  T  A   A  Y  F   D  Y  W   G  Q  G   T  L  V   T  V  S   S  A  S

2001 ACCAAGGGCC CATCGGTCTT CCCCCTGGCA CCCTCCTCCA AGAGCACCTC TGGGGGCACA GCGGCCCTGG GCTGCCTGGT CAAGGACTAC TTCCCCGAAC
     TGGTTCCCGG GTAGCCAGAA GGGGGACCGT GGGAGGAGGT TCTCGTGGAG ACCCCCGTGT CGCCGGGACC CGACGGACCA GTTCCTGATG AAGGGGCTTG
143   T  K  G   P  S  V   F  P  L   A  P  S   S  K  S   T  S  G   G  T  A   A  L  G   C  L  V   K  D  Y   F  P  E  P

2101 CGGTGACGGT GTCGTGGAAC TCAGGCGCCC TGACCAGCGG CGTGCACACC TTCCCGGCTG TCCTACAGTC CTCAGGACTC TACTCCCTCA GCAGCGTGGT
     GCCACTGCCA CAGCACCTTG AGTCCGCGGG ACTGGTCGCC GCACGTGTGG AAGGCCGAC AGGATGTCAG GAGTCCTGAG ATGAGGGAGT CGTCGCACCA
177   V  T  V   S  W  N   S  G  A   L  T  S   G  V  H   T  F  P   A  V  L   Q  S  S   G  L  Y   S  L  S   S  V  V

2201 GACCGTGCCC TCTAGCAGCT TGGGCACCCA GACCTACATC TGCAACGTGA ATCACAAGCC CAGCAACACC AAGGTGGACA AGAAAGTTGA GCCCAAATCT
     CTGACACGGG AGATCGTCGA ACCCGTGGGT CTGGATGTAG AGTTGCACT TAGTGTTCGG GTCGTTGTGG TTCCACCTGT TCTTTCAACT CGGGTTTAGA
210   T  V  P   S  S  S   L  G  T   Q  T  Y   I  C  N   V  N  H   K  P  S   N  T  K   V  D  K   K  V  E   P  K  S

2301 TGTGACAAAA CTCACACATG CCCACCGTGC CCAGCACCTG AACTCCTGGG GGGACCGTCA GTCTTCCTCT TCCCCCCAAA ACCCAAGGAC ACCCTCATGA
     ACACTGTTTT GAGTGTGTAC GGGTGGCACG GGTCGTGGAC TTGAGGACCC CCCTGGCAGT CAGAAGGAGA AGGGGGGTTT TGGGTTCCTG TGGGAGTACT
243   C  D  K   T  H  T   C  P  P   C  P  A   P  E  L   L  G  G   P  S  V   F  L  F   P  P  K   P  K  D   T  L  M  I

2401 TCTCCCGGAC CCCTGAGGTC ACATGCGTGG TGGTGGACGT GAGCCACGAA GACCCTGAGG TCAAGTTCAA CTGGTACGTG GACGGCGTGG AGGTGCATAA
     AGAGGGCCTG GGGACTCCAG TGTACGCACC ACCACCTGCA CTCGGTGCTT CTGGGACTCC AGTTCAAGTT GACCATGCAC CTGCCGCACC TCCACGTATT
277   S  R  T   P  E  V   T  C  V   V  V  D   V  S  H   E  D  P   E  V  K   F  N  W   Y  V  D   G  V  E   V  H  N
```

FIG. 2C

```
2501  TGCCAAGACA AAGCCGCGGG AGGAGCAGTA CAACAGCACG TACCGTGTGG TCAGCGTCCT CACCGTCCTG CACCAGAGACT GGCTGAATGG CAAGGAGTAC
      ACGGTTCTGT TTCGGCGCCC TCCTCGTCAT GTTGTCGTGC ATGGCACACC AGTCGCAGGA GTGGCAGGAC GTGGTCCTGA CCGACTTACC GTTCCTCATG
310    A  K  T   K  P  R  E   E  Q  Y     N  S  T    Y  R  V  V    S  V  L     T  V  L     H  Q  D  W    L  N  G    K  E  Y

2601  AAGTGCAAGG TCTCCAACAA AGCCCTCCCA GCCCCCATCG AGAAAACCAT CTCCAAAGCC AGAAGGCAGC CCCGAGAACC ACAGGTGTAC ACCCTGCCCC
      TTCACGTTCC AGAGGTTGTT TCGGGAGGGT CGGGGGTAGC TCTTTTGGTA GAGGTTTCGG TCTTCCGTCG GGGCTCTTGG TGTCCACATG TGGGACGGGG
343    K  C  K  V   S  N  K     A  L  P    A  P  I  E    K  T  I    S  K  A     K  G  Q  P    R  E  P    Q  V  Y     T  L  P  P

2701  CATCCCGGGA AGAGATGACC TCAGCCTGAC CTGCCTGGTC AAAGGCTTCT ATCCCAGCGA CATCGCCGTG GAGTGGGAGA GCAATGGGCA
      GTAGGGCCCT TCTCTACTGG AGTCGGACTG GACGGACCAG TTTCCGAAGA TAGGGTCGCT GTAGCGGCAC CTCACCCTCT CGTTACCCGT
377    S  R  E   E  M  T     L  S  L  T    C  L  V     K  G  F  Y    P  S  D    I  A  V     E  W  E  S    N  G  Q

2801  GCCGGAGAAC AACTACAAGA CCACGCCTCC CGTGCTGGAC TCCGACGGCT CCTTCTTCCT CTACAGCAAG CTCACCGTGG ACAAGAGCAG GTGGCAGCAG
      CGGCCTCTTG TTGATGTTCT GGTGCGGAGG GCACGACCTG AGGCTGCCGA GGAAGAAGGA GATGTCGTTC GAGTGGCACC TGTTCTCGTC CACCGTCGTC
410    P  E  N   N  Y  K  T    P  P      V  L  D    S  D  G  S     F  F  L     Y  S  K     L  T  V  D     K  S  R     W  Q  Q

2901  GGGAACGTCT TCTCATGCTC CGTGATGCAT GAGGCTCTGC ACAACCACTA CACGCAGAAG AGCCTCTCCC TGTCTCCGGG TAAATAAGCA TGGACGGCC
      CCCTTGCAGA AGAGTACGAG GCACTACGTA CTCCGAGACG TGTTGGTGAT GTGCGTCTTC TCGGAGAGG ACAGAGGCCC ATTTATTCGT ACGCTGCCGG
443    G  N  V  F   S  C  S     V  M  H    E  A  L  H    N  H  Y     T  Q  K     S  L  S  L    S  P  G    K  *

3001  CTAGAGTCCC TAACGCTCGG TTGCCGCCGG GCGTTTTTTA TTGTTAACTC ATGTTTGACA GCTTATCATC GATAAGCTTT AATGCGGGTAG TTTATCACAG
      GATCTCAGGG ATTGCGAGCC AACGGCGGCC CGCAAAAAAT AACAATTGAG TACAAACTGT CGAATAGTAG CTATTCGAAA TTACGCCATC AAATAGTGTC

3101  TTAAATTGCT AACGCAGTCA GGCACCGTGT ATGAAATCTA ACAATGCGCT CATCGTCATC CTCGGCACCG TCACCCTGGA TGCTGTAGGC ATAGGCTTGG
      AATTTAACGA TTGCGTCAGT CCGTGGCACA TACTTTAGAT TGTTACGCGA GTAGCAGTAG GAGCCGTGGC AGTGGGACCT ACGACATCCG TATCCGAACC

3201  TTATGCCGGT ACTGCCGGGC CTCTTGCGGG ATATCGTCCA TT
      AATACGGCCA TGACGGCCCG GAGAACGCCC TATAGCAGGT AA
```

```
2501 CGGCGTGGAG GTGCATAATG CCAAGACAAA GCCGCGGGAG GAGCAGTACA ACAGCACGTA CCGTGTGGTC AGCGTCCTCA CCGTCCTGCA CCAAGACTGG
     GCCGCACCTC CACGTATTAC GGTTCTGTTT CGGCGCCCTC CTCGTCATGT TGTCGTGCAT GGCACACCAG TCGCAGGAGT GGCAGGACGT GGTCCTGACC
310  G  V  E   V  H  N  A   K  T  K    P  R  E    E  Q  Y  N   S  T  Y    R  V  V    S  V  L  T   V  L  H    Q  D  W

2601 CTGAATGGCA AGGAGTACAA GTGCAAGGTC TCCAACAAAG CCCTCCCAGC TCCAACAGGT AAAACCATCT CCAAAGCCAA AGGGCAGCCC CGAGAACCAC
     GACTTACCGT TCCTCATGTT CACGTTCCAG AGGTTGTTTC GGGAGGGTCG AGGTTGTCCA TTTTGGTAGA GGTTTCGGTT TCCCGTCGGG GCTCTTGGTG
343  L  N  G   K  E  Y  K   C  K  V    S  N  K  A   L  P  A    P  I  E    K  T  I  S   K  A  K    G  Q  P    R  E  P  Q

2701 AGGTGTACAC CCTGCCCCCA TCCCGGGAAG AGATGACCAA GAACCAGGTC AGCCTGACCT GCCTGGTCAA AGGCTTCTAT CCCAGCGACA TCGCCGTGGA
     TCCACATGTG GGACGGGGGT AGGGCCCTTC TCTACTGGTT CTTGGTCCAG TCGGACTGGA CGGACCAGTT TCCGAAGATA GGGTCGCTGT AGCGGCACCT
377  V  Y  T   L  P  P  P   S  R  E  E   M  T  K    N  Q  V    S  L  T  C   L  V  K    G  F  Y    P  S  D  I   A  V  E

2801 GTGGGAGAGC AATGGGCAGC CGGAGAACAA CTACAAGACC ACGCCTCCCG TGCTGGACTC CGACGGCTCC TTCTTCCTCT ACAGCAAGCT CACCGTGGAC
     CACCCTCTCG TTACCCGTCG GCCTCTTGTT GATGTTCTGG TGCGGAGGGC ACGACCTGAG GCTGCCGAGG AAGAAGGAGA TGTCGTTCGA GTGGCACCTG
410  W  E  S   N  G  Q  P   E  N  N    Y  K  T    T  P  P  V   L  D  S    D  G  S    F  F  L  Y   S  K  L    T  V  D

2901 AAGAGCAGGT GGCAGCAGGG GAACGTCTTC TCATGCTCCG TGATGCATGA GGCTCTGCAC AACCACTACA CGCAGAAGAG CCTCTCCCTG TCTCCGGGTA
     TTCTCGTCCA CCGTCGTCCC CTTGCAGAAG AGTACGAGGC ACTACGTACT CCGAGACGTG TTGGTGATGT GCGTCTTCTC GGAGAGGGAC AGAGGCCCAT
443  K  S  R  W   Q  Q  G   N  V  F    S  C  S  V   M  H  E    A  L  H    N  H  Y  T   Q  K  S    L  S  L    S  P  G  K

3001 AATAAGCATG CGACGGCCCT AGAGTCCCTA ACGGTCGGTT GCCGCGGGGC GTTTTTATT GTTAACTCAT GTTTGACAGC TTATCATCGA TAAGCTTTAA
     TTATTCGTAC GCTGCCGGGA TCTCAGGGAT TGCCAGCCAA CGGCGCCCCG CAAAAATAA CAATTGAGTA CAAACTGTCG AATAGTAGCT ATTCGAAATT
477  O

3101 TGCGGTAGTT TATCACAGTT AAATTGCTAA CGCCAGTCAG CACCGTGTAT GAAATCTAAC CTTTAGATTG TTACGGCGAGT TGTCATCCT CGGCACCGTC ACCCTGGATG
     ACGGCCATCA ATAGTGTCAA TTTAACGATT GCGGTCAGTC GTGGCACATA CTTTAGATTG AATCTAAC AATGCGCTCA AGCAGTAGGA GCCGTGGCAG TGGGACCTAC
                                                                                                          "Start Tet Resistance Coding Sequence 3201 CTGTAGGCAT AGGCTTGGTT ATGCCGGTAC TGCCCGGCCT CTTGCGGGAT ATCGTCCATT CCGACAGCAT CGGCAGTCAC TATGGCGTGC TGCTAGCGCT
     GACATCCGTA TCCGAACCAA TACGGCCATG ACGGGCCGGA GAACGCCCTA TAGCAGGTAA GGCTGTCGTA GCCGTCAGTG ATACCGCACG ACGATCGCGA

```
  1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
    CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA AGCTTGGAG ATTATCGTCA CTGCAATGCT TCGCAATATG GCGCAAAATG ACCAACAGCG GTTGATTGAT CAGGTAGAGG
    CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

201 GGGCGCTGTA CGAGTAAAG CCCGATGCCA GCATTCCTGA CGACGATACG GAGCTGCTGC GCGATTACGT AAAGAAGTTA TTGAAGCATC CTCGTCAGTA
    CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCACG AGTTGTCACG GCCGAGACTT ATAGTGCTT TGTTTTTATT TCTATTGCTA TTTGTAACTA GTACGCAAGT
    TTTTCAATTA GAAAAGTTGT CGACAGTATT TCAACAGTGC CGGCTCTGAA TATCAGCGAA ACAAAATAA AGATAACGAT AAACATTGAT CATGCGTTCA

401 TCACGTAAAA AGGGTATCTA GAATTATGAA GAAGAATATC GCATTTTCTC TTGCATTTAT GTTCGTTTTT TCTATTGCTA CAAACGCCTA CGCTGATATC
    AGTGCATTTT TCCCATAGAT CTTAATACTT CTTCTTATAG CGTAAAGAG AACGTAAATA CAAGCAAAAA AGATAACGAT GTTTGCGCAT GCGACTATAG

1                                      M K K N I A F L L A S M F V F S I A T N A Y A D I
                                         ↑STII signal TIR -1                              ↑Light chain 501 CAGTTGACCC AGTCCCCGAG CTCCCTGTCC GCCTCTGTGG GCGATAGGGT CACCATCACC TGCAGGCCAA GTCAGGATAT TAGCAACTAT TTAAACTGGT
    GTCAACTGGG TCAGGGGCTC GAGGGACAGG CGGAGACACC CGCTATCCCA GTGGTAGTGG ACGTCCGGTT CAGTCCTATA ATCGTTGATA AATTTGACCA

26  Q L T Q S P S S L S A S V G D R V T I T C S A S Q D I S N Y L N W Y

601 ATCAACAGAA ACCAGGAAAA GCTCCGAAAG TACTGATTTA TTCGACTAAAT ATGACTAAAT GCCAGAAGAC CGGTCTTCTG AAGGTTGAA ACCTAGGC ACAGACCCTG
    TAGTTGTCTT TGGTCCTTTT CGAGGCTTTC ATGACTAAAT TAGCTGATTTA TACTGATTTA CGGTCTTCTG GCCAGAAGAC TTCCAATCCG TGTCTGGGAC CAAGACCCTG

60  Q Q K P G K A P K V L I Y S A S R F S G S G S G T

701 GGATTTCACT CTGACCATCA GCAGCCTGCA GCCAGAAGAC TTTGCAACTT ATTACTGTCA ACAGTATAGC ACCGTGCCGT GGACGTTCGG ACAGGGTACC
    CCTAAAGTGA GACTGGTAGT CGTCGGACGT CGGTCTTCTG AAGCGTTGAA TAATGACAGT TGTCATATCG TGGCACGGCA CCTGCAAGCC TGTCCCATGG

93  D F T L T I S S L Q P E D F A T Y Y C Q Q Y S T V P W T F G Q G T

801 AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
    TTCCACCTCT AGTTTGCTTG ACACCGACGT GGTAGACAGA AGTAGAAGGG CGGTAGACTA CTCGTCAACT TTAGACCTTG ACGAAGACAA CACACGGACG

```
 901  TGAATAACTT CTATCCCAGA GAGGCCAAAG TACAGTGGAA GGTTGGATAAC GCCCTCCAAT CGGGTAACTC CCAGGAGAGT GTCACAGAGC AGGACAGCAA
      ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
 160    N  N  F   Y  P  R    E  A  K  V    Q  W  K    V  D  N    A  L  Q  S    G  N  S    Q  E  S    V  T  E  Q    D  S  K

1001  GGACAGCACC TACAGCCTCA GCAGCCTGAG GACGCACCCT GCAGTGTACT ACAGAGAAACA GCCTGCGAAG TCACCCATCA GGGCCTGAGC
      CCTGTCGTGG ATGTCGGAGT CGTCGGACTC CTGCGTGGGA CGTCACATGA TGCTCTTTGT CGGACGCTTC AGTGGGTAGT CCCGGACTCG
 193    D  S  T   Y  S  L  S   S  L  S    T  L  T  L  S    K  A  D  Y   E  K  H    K  V  Y    A  C  E  V    T  H  Q    G  L  S

1101  TCGCCCGTCA CAAAGAGCTT CAACAGGGGA GAGTGTTAAT TAAATCCTCT ACGCGGACG AGCTCGGTAC CCGGGGATCT AGGCTAACG
      AGCGGGCAGT GTTTCTCGAA GTTGTCCCCT CTCACAATTA ATTTAGGAGA TGCGGCCTGC TCGAGCCATG GGCCCCTAGA TCCGATTGC
 226    S  P  V  T    K  S  F    N  R  G    E  C  O                                                    ^lambda t0 terminator^

1201  CTCGGTTGCC GCCGGGCCGT TTTTATTGTT GCCGACGCGC ATCTCGAATG AACTGTGTGC GCAGGTAGAA GCTTTGGAGA TTATCGTCAC TGCAATGCTT
      GAGCCAACGG CGGCCCGGCA AAAATAACAA CGGCTGCGCG TAGAGCTTAC TTGACACACG CGTCCATCTT CGAAACCTCT AATAGCAGTG ACGTTACGAA

1301  CGCAATATGG CGCAAAATGA CCAACAGCGG TTGATTGATC AGTAGAGGGG GGGCTGTAC GAGGTAAAGC CCGATGCCAG CATTCCTGAC GACGATACGG
      GCGTTATACC GCGTTTTACT GGTTGTCGCC AACTAACTAG TCCATCTCCC CCCGACATG GGCTACGGTC GTAAGGACTG CTGCTATGCC

1401  AGTCGCTGCG CGATTACGTA AAGAAGTTAT TGAAGCATCC TCGTCAGTAA AAGTTAATC TTTTCAACAG CTGTCATAAA GTTGTCACGG CCGAGACTTA
      TCGACGACGC GCTAATGCAT TTCTTCAATA ACTTCGTAGG AGCAGTCATT TTTCAATTAG AAAAGTTGTC GACAGTATTT CAACAGTGCC GGCTCTGAAT

1501  TAGTCGCTTT GTTTTATTT TTTAATGTAT TTGTAACTAG TACGCAAGTT CACGTAAAAA GGGTATCTAG AATTATGAAG AAGATATCG CATTTCTTCT
      ATCAGCGAAA CAAAAATAAA AAAATTACATA AACATTGATC ATGCGTTCAA GTGCATTTTT CCCATAGATC TTAATACTTC TTCTATAGC GTAAAGAAGA
                                                                                            1    M  K  N  I  A   F  L  L
                                                                                            ^STII Signal TIR-1^

1601  TGCATTCTAT TTCGTTTTTT CTATTGCTAC AAACGGGTAC GCTGAGGTTC AGCTGGTGGA GTCTGGCGGT GGCCTGGTGC AGCCAGGGGG CTCACTCCGT
      ACGTAAGATAC AAGCAAAAAA GATAACGATG TTTGCCCATG CGACTCCAAG TCGACCACCT CAGACCGCCA CCGGACCACG TCGGTCCCCC GAGTGAGGCA
  10    A  S  M   F  V  F  S   I  A  T    N  A  Y    A  E  V  Q    L  V  E    S  G  G   G  L  V  Q    P  G  G    S  L  R

FIG. 4B
```

```
1701  TTGTCCTGTG CAGCTTCTGG CTATACCTTC ACCAACTATG GTATAAACTG GGTCCGTCAG AGGGCCTGGA GCCCCGGGTA GCCCCGGTAA ATGGGTTGGA TGGATTAACA
      AACAGGACAC GTCGAAGACC GATATGGAAG TGGTTGATAC CATATTTGAC CCAGGCAGTC CGGGGCCCAT TCCCGGACCT TACCCAACCT ACCTAATTGT
 43    L  S  C  A  A  S  G  Y  T  F  T  N  Y  G  I  N  W  V  R  Q  A  P  G  K  G  L  E  W  V  G  W  I  N  T

1801  CCTATACCGG TGAACCGACC ACTTGGCTGG TGATGCGG ATTTCAAACG TGTTTCACT TTTTCTTTAG ACACCTCCAA AAGCACAGCA TACCTGACGA TGAACAGCCT
      GGATATGGCC ACTTGGCTGG TGATGCGG ATACGACGCC TAAAGTTTGC AGCAAAGTGA AAAAGAAATC TGTGGAGTT TTCGTGTCGT ATGGACGTCT ACTTGTCGGA
 77    Y  T  G  E  P  T  Y  A  A  D  F  K  R  R  F  T  F  S  L  D  T  S  K  S  T  A  Y  L  Q  M  N  S  L

1901  GCGCGCTGAG GACACTGCCG TCTATTACTG TGCAAAGTAC CCGCACTATT ATGTGAACGA GCGGAAGAGC CACTGGTATT TCGACGTCTG GGGTCAAGGA
      CGCGCGACTC CTGTGACGGC AGATAATGAC ACGTTTCATG GGCGTGATAA TACACTTGCT CGCCTTCTCG GTGACCATAA AGCTGCAGAC CCCAGTTCCT
110    R  A  E  D  T  A  V  Y  Y  C  A  K  Y  P  H  Y  Y  V  N  E  R  K  S  H  W  Y  F  D  V  W  G  Q  G

2001  ACCCTGGTCA CCGTCTCCTC GGCCTCCACC AAGGGCCCAT CGGTCTTCCC CCTGGCACCC TCCTCCAAGA GCACCTCTGG GGGCACAGCG GCCCTGGGCT
      TGGGACCAGT GGCAGAGGAG CCGGAGGTGG TTCCCGGGTA GCCAGAAGGG GGACCGTGGG AGGAGGTTCT CGTGGAGACC CCCGTGTCGC CGGGACCCGA
143    T  L  V  T  V  S  S  A  S  T  K  G  P  S  V  F  P  L  A  P  S  S  K  S  T  S  G  G  T  A  A  L  G  C

2101  GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC
      CGGACCAGTT CCTGATGAAG GGGCTTGGCC ACTGCCACAG CACCTTGAGT CCGCGGGACT GGTCGCCGCA CGTGTGGAAG GGCCGACAGG ATGTCAGGAG
177    L  V  K  D  Y  F  P  E  P  V  T  V  S  W  N  S  G  A  L  T  S  G  V  H  T  F  P  A  V  L  Q  S  S

2201  AGGACTCTAC TCCCTCAGCA GCGTGGTGAC CGTGCCCTCT AGCAGCTTGG GCACCCAGAC CTACATCTGC AACGTGAATC ACAAGCCCAG CAACACCAAG
      TCCTGAGATG AGGGAGTCGT CGCACCACTG GCACGGGAGA TCGTCGAACC CGTGGGTCTG GATGTAGACG TTGCAGTTAG TGTTGGGTTC GTTGTGGTTC
210    G  L  Y  S  L  S  S  V  V  T  V  P  S  S  S  L  G  T  Q  T  Y  I  C  N  V  N  H  K  P  S  N  T  K

2301  GTGGACAAGA AAGTTGAGCC CAAATCTTGT GACAAAACTC ACACATGCCC ACCGTGCCCA GCACCTGAAC TCCTGGGGGG ACCGTCAGTC TTCCTCTTCC
      CACCTGTTCT TTCAACTCGG GTTTAGAACA CTGTTTTGAG TGTGTACGGG TGGCACGGGT CGTGGACTTG AGGACCCCCC TGGCAGTCAG AAGGAGAAGG
243    V  D  K  K  V  E  P  K  S  C  D  K  T  H  T  C  P  P  C  P  A  P  E  L  L  G  G  P  S  V  F  L  F  P

2401  CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG
      GGGGTTTTGG GTTCCTGTGG GAGTACTAGA GGGCCTGGGG ACTCCAGTGT ACGCACCACC ACCTGCACTC GGTGCTTCTG GGACTCCAGT TCAAGTTGAC
277    P  K  P  K  D  T  L  M  I  S  R  T  P  E  V  T  C  V  V  V  D  V  S  H  E  D  P  E  V  K  F  N  W
```

*FIG. 4C*

```
2501  GTACGTGGAC GGCGTGGAGG TGCATAATGC CAAGACAAAG CGGCGGGAGG AGCAGTACAA CAGCACGTAC CGTGTGGTCA GGCTCCTGCAC CGTCCTGCAC
      CATGCACCTG CCGCACCTCC ACGTATTACG GTTCTGTTTC GCCGCCCTCC TCGTCATGTT GTCGTGCATG GCACACCAGT CCGAGGACTG GCAGGACGTG
310   Y  V  D  G  V  E  V  H  N  A  K  T  K  P  R  E  E  Q  Y  N  S  T  Y  R  V  V  S  V  L  T  V  L  H

2601  CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC
      GTCCTGACCG ACTTACCGTT CCTCATGTTC ACGTTCCAGA GGTTGTTTCG GGAGGGTCGG GGGTAGCTCT TTTGGTAGAG GTTTCGGTTT CCCGTCGGGG
343   Q  D  W  L  N  G  K  E  Y  K  C  K  V  S  N  K  A  L  P  A  P  I  E  K  T  I  S  K  A  K  G  Q  P  R

2701  GAGAACCACA GGTGTACACC CTGCCCCCAT CCCGGGAAGA GATGACCAAG AACCAGGTCA GCCTGACCTG CCTGGTCAAA GGCTTCTATC CCAGCGACAT
      CTCTTGGTGT CCACATGTGG GACGGGGGTA GGGCCCTTCT CTACTGGTTC TTGGTCCAGT CGGACTGGAC GGACCAGTTT CCGAAGATAG GGTCGCTGTA
377   E  P  Q  V  Y  T  L  P  P  S  R  E  E  M  T  K  N  Q  V  S  L  T  C  L  V  K  G  F  Y  P  S  D  I

2801  CGCCGTGGAG TGGGAGAGCA ATGGGCAGCC GGAGAACAAC TACAAGACCA CGCCTCCCGT GCTGGACTCC GATGGCTCCT TCTTCCTCTA CAGCAAGCTC
      GCGGCACCTC ACCCTCTCGT TACCCGTCGG CCTCTTGTTG ATGTTCTGGT GCGGAGGGCA CGACCTGAGG CTACCGAGGA AGAAGGAGAT GTCGTTCGAG
410   A  V  E  W  E  S  N  G  Q  P  E  N  N  Y  K  T  T  P  P  V  L  D  S  D  G  S  F  F  L  Y  S  K  L

2901  ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT
      TGGCACCTGT TCTCGTCCAC CGTCGTCCCC TTGCAGAAGA GTACGAGGCA CTACGTACTC CGAGACGTGT TGGTGATGTG CGTCTTCTCG GAGAGGGACA
443   T  V  D  K  S  R  W  Q  Q  G  N  V  F  S  C  S  V  M  H  E  A  L  H  N  H  Y  T  Q  K  S  L  S  L  S

3001  CTCCGGGTAA ATAAGCATGC GACGGCCCTA GAGTCCCTAA CGCTCGGTTG CCGCCGGGCG TTTTTTATTG TTAACTCATG TTTGACAGCT TATCATCGAT
      GAGGCCCATT TATTCGTACG CTGCCGGGAT CTCAGGGATT GCGAGCCAAC GGCGGCCCGC AAAAAATAAC AATTGAGTAC AAACTGTCGA ATAGTAGCTA
477   P  G  K  O                                         ^lambda terminator 3101  AAGCTTTAAT GGGTAGTTT ATCACAGTTA AATTGCTAAC GCAGTCAGGC ACCGTGTATG AAATCTAACA ATGGGCTCAT CGTCATCCTC GGCACCGTCA
      TTCGAAATTA CGCCATCAAA TAGTGTCAAT TTAACGATTG CGTCAGTCCG TGGCACATAC TTTAGATTGT TACCCGAGTA GCAGTAGGAG CCGTGGCAGT 3201  CCCTGGATGC TGTAGGCATA GGCTTGGTTA TGCCGGTACT GCCGGGCCTC TTGCG
      GGGACCTACG ACATCCGTAT CCGAACCAAT ACGGCCATGA CGGCCCGGAG AACGC
```

```
1001 CGGGTGTTCC GGGATCCCA CCGAATTCTA CCCTGGTGTT TGACGTAGAG CTGCTGGATG TGAAACCAGC GCCGAAGGCT GATGCAAAGC CGGAAGCTGA
     GCCCACAAGG CCCTAGGGT GGCTTAAGAT GGGACCACAA ACTGCATCTC GACGACCTAC ACTTTGGTCG CGGCTTCCGA CTACGTTTCG GCCTTCGACT
 229  G  V  P  G  I  P  P  N  S  T  L  V  F  D  V  E  L  L  D  V  K  P  A  P  K  A  D  A  K  P  E  A  D

1101 TGCGAAAGCC GCAGATTCTG CTAAAAAATA AAGCTAGC
     ACGCTTTCGG CGTCTAAGAC GATTTTTTAT TTCGATCG
 262  A  K  A  A  D  S  A  K  K  K  O     ^NheI
```

FIG. 5B

```
  1 GAATTCAACT TCTCCATACT TTGGATAAGG AAATACAGAC ATGAAAAATC TCAATTGCTA GTTGTTATTT AAGCTTGCCC AAAAAGAAGA AGAGTCGAAT
    CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA
    ^EcoRI

101 GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
    CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

201 GGGCGCTGTA CGAGGTAAAG CCCGATGCCA GCATTCCTGA CGACGATACG GAGTCGCTGC GCGATTACGT AAAGAGTTA TTGAAGCATC CTCGTCAGTA
    CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCATAA AGTTGTCACG GCCGAGACTT ATAGTCGCTT TGTTTTTATT TTTTAATGTA TTTGTAACTA GTACGCAAGT
    TTTTCAATTA GAAAAGTTGT CGACAGTATT TCAACAGTGC CGGCTCTGAA TATCAGCGAA ACAAAATAA AAAATTACAT AAACATTGAT CATGCGTTCA

401 TCACGTAAAA AGGTATCTA GAATTATGAA AAAGAATATC GCATTTCTTC TCTATTGCTA CAAACGCGTA CGCTGATATC
    AGTGCATTTT TCCCATAGAT CTTAATACTT TTTCTTATAG CGTAAAGAAG AGATAACGAT GTTTGCGCAT GCGACTATAG
      1                                 M   K   N   I   A   F   L   L   A   S   M   F   V   F   S   I   A   T   N   A   Y   A   D   I
                     ^start STII signal TIR 7                                                               anti-TF light chain^

501 CAGATGACCC AGTCCCCGAG CTCCCTGTCC GCCTCTGTGG GCGATAGGGT CACCATCACC TGCAGAGCCA GTCGCGACAT CAAGAGCTAT CTGAACTGGT
    GTCTACTGGG TCAGGGCTC GAGGGACAGG CGGAGACACC CGCTATCCCA GTGGTAGTGG ACGTCTCGGT CAGCGCTGTA GTTCTCGATA GACTTGACCA
26  Q   M   T   Q   S   P   S   S   L   S   A   S   V   G   D   R   V   T   I   T   C   R   A   S   R   D   I   K   S   Y   L   N   W   Y

601 ATCAACAGAA ACCAGGAAAA GCTCCGAAAG TACTGATTTA CTATGCTACT AGTCTCGCTG AAGGAGTCCC TTCTCGCTTC TCTGGATCCG GTTCTGGGAC
    TAGTTGTCTT TGGTCCTTTT CGAGGCTTTC ATGATAAAT GATACGATGA TCAGAGCGAC TTCCTCAGGG AAGAGGGAAG AGACTAGGCC CAAGACCCTG
60  Q   Q   K   P   G   K   A   P   K   V   L   I   Y   Y   A   T   S   L   A   E   G   V   P   S   R   F   S   G   S   G   S   G   T

701 GGATTACACT CTGACCATCA GCAGTCTGCA GCCAGAAGAC ATTGCTACTT ATTACTGTCT TAATGACAGA AGCGGTGTAA CCTGTAAACC TGTCCATGG
    CCTAATGTGA GACTGGTAGT CGTCAGACGT CGGTCTTCTG TAACGATGAA TAATGACAGA ATTACTGTCT TCGCCACATT GGACATTTGG ACAGGTACC
93  D   Y   T   L   T   I   S   S   L   Q   P   E   D   F   A   T   Y   Y   C   L   Q   H   G   E   S   P   W   T   F   G   Q   G   T

801 AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
    TTCCACCTCT AGTTTGCTTG ACACCGACGT GGTAGACAGA AGTAGAAGGG CGGTAGACTA CTCGTCAACT TTAGACCTTG ACGAAGACAA CACACGGACG
126 K   V   E   I   K   R   T   V   A   A   P   S   V   F   I   F   P   P   S   D   E   Q   L   K   S   G   T   A   S   V   V   C   L   L

901 TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
    ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
160 N   N   F   Y   P   R   E   A   K   V   Q   W   K   V   D   N   A   L   Q   S   G   N   S   Q   E   S   V   T   E   Q   D   S   K
```

```
  1 GAATTCAACT TCTCCATACT TTGGATAAGG AAATACAGAC ATGAAAAATC TCATTGCTGA GTTGTATATT AAGCTTGCCC AAAAAGAAGA AGAGTCGAAT
    CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CCAGGTAGA AGCTTTGGAG ATTATCGTCA CTGCAATGCT TCGCAATATG GCGCAAAATG ACCAACAGGG GTTGATTGAT CAGGTAGAGG
    CTTGACACAC GGTCCATCT TCGAAACCTC TAATAGCAGT GACGTTACGA AGCGTTATAC CGCGTTTTAC TGGTTGTCCC CAACTAACTA GTCCATCTCC

201 GGGCGCTGTA CGAGGTCTGA CCCGATGCCA GCATTCCTGA CGACGATACG GAGCTGCTGC GCGATTACGT AAAGAAGTTA TTGAAGCATC CTCGTCAGTA
    CCCGCGACAT GCTCCAGACT GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCATAA AGTTGTCACG GCCGAGACTT ATAGTCGGCT TGTTTTTATT TGTTTAACTA TTTGTAACTA GTACGCAAGT
    TTTTCAATTA GAAAAGTTGT CGACAGTATT TCAACAGTGC CGGCTCTGAA TATCAGCCGA ACAAAAATAA ACAATTTGAT AAACATTGAT CATGCGTTCA

401 TCACGTAAAA AGGGTATCTA GAATTATGAA AAAGAATATC GCATTTCTTC TTGCATCTAT GTTCGTTTTT TCTATTGCTA CAAACGGGTA CGCTGATATC
    AGTGCATTTT TCCCATAGAT CTTAATACTT TTTCTTATAG CGTAAGAAG AACGTAGATA CAAGCAAAAA AGATAACGAT GTTTGCGCAT GCGACTATAG
  1                             M  K  K  N  I  A  F  L  L  A  S  M  F  V  F  S  I  A  T  N  A  Y  A  D  I
                ^Start STII signal TIR 7                                                ^ anti-tissue factor light chain^

501 CAGATGACCC AGTCCCCGAG CTCCCTGTCC GCCTCTGTGG GCGATAGGGT CACCATCACC TGCAGAGCCA GTCAGAGTGT CTCGACCTAT CTGAACTGGT
    GTCTACTGGG TCAGGGGCTC GAGGGACAGG CGGAGACACC CGCTATCCCA GTGGTAGTGG ACGTCTCGGT CAGCGCTGTA GAGCTGGATA GACTTGACCA
 26 Q  M  T  Q  S  P  S  S  L  S  A  S  V  G  D  R  V  T  I  T  C  R  A  S  Q  S  V  S  T  Y  L  N  W  Y

601 ATCAACAGAA ACCAGGGAAA GCTCCGAAAG TACTGATTTA TGCTGCATCA AGTCTGCAAT CCGGAGTCCC AAGCAGATTC AGTGGCAGTG GTTCTGGGAC
    TAGTTGTCTT TGGTCCCTTT CGAGGCTTTC ATGACTAAAT ACGACGTAGT TCAGACGTTA GGCCTCAGGG TTCGTCTAAG TCACCGTCAC CAAGACCCTG
 60 Q  Q  K  P  G  K  A  P  K  V  L  I  Y  A  A  S  S  L  Q  S  G  V  P  S  R  F  S  G  S  G  S  G  T

701 GGATTACACT CTGACCATCA GCAGTCTGCA GCCAGAAGAC TTCGCAACTT ATTACTGTCT TCAGCACGGA GAGTCTCCAT GGACATTTGG ACAGGGTACC
    CCTAATGTGA GACTGGTAGT CGTCAGACGT CGGTCTTCTG AAGCGTTGAA TAATGACAGA AGTCGTGCCT CTCAGAGGTA CCTGTAAACC TGTCCCATGG
 93 D  Y  T  L  T  I  S  S  L  Q  P  E  D  F  A  T  Y  Y  C  L  Q  H  G  E  S  P  W  T  F  G  Q  G  T

801 AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
    TTCCACCTCT AGTTTGCTTG ACACCGACGT GGTAGACAGA AGTAGACAGG CGGTAGACTA CTCGTCAACT TTAGACCTTG ACGAAGACAA CACACGGACG
126 K  V  E  I  K  R  T  V  A  A  P  S  V  F  I  F  P  P  S  D  E  Q  L  K  S  G  T  A  S  V  V  C  L  L

901 TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
    ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
160 N  N  F  Y  P  R  E  A  K  V  Q  W  K  V  D  N  A  L  Q  S  G  N  S  Q  E  S  V  T  E  Q  D  S  K

1001 GGACAGCACC TACAGCCTCA GCAGCACCCT GACGCTGAGC AAAGCAGACT ACGAGAAACA CAAAGTCTAC GCCTGCGAAG TCACCCATCA GGGCCTGAGC
     CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
193  D  S  T  Y  S  L  S  S  T  L  T  L  S  K  A  D  Y  E  K  H  K  V  Y  A  C  E  V  T  H  Q  G  L  S
```

FIG. 7A

```
1101 TCGCCCGTCA CAAAGAGCTT CAACAGGGGA GAGTGTAAT TAAATCCTCT ACGGCCGGACG CATGCTGGCG AGCTCGGTAC CCGGGGATCT AGGCCTAACG
     AGCGGGCAGT GTTTCTCGAA GTTGTCCCCT CTTCACAATTA ATTTAGGAGA TGCCGGCCTGC GTAGCACCGC TCGAGCCATG GGCCCCTAGA TCCGGATTGC
226  S  P  V  T  K  S  F  N  R  G  E  C  Q                                           lambda t0 terminator^

1201 CTCGGTTGCC GCCGGGCGTT TTTTATTGTT GCCGACGCGC ATCGACTGC CAGGTGCAC CAATGCTTCT GGGCTAGGCC AGCCATGGGA AGCTGTGGTA
     GAGCCAACGG CGGCCCGCAA AAAATAACAA CGGCTGCGCG TAGAGCTGAC GTCCACGTG GTTACGAAGA CCCGATCCGG TCGGTAGCCT TCGACACCAT

1301 TGGCTGTGCA GGTCGTAAAT CACTGCATAA TTCGTGTCGC TCAAGGCGCA CTCCCGTTCT GGATAATGTT TTTTGCCGCC ACATCATAAC GGTTCTGGCA
     ACCGACACGT CCAGCATTTA GTGACGTATT AAGCACAGCG AGTTCCGCGT GAGGGCAAGA CCTATTACAA AAACGCGGC TGTAGTATTG CCAAGACCGT

1401 AATATTCTGA AATGAGCTGT TGACAATTAA TCATCGAACT AGTTTAATGT GTGAATTGTT GAGCGGATAA CAATTAAGCT TAGGATCTAG AATTATGAAG
     TTATAAGACT TTACTCGACA ACTGTTAATT AGTAGCTTGA TCAAATTACA CACTTAACAA CTCGCCTATT GTTAATTCGA ATCCTAGATC TTAATACTTC
                                                                                                        M  K
1                                                                                             Start STII signal TIR 3^

1501 AAGAATATTG CGTTCCTACT TGCCTCCTATG TTTGTCTTTT CTATAGCTAC AAACGCGTAC GCTGAGGTTC AGCTGGTGGA GTCTGGCGGT GGCCTGGTGC
     TTCTTATAAC GCAAGGATGA ACGGAGATAC AAACAGAAAA GATATCGATG TTTGCGCATG CGACTCCAAG TCGACCACCT CAGACCGCCA CCGGACCACG
3    K  N  I  A  F  L  L  A  S  M  F  V  F  S  I  A  T  N  A  Y  A  E  V  Q  L  V  E  S  G  G  G  L  V  Q
     anti-tissue factor heavy chain with cys to ser in hinge^

1601 AGCCAGGGGG CTCACTCCGT TTGTCCTGTG CAGCTTCTGG CTTCAATATT AAGGAGTACT ACATGCACTG GTCCGTCAGC GCCCCGGGTA AGGGCCTGGA
     TCGGTCCCCC GAGTGAGGCA AACAGGACAC GTCGAAGACC GAAGTTATAA TTCCTCATGA TGTAGCTGAC CAGGCAGTCG CGGGGCCCAT TCCCGGACCT
37   P  G  G  S  L  R  L  S  C  A  A  S  G  F  N  I  K  E  Y  Y  M  H  W  V  R  Q  A  P  G  K  G  L  E

1701 ATGGGTTGGA TTGATTGATC CAGAGCAAGG GTCTCGTTCC CAACACGATA TATGACCCGA AGTTCCAAGA CCGTGCCACT ATAAGGCGCT ACAATTCCAA AAACACAGCA
     TACCCAACCT AACTAATTAG GTCTCGTTCC CAGAGCAAGG GTTGTGCTAG ATACTGGGCT TCAAGGTCCT GGCACGGTGA TATTCCGCGA TGTTAAGGTT TTTGTGTCGT
70   W  V  G  L  I  D  P  E  Q  G  N  T  I  Y  D  P  K  F  Q  D  R  A  T  I  S  A  D  N  S  K  N  T  A

1801 TACCTGCAGA TGAACTCGCA GGGTCTGCGAG GCCTGTGAG GACACTGCCG TCTATTATTG TGCTCGAGAAC ACGGCCGCTT ACTTCGACTA CTGGGGTCAA GGAACCCTGG
     ATGGACGTCT ACTTGTGGA CGGAGCGTCT CCGAGACACTC CTGTGACGGC AGATAATAAC ACGAGCTCTTG TGCCGGCGAA TGAAGCTGAT GACCCCAGTT CCTTGGGACC
103  Y  L  Q  M  N  S  L  R  A  E  D  T  A  V  Y  Y  C  A  R  D  T  A  A  Y  F  D  Y  W  G  Q  G  T  L  V

1901 TCACCGTCTC CTCGGCCTCC ACCAAGGGCC CATCGGTCTT CCCCCTGGCA GAGCACCTC AGAGCACCTC TCTGTGGAC TCCCGGCTG GCAGCCCGTG GCGCCCTGG GCTGCCTGGT
     AGTGGCAGAG GAGCCGGAGG TGGTTCCCGG GTAGCCAGAA GGGGGACCGT TCTCGTGGAG AGACACCTG AGGGCCGAC CGTCGGGTGT CGCGGGACC CGACGGACCA
137  T  V  S  S  A  S  T  K  G  P  S  V  F  P  L  A  P  S  S  K  S  T  S  G  G  T  A  A  L  G  C  L  V

2001 CAAGGACTAC TTCCCCGAAC CGGTGACGGT GTCGTGGAAC TCAGGCGCCC TGACCAGCGG CGTGCACACC TTCCCGGCTG TCCTACAGTC CTCAGGACTC TACTCCTGAG
     GTTCCTGATG AAGGGGCTTG GCCACTGCCA CAGCACCTTG AGTCCGCGGG ACTGGTCGCC GCACGTGTGG AAGGGCCGAC AGGATGTCAG GAGTCCTGAG
170  K  D  Y  F  P  E  P  V  T  V  S  W  N  S  G  A  L  T  S  G  V  H  T  F  P  A  V  L  Q  S  S  G  L

2101 TACTCCCTCA GCAGCGTGGT GACTGTGCCC TCTAGCAGCT TGGGCACCCA GACCTACATC TGCAACGTGA ATCACAAGCC CAGCAACACC CAGACAGTGACA AAGGTGGACA
     ATGAGGGAGT CGTCGCACCA CTGACACGGG AGATCGTCGA ACCCGTGGGT CTGGATGTAG ACGTTGCACT TAGTGTTCGG GTCGTTGTGG GTCTGTCACT TTCCACCTGT
203  Y  S  L  S  S  V  V  T  V  P  S  S  S  L  G  T  Q  T  Y  I  C  N  V  N  H  K  P  S  N  T  K  V  D  K
```

FIG. 7B

```
2201  AGAAAGTTGA GCCCAAATCT TGTGACAAAA CTCACACTAG TCCACCGTCT CCAGGACCTG AACTCCTGGG GGGACCGTCA GTCCTCCTCT TCCCCCCAAA
      TCTTTCAACT CGGGTTTAGA ACACTGTTTA GAGTGTGATC AGGTGGCAGA GGTCGGTGAC TTGAGGACCC CCCTGGCAGT CAGGAGGAGA AGGGGGGTTT
237   K V E P K S  C D K T  H T S  P P S  P A P E  L L G  G P S  V F L F  P P P K
                                        ^Hinge cys to ser
                                        ^Hinge cys to ser 2301  ACCCAAGGAC ACCCTCATGA TCTCCCGGAC CCCTGAGGTC ACATGCGTGG TGGTGGACGT GAGCCACGAA GACCCTGAGG TCAAGTTCAA CTGGTACGTG
      TGGGTTCCTG TGGGAGTACT AGAGGCCCTG GGGACTCCAG TGTACGCACC ACCACCTGCA CTCGGTGCTT CTGGGACTCC AGTTCAAGTT GACCATGCAC
270   P K D  T L M I  S R T  P E V  T C V V  V D V  S H E  D P E V  K F N  W Y V 2401  GACGGCGTGG AGGTGCATAA TGCCAAGACA AAGCCGCGGG AGGAGCAGTA TAACAGCACG TACCGTGTGG TCAGCGTCCT CACCGTCCTG CACCAGGACT
      CTGCCGCACC TCCACGTATT ACGGTTCTGT TTCGGCGCCC TCCTCGTCAT ATTGTCGTGC ATGGCACACC AGTCGCAGGA GTGGCAGGAC GTGGTCCTGA
303   D G V E  V H N  A K T  K P R E  E Q Y  N S T  Y R V V  S V L  T V L  H Q D W 2501  GGCTGAATGG CAAGGAGTAC AAGTGCAAGG TCTCCAACAA AGCCCTCCCA GCCCCCATCG AGAAAACCAT CTCCAAAGCC AAAGGGCAGC CCCGAGAACC
      CCGACTTACC GTTCCTCATG TTCACGTTCC AGAGGTTGTT TCGGGAGGGT CGGGGGTAGC TCTTTTGGTA GAGGTTTCGG TTTCCCGTCG GGGCTCTTGG
337   L N G  K E Y  K C K V  S N K  A L P  A P I E  K T I  S K A  K G Q P  R E P 2601  ACAGGTGTAC ACCCTGCCCC CATCCCGGGA AGAGATGACC AAGAACCAGG TCAGCCTGAC CTGCCTGGTC AAAGGCTTCT ATCCCAGCGA CATCGCCGTG
      TGTCCACATG TGGGACGGGG GTAGGGCCCT TCTCTACTGG AGTTGGTCC AGTCGGACTG GACGGACCAG TTTCCGAAGA TAGGGTCGCT GTAGCGGCAC
370   Q V Y  T L P P  S R E  E M T  K N Q V  S L T  C L V  K G F Y  P S D  I A V 2701  GAGTGGGAGA GCAATGGGCA GCCGGAGAAC AACTACAAGA CCACGCCTCC CGTGCTGGAC TCCGACGGCT CCTTCTTCCT CTACAGCAAG CTCACCGTGG
      CTCACCCTCT CGTTACCCGT CGGCCTCTTG TTGATGTTCT GGTGCGGAGG GCACGACCTG AGGCTGCCGA GGAAGAAGGA GATGTCGTTC GAGTGGCACC
403   E W E S  N G Q  P E N  N Y K T  T P P  V L D  S D G S  F F L  Y S K  L T V D 2801  ACAAGAGCAG GTGGCAGCAG GGGAACGTCT TCTCATGCTC CGTGATGCAT GAGGCTCTGC ACAACCACTA CACGCAGAAG AGCCTCTCCC TGTCTCCGGG
      TGTTCTCGTC CACCGTCGTC CCCTTGCAGA AGAGTACGAG GCACTACGTA CTCCGAGACG TGTTGGTGAT GTGCGTCTTC TCGGAGAGG ACAGAGGCCC
437   K S R  W Q Q  G N V F  S C S  V M H  E A L H  N H Y  T Q K  S L S L  S P G 2901  TAAATAAGCA TCGACGGCC CTAGAGTCCC TAACGCTCGG TTGCCGCCGG GCGTTTTTTA TTGTTAACTC ATGTTTGACA GCTTATCATC GATAAGCTTT
      ATTTATTCGT AGCTGCCGG GATCTCAGGG ATTGCGAGCC AACGGCGGCC CGCAAAAAAT AACAATTGAG TACAAACTGT CGAATAGTAG CTATTCGAAA
470   K *

METHODS AND COMPOSITIONS FOR INCREASING ANTIBODY PRODUCTION

CROSS REFERENCE TO RELATED APPLICATIONS

This application is a continuation of U.S. patent application Ser. No. 10/697,995, filed Oct. 30, 2003, which application claims priority under 35 U.S.C. §119(e) to U.S. Provisional Patent Application Ser. No. 60/422,952, filed Oct. 31, 2002, the entire disclosure of all these applications are incorporated herein by reference.

TECHNICAL FIELD

The present invention relates generally to the fields of molecular biology and protein technology. More specifically, the invention concerns recombinantly produced antibodies, methods of making and uses thereof.

BACKGROUND

Recent years have seen increasing promises of using antibodies as diagnostic and therapeutic agents for various disorders and diseases. Many research and clinical applications require large quantities of functional antibodies, thus calling for large scale, economic production systems to be employed. Particularly useful is the recombinant production of antibodies using a variety of expression hosts, ranging from prokaryotes such as *E. coli* or *B. subtilis*, to yeast, plants, insect cells and mammalian cells. Kipriyanov and Little, *Mol. Biotech.* (1999), 12:173-201.

Compared to other antibody production systems, bacteria, particularly *E. coli*, provides many unique advantages. The raw materials used (i.e. bacterial cells) are inexpensive and easy to grow, therefore reducing the cost of products. Shorter generation time and ease of scaling up make bacterial fermentation a more practical means for large-scale protein production. The genomic structure and biological activity of many bacterial species, such as *E. coli*, have been well-studied and a wide range of expression vectors are available, making expression of a desirable antibody more convenient. Compared with eukaryotes, fewer steps are involved in the production process, including the manipulation of recombinant genes, stable transformation of multiple copies into the host, expression induction and characterization of the products. Pluckthun and Pack *Immunotech* 3:83-105 (1997). In addition, *E. coli* permits a unique access to random approaches. Because of the unparalleled efficiency for transformation by plasmids or transfection by phages, *E. coli* systems can be used for phage library construction of many types of antibody variants, which is particularly important in functional genomic studies.

Currently, bacterial systems are used primarily to produce antibody fragments. Like any other heterologous proteins, antibody fragments can be produced in *E. coli* either through refolding of inclusion bodies expressed in the cytoplasm, or through expression followed by secretion to the bacterial periplasm. The choice between secretion and refolding is generally guided by several considerations. Secretion is generally the faster and more commonly used strategy.

In contrast to the widespread uses of bacterial systems for expressing antibody fragments, there have been few attempts to express and recover at high yield functional intact antibodies in *E. coli*. Because of the complex feature and large size of an intact antibody, it is often difficult to achieve proper folding and assembly of the expressed light and heavy chain polypeptides, resulting in generally unacceptably poor yield of reconstituted tetrameric antibody. The expression of full length antibodies in the *E. coli* periplasm can lead to significant aggregation of the precursor chains. While it appears that heavy chains polymerize through their cysteine residues, the nature of the heavy chain aggregation is unknown.

Furthermore, since antibodies made in prokaryotes are not glycosylated, thus lacking the effector functions, the art has suggested that *E. coli* would not be a useful system for making intact antibodies, especially in light of the significant problems posed by unwanted precursor chain self aggregation and low yields. Pluckthun and Pack (1997) *Immunotech* 3:83-105; Kipriyanov and Little *Mol. Biotech.* 12:173-201 (1999); Pluckthun et al. (1996) in ANTIBODY ENGINEERING: A PRACTICAL APPROACH, pp 203-252 (Oxford Press); Pluckthun (1994) in HANDBOOK OF EXP. PHARMCOL vol 3: The Pharmcol. of Monoclonal Antibodies, pp 269-315 (ed. M. Rosenberg and G. P. Moore; Springer-Verlag, Berlin).

Restricting the use of prokaryotic systems merely to production of antibody fragments is unfortunate in view of the numerous advantages of prokaryotic systems over eukaryotic systems as described above. This is particularly relevant because recent developments in research and clinical studies have suggested that in many instances, intact antibodies are preferred over antibody fragments. An intact antibody containing the Fc region tends to be more resistant against degradation and clearance in vivo, thereby having longer biological half life in circulation. This feature is particularly desirable where the antibody is used as a therapeutic agent for diseases requiring sustained therapies. Furthermore, in many instances, intact antibodies deficient in effector functions are more desirable for therapeutic uses. Friend et al., *Transplantation* 68: 1632-1637 (1999) describe toxic effects, such as severe cytokine release syndromes, of glycosylated CD3 monoclonal antibodies when used in humans for the treatment of acute rejection episodes of organ allografts. The CD3 antibodies cause T-cell activation and cytokine release by cross-linking the T cell receptor complex as a result of FcR binding. U.S. Pat. No. 5,585,097 describes making aglycosylated CD3 antibodies by mutating certain glycosylation site residues of native CD3 antibodies. Armour et al., *Eur. J. Immunol.* 29:2613-2624 (1999) describe the use of non-destructive antibodies (i.e., lacking the effector functions) specific for HPA-1a-positive platelets in therapeutic applications where depletion of cells bearing the target antigen (i.e., the platelet cells) is undesirable. Thompson, et al., *J. Immunol Meth* 227:17-29 (1999) show that effector functions of a fully human antibody against TGFβ2 are not necessary for use in therapy of fibrotic diseases mediated by TGFβ2. Reddy, et al., *J. Immunol.* 164:1925-1933 (2000) describe liability of strong antibody-Fcγ receptor binding in treating autoimmune diseases; Isaacs, et al., *Clin. Exp. Immunol.* 106:427433(1996) suggest that if a pure blocking effect is required in vivo, an aglycosylated monoclonal antibody variant or a mutant engineered to prevent Fc receptor binding may be better choices.

The importance of antibodies in general for diagnostic, research and therapeutic purposes is reflected in the significant amount of effort that has been expended to study, and to modify antibody sequences and structures, from those found in natural antibodies, to achieve desired characteristics. Such attempts are well established in the art. See, for example, U.S. Pat. Nos. 6,165,745; 5,854,027; WO 95/14779; WO 99/25378; Chamow et al., *J. Immunol.* (1994), 153:4268-4280; Merchant et al., *Nature Biotech.* (1998), 16:677-681; Adlersberg, *Ric. Clin. Lab.* (1976), 6(3):191-205. Modifications of antibody sequences, for example those of the framework, are common. In general, however, the art recognizes that certain residues perform critical roles in conferring biochemical and functional characteristics associated with antibodies, and therefore modifications of these residues must be made with care, if at all. One such group of residues is comprised of conserved cysteine residues that form intrachain and/or interchain disulfide linkages. Conservation of these cysteines, and the apparent structural role they play, suggest that their absence or modification could lead to undesirable results. Indeed, even where attempts have been made to modify these cysteines, the thought appears to be that (i) at least a portion of the function of these cysteines must be retained in order to preserve an acceptable level of antibody integrity, function and activity; or (ii) the modification(s) can be made only in the context of antibody fragments rather than full length antibodies. See, for example, U.S. Pat. Nos. 5,892, 019; 5,348,876; 5,648,237; 5,677,425; WO 92/22583; WO 99/64460; Kim et al., *Mol. Immunol.* (1995), 32(7):467-475. Furthermore, in situations involving absence or deletion of a genetic hinge, such as described in Brekke et al. (*Nature* (1993), 363:628-630), a disulfide linkage is artificially introduced to compensate for loss of disulfide linkages resulting from the absence of wild type hinge cysteines.

In light of the discussion above, it is notable that an important advance in prokaryotic production of full length antibodies was recently disclosed. Simmons et al., PCT Pub. WO 02/061090.

Despite widespread efforts and some success in improving antibody function and antibody production methods, there remains a significant and serious need for improved methods of producing antibodies in forms that are useful for, for example, diagnostic and therapeutics utilities, and at yields that are pragmatic and commercially advantageous. The invention described herein addresses this need and provides other benefits.

All references cited herein, including patent applications and publications, are incorporated by reference in their entirety.

DISCLOSURE OF THE INVENTION

The invention provides methods, compositions, kits and articles of manufacture for producing immunoglobulins, preferably antibodies, with reduced (i.e., decreased) capability to form disulfide linkages, said immunoglobulins preferably comprising a variant heavy chain, in particular a variant hinge region in the heavy chain.

The invention provides efficient and high yield methods of producing antibodies of the invention as described herein in suitable host cells, preferably in prokaryotic cells. In one aspect, the methods of the invention comprise expressing in suitable host cells an antibody of interest in which at least one inter-heavy chain disulfide linkage is eliminated, and recovering said antibody from the host cell. In some embodiments, said antibody is one in which at least two, or any interger number up to all inter-heavy chain disulfide linkages are eliminated. In some embodiments, said antibody is one in which all inter-heavy chain disulfide linkages are eliminated. Thus, in some embodiments, said antibody comprises a variant heavy chain incapable of inter-heavy chain disulfide linkage. Preferably, said antibody of interest comprises a variant heavy chain hinge region varied such that at least one disulfide (preferably inter-molecular, preferably inter-heavy chain) linkage is eliminated. Preferably, said antibodies comprise a variant immunoglobulin hinge region that lacks at least one, at least two, at least three, at least four, or any interger number up to all, of the cysteine residues that are normally capable of forming a disulfide linkage. A variant hinge region can be rendered lacking in said cysteine residue(s) by any suitable method including deletion, substitution or modification of said residue(s). Preferably, said cysteine(s) is one that is normally capable of intermolecular disulfide linkage (preferably between cysteines of two immunoglobulin heavy chains). In some embodiments of these methods, all disulfide linkage-forming hinge cysteines of the variant heavy chain are rendered incapable of forming a disulfide linkage. In one aspect, the invention provides a method comprising expressing in a host cell an antibody in which at least one inter-heavy chain disulfide linkage is eliminated, and recovering said antibody from the host cell. In one embodiment, said antibody is expressed from a polynucleotide (which is preferably a recombinant vector) encoding said antibody. In one embodiment, the heavy and light chains of an antibody are expressed from a single polynucleotide. In another embodiment, the heavy and light chains of an antibody are expressed from separate polynucleotides. In some embodiments, these methods further comprise determining that the antibody that is recovered is biologically active.

Methods of the invention are capable of producing antibodies of the invention in amounts that are quantifiably greater than those of reference antibodies expressed under similar conditions. In some embodiments of methods of the invention, the amount of an antibody of the invention produced according to said methods is at least about 10% greater than the amount of a reference antibody expressed under similar conditions, wherein said reference antibody has a wild type ability to form disulfide linkages. In some embodiments wherein an antibody of interest comprises a variant immunoglobulin heavy chain hinge region lacking at least one, two, three, four or any interger number up to all of the cysteine residues normally capable of forming a disulfide linkage, the reference antibody may comprise an immunoglobulin heavy chain hinge region that is the wild type counterpart (preferably wild type with respect to the altered cysteine residue(s) of the variant immunoglobulin heavy chain) of the hinge region of the antibody of interest. In some embodiments, the amount is preferably at least about 25%, preferably at least about 50%, preferably at least about 75%, preferably at least about 90%, preferably at least about 150%, or preferably at least about 250%. In some embodiments, the amount is preferably from about 25% to about 300%, preferably from about 50% to about 250%, preferably from about 75% to about 200%, preferably from about 100% to about 150%.

Generally, and preferably, an antibody of the invention and a reference antibody have substantially similar biological/physiological characteristics. For example, in some embodiments of methods of the invention, an antibody of interest and a reference antibody have substantially similar antigen binding capabilities. In some embodiments, an antibody of interest and a reference antibody have substantially similar FcRn binding capabilities. In some embodiments, an antibody of interest and a reference antibody have substantially similar pharmacokinetic and/or pharmacodynamic values.

The invention provides methods of reducing undesirable self aggregation of heavy chains when expressed in host cells such as prokaryotic cells. In one aspect, the invention provides methods comprising expressing in a host cell (for e.g., a prokaryotic cell such as *E. coli*) a variant immunoglobulin heavy chain, said variant immunoglobulin heavy chain having a reduced ability to form a disulfide linkage such that amount of self aggregation (for example, in the periplasm) of the variant immunoglobulin heavy chain is less than the amount of self-aggregation of a reference immunoglobulin heavy chain when expressed under similar conditions, wherein the reference immunoglobulin heavy chain has a wild type ability to form a disulfide linkage. Preferably, said variant immunoglobulin heavy chain can be assembled or incorporated into a biologically active antibody or fragment thereof. In one embodiment, said variant immunoglobulin heavy chain comprises a hinge region in which at least one, at least two, at least three, at least four, or any interger number up to all, cysteines are rendered incapable of forming a disulfide linkage and wherein the hinge region of the reference immunoglobulin heavy chain is the wild type counterpart (prefer,ably wild type with respect to the modification(s) that results in the reduced ability to form a disulfide linkage, for example with respect to the altered cysteine residue(s) of the variant immunoglobulin heavy chain) of the variant heavy chain. In some embodiments of these methods, all disulfide linkage-forming hinge cysteines of the variant heavy chain are rendered incapable of forming a disulfide linkage. Preferably, said cysteine(s) (that is rendered incapable of forming disulfide linkage) is normally capable of intermolecular disulfide linkage.

In some embodiments of methods of the invention, the amount of self-aggregation of the variant heavy chain is preferably at least about 10%, preferably at least about 25%, preferably at least about 50%, preferably at least about 75%, preferably at least about 85%, preferably at least about 90% less than the amount of self-aggregation of the reference immunoglobulin heavy chain. In some embodiments, the amount of self-aggregation of the variant heavy chain is preferably from about 5% to about 90%, preferably from about 15% to about 80%, preferably from about 30% to about 70%, preferably from about 40% to about 60% less than the amount of self-aggregation of the reference immunoglobulin heavy chain.

The invention also provides methods of improving light and heavy chain assembly efficiency in a host cell (for e.g., prokaryotic host cells). Said methods comprise expressing in a host cell (for e.g., a prokaryotic cell such as *E. coli*) an irnmunoglobulin light chain and a variant immunoglobulin heavy chain, said variant immunoglobulin heavy chain having a reduced ability to form a disulfide linkage, whereby efficiency of assembly of the variant heavy chain and said light chain is greater than the efficiency of assembly of a reference immunoglobulin heavy chain and said light chain when expressed under similar conditions, wherein the reference immunoglobulin heavy chain is the wild type counterpart (preferably wild type with respect to the modification(s) that results in the reduced ability to form a disulfide linkage) of the variant heavy chain. In one embodiment, the invention provides methods comprising: expressing in a host cell (for e.g., a prokaryotic cell such as *E. coli*) a variant immunoglobulin heavy chain, said variant immunoglobulin heavy chain comprising a hinge region in which at least one, at least two, at least three, at least four (or any interger number up to all) cysteine is rendered incapable of forming a disulfide linkage such that efficiency of assembly of the variant heavy chain and said light chain is greater than the efficiency of assembly of a reference immunoglobulin heavy chain and said light chain when expressed under similar conditions, wherein the hinge region of the reference immunoglobulin heavy chain is the wild type counterpart (with respect to the altered cysteine residue(s) of the variant immunoglobulin heavy chain) of the hinge region of the variant heavy chain. In some embodiments of these methods, all disulfide linkage-forming hinge cysteines of the variant heavy chain are rendered incapable of forming a disulfide linkage. Preferably, said cysteine(s) (that is rendered incapable of forming disulfide linkage) is normally capable of intermolecular disulfide linkage.

In some embodiments, the assembly efficiency of the variant heavy chain is preferably at least about 25%, preferably at least about 50%, preferably at least about 75%, preferably at least about 100%, preferably at least about 150%, preferably at least about 200%, preferably at least about 300%, or preferably at least about 400%, greater than that of the reference heavy chain. In some embodiments, the assembly efficiency of the variant heavy chain is preferably between about 20% and about 500%, preferably between about 40% and about 400%, preferably between about 100% and about 300%, or preferably between about 150% and 250% greater than that of the reference heavy chain.

Any of a number of host cells can be used in methods of the invention. Such cells are known in the art (some of which are described herein) or can be determined empricially with respect to suitability for use in methods of the invention using routine techniques known in the art. Preferably, a host cell is prokaryotic. In some embodiments, a host cell is a gram-negative bacterial cell. In one embodiment, a host cell is *E. coli*. In some embodiments, the *E. coli* is of a strain deficient in endogenous protease activities. In some embodiments, the genotype of an *E. coli* host cell lacks degp and prc genes and harbors a mutant spr gene.

In some embodiments, methods of the invention further comprise expressing in a host cell a polynucleotide encoding at least one prokaryotic polypeptide selected from the group consisting of DsbA, DsbC, DsbG and FkpA. In some embodiments of these methods, the polynucleotide encodes both DsbA and DsbC.

Antibodies expressed in prokaryotic cells such as *E. coli* are aglycosylated. Thus, in some aspects, the invention provides aglycosylated antibodies produced by methods of the invention.

Antibodies expressed in host cells according to methods of the invention can be recovered from the appropriate cell compartment or medium. Factors that determine route of antibody recovery are known in the art, including, for example, whether a secretion signal is present on the antibody polypeptide, culture conditions, host genetic background (for example, some hosts can be made to leak proteins to the supernatant), etc. In some embodiments, antibody generated according to methods of the invention is recovered from cell lysate. In some embodiments, antibody generated according to methods of the invention is recovered from the periplasm or culture medium.

In one aspect, the invention provides an antibody lacking intermolecular disulfide linkage (preferably between two heavy chains). In some embodiments, said inter-heavy chain disulfide linkage is between Fc regions. In another aspect, the invention provides antibodies comprising a variant heavy chain hinge region incapable of disulfide (preferably intermolecular) linkage. In one embodiment, said variant hinge region lacks at least one cysteine, at least two, at least three, at least four or preferably any interger number up to all cysteines capable of forming a disulfide linkage (preferably intermolecular, preferably between cysteines of two immunoglobulin heavy chains). Such antibodies can be produced by, for example, using methods of the invention. Antibodies of the invention are useful for various applications and in a variety of settings. Preferably, antibodies of the invention are biologically active. Preferably, antibodies of the invention possess substantially similar biological characteristics (such as, but not limited to, antigen binding capability) and/or physico-chemical characteristics as their wild type counterparts (i.e., antibodies that differ from the antibodies of the invention primarily or solely with respect to the extent they are capable of disulfide linkage formation, for e.g., as determined by whether one or more hinge cysteines is rendered incapable of disulfide linkage formation).

Thus in some embodiments, the invention provides an antibody comprising a variant hinge region of an immunoglobulin heavy chain, wherein said variant hinge region lacks (i.e., does not comprise or contain, and/or is free of) a cysteine residue capable of forming a disulfide linkage. In some embodiments, said disulfide linkage is intermolecular (preferably inter-heavy chain). In some embodiments, said disulfide linkage is intramolecular. In some embodiments of antibodies wherein two or more cysteines are rendered incapable of disulfide linkage, all said cysteines are normally (i.e., when in wild type form) capable of intermolecular (preferably inter-heavy chain) disulfide linkage. In some embodiments of antibodies wherein two or more cysteines are rendered incapable of disulfide linkage, all said cysteines are normally capable of intermolecular (preferably inter-heavy chain) disulfide linkage. In some embodiments of antibodies wherein two or more cysteines are rendered incapable of disulfide linkage, at least one said cysteine is normally capable of intermolecular (for example, inter-heavy chain) disulfide linkage. In some embodiments, said intermolecular disulfide linkage is between cysteines of two immunoglobulin heavy chains.

In antibodies and methods of the invention, a cysteine residue can be rendered incapable of forming a disulfide linkage by any of a number of methods and techniques known in the art. For example, a hinge region cysteine that is normally capable of forming a disulfide linkage may be deleted. In another example, a cysteine residue of the hinge region that is normally capable of forming a disulfide linkage may be substituted with another amino acid, such as, for example, serine. In some embodiments, a hinge region cysteine residue may be modified such that it is incapable of disulfide bonding.

Antibodies of the invention can be of any of a variety of forms. Preferably, an antibody of the invention is a full-length antibody, which preferably comprises a heavy chain and a light chain. In one aspect, the invention provides an antibody that is humanized. In another aspect, the invention provides a human antibody. In another aspect, the invention provides a chimeric antibody. An antibody of the invention may also be an antibody fragment, such as, for example, an Fc or Fc fusion polypeptide. An Fc fusion polypeptide generally comprises an Fc sequence (or fragment thereof) fused to a heterologous polypeptide sequence (such as an antigen binding domain), such as a receptor extracellular domain (ECD) fused to an immunoglobulin Fc sequence (as exemplified for murine Flt receptor ECD fused to a murine IgG2b Fc described herein). For example, in one embodiment, an Fc fusion polypeptide comprises a VEGF binding domain, which may be a VEGF receptor, which includes flt, flk, etc. An antibody of the invention preferably comprises a heavy chain constant domain and a light chain constant domain. In some embodiments, an antibody of the invention does not contain an added, substituted or modified amino acid in the Fc region, preferably the hinge region, that is capable of disulfide (preferably intermolecular) linkage. Generally, the Fc portion (or hinge region) of an antibody of the invention is not capable of an inter-heavy chain disulfide linkage. In one embodiment, an antibody of the invention does not comprise a modification (for example, but not limited to, insertion of one or more amino acids, for e.g., to form a dimerization sequence such as leucine zipper) for formation of inter-heavy chain dimerization or multimerization. In some embodiments, a portion (but not all) of the Fc sequence is missing in an antibody of the invention. In some of these embodiments, the missing Fc sequence is a portion or all of the CH2 and/or CH3 domain. In some of these embodiments, the antibody comprises a dimerization domain (such as a leucine zipper sequence), for example fused to the C-terminus of the heavy chain fragment. In some of these embodiments, the antibody is a F(ab')$_2$.

An antibody of the invention is preferably selected from the group consisting of IgG, IgE, IgA, IgM and IgD. In some embodiments, the hinge region of an antibody of the invention is preferably of an immunoglobulin selected from the group consisting of IgG, IgA and IgD. For example, in some embodiments, an antibody or hinge region of an antibody is of IgG, which in some embodiments is IgG1 or IgG2. In some embodiments, an antibody of the invention is selected from the group consisting of IgG, IgA and IgD.

Antibodies of the invention find a variety of uses in a variety of settings. For example, an antibody of the invention may be a therapeutic antibody. In another example, an antibody of the invention may be an agonist antibody. In another example, an antibody of the invention may be an antagonistic antibody. An antibody of the invention may also be a diagnostic antibody. In yet another example, an antibody of the invention may be a blocking antibody. In another example, an antibody of the invention is a neutralizing antibody. Thus, in one aspect, the invention provides methods of treating or delaying a disease in a subject, said methods comprising administering an antibody of the invention to said subject. In one embodiment, the disease is cancer. In another embodiment, the disease is associated with unwanted angiogenesis. In another embodiment, the disease is an immune disoder, such as rheumatoid arthritis, immune thrombocytopenic purpura, systemic lupus erythematosus, etc.

Antibodies of the invention preferably retain the antigen binding capability of their wild type counterparts. Thus, antibodies of the invention are capable of binding, preferably specifically, to antigens. Such antigens include, for example, tumor antigens, cell survival regulatory factors, cell proliferation regulatory factors, molecules associated with (for e.g., known or suspected to contribute functionally to) tissue development or differentiation, cell surface molecules, lymphokines, cytokines, molecules involved in cell cycle regulation, molecules involved in vasculogenesis and molecules associated with (for e.g., known or suspected to contribute functionally to) angiogenesis. An antigen to which an antibody of the invention is capable of binding may be a member of a subset of one of the above-mentioned categories, wherein the other subset(s) of said category comprise other molecules/ antigens that have a distinct characteristic (with respect to the antigen of interest). An antigen of interest may also be deemed to belong to two or more categories. In one embodiment, the invention provides an antibody that binds, preferably specifically, a tumor antigen that is not a cell surface molecule. In one embodiment, a tumor antigen is a cell surface molecule, such as a receptor polypeptide. In another example, in some embodiments, an antibody of the invention binds, preferably specifically, a tumor antigen that is not a cluster differentiation factor. In another example, an antibody of the invention is capable of binding, preferably specifically, toga cluster differentiation factor, which in some embodiments is not, for example, CD3 or CD4. In some embodiments, an antibody of the invention is an anti-VEGF antibody, which in one embodiment comprises heavy chain CDR sequences in the sequence depicted in SEQ ID NOs: 7 or 9 (FIG. 3) or 10 or 12 (FIG. 4). In another embodiment, the antibody comprises heavy chain variable sequences of the sequence depicted in SEQ ID NOs: 7 or 9 (FIG. 3) or 10 or 12 (FIG. 4). In yet another embodiment, the antibody comprises light chain CDR sequences in the sequence depicted in SEQ ID NOs: 7 or 8 (FIG. 3) or 10 or 11 (FIG. 4), which in some embodiments further comprises heavy chain CDR sequences in the sequence depicted in SEQ ID NOs: 7 or 9 (FIG. 3) or 10 or 12 (FIG. 4). In another embodiment, the antibody comprises light chain variable sequences of the sequence depicted in SEQ ID NOs: 7 or 8 (FIG. 3) or 10 or 11 (FIG. 4). In one embodiment, the antibody comprises heavy and light chain variable sequences of the sequence depicted in SEQ ID NOs: 7, or 8 and 9 (FIG. 3) or 10, or 11 and 12 (FIG. 4). In another example, an antibody of the invention is an anti-Tissue Factor antibody, which in one embodiment comprises heavy chain CDR sequences of the sequence depicted in SEQ ID NOs: 1 or 3 (FIG. 1) or 4 or 6 (FIG. 2). In one embodiment, an antibody of the invention comprises heavy chain variable sequences of the sequence depicted in SEQ ID NOs: 1 or 3 (FIG. 1) or 4 or 6 (FIG. 2). In yet another embodiment, an antibody of the invention comprises light chain CDR sequences of the sequence depicted in SEQ ID NOs: 1 or 2 (FIG. 1) or 4 or 5 (FIG. 2), which in some embodiments further comprises heavy chain CDR sequences of the sequence depicted in SEQ ID NOs: 1 or 3 (FIG. 1), or 4 or 6 (FIG. 2). In one embodiment, an antibody of the invention comprises light chain variable sequences of the sequence depicted in SEQ ID NOs: 1 or 2 (FIG. 1), or 4 or 5 (FIG. 2). In one embodiment, an antibody of the invention comprises heavy and light chain variable sequences of the sequence depicted in SEQ ID NOs: 1, or 2 and 3 (FIG. 1), or 4, or 5 and 6 (FIG. 2).

Antibodies may be modified to enhance and/or add additional desired characteristics. Such characteristics include biological functions such as immune effector functions, a desirable in vivo half life/clearance, bioavailability, biodistribution or other pharmacokinetic characteristics. Such modifications are well known in the art and can also be determined empirically, and may include modifications by moieties that may or may not be peptide-based. For example, antibodies may be glycosylated or aglycosylated, generally depending at least in part on the nature of the host cell. Preferably, antibodies of the invention are aglycosylated. An aglycosylated antibody produced by a method of the invention can subsequently be glycosylated by, for example, using in vitro glycosylation methods well known in the art. As described above and herein, antibodies of the invention are preferably produced in a prokaryotic cell, such as, for example, *E. coli. E. coli*-produced antibodies are generally aglycosylated and lack the biological functions normally associated with glycosylation profiles found in mammalian host cell (for e.g., CHO) produced antibodies.

The invention also provides immunoconjugates comprising an antibody of the invention conjugated with a heterologous moiety. Any heterologous moiety would be suitable so long as its conjugation to the antibody does not substantially reduce a desired function and/or characteristic of the antibody. For example, in some embodiments, an immunoconjugate comprises a heterologous moiety which is a cytotoxic agent. In some embodiments, said cytotoxic agent is selected from the group consisting of a radioactive isotope, a chemotherapeutic agent and a toxin. In some embodiments, said toxin is selected from the group consisting of calichemicin, maytansine and trichothene. In some embodiments, an immunoconjugate comprises a heterologous moiety which is a detectable marker. In some embodiments, said detectable marker is selected from the group consisting of a radioactive isotope, a member of a ligand-receptor pair, a member of an enzyme-substrate pair and a member of a fluorescence resonance energy transfer pair.

In one aspect, the invention provides compositions comprising an antibody of the invention and a carrier, which in some embodiments is pharmaceutically acceptable. In another aspect, the invention provides compositions comprising an immunoconjugate as described herein and a carrier, which in some embodiments is pharmaceutically acceptable.

In another aspect, the invention provides articles of manufacture comprising a container and a composition contained therein, wherein the composition comprises an antibody of the invention,. In another aspect, the invention provides articles of manufacture comprising a container and a composition contained therein, wherein the composition comprises an immunoconjugate as described herein. In some embodiments, these articles of manufacture further comprise instruction for using said composition.

In yet another aspect, the invention provides polynucleotides encoding an antibody of the invention. In still another aspect, the invention provides polynucleotides encoding an immunoconjugate as described herein.

In one aspect, the invention provides recombinant vectors for expressing an antibody of the invention. In another aspect, the invention provides recombinant vectors for expressing an immunoconjugate of the invention.

In one aspect, the invention provides host cells comprising a polynucleotide or recombinant vector of the invention. Preferably, a host cell is a prokaryotic cell. In some embodiments, a host cell is a gram-negative bacterial cell, which in some embodiments is *E. coli*. Host cells of the invention may further comprise a polynucleotide or recombinant vector encoding at least one prokaryotic polypeptide selected from the group consisting of DsbA, DsbC, DsbG and FkpA. In some embodiments, said polynucleotide or recombinant vector encodes both DsbA and DsbC. In some embodiments, an *E. coli* host cell is of a strain deficient in endogenous protease activities. In some embodiments, the genotype of an *E. coli* host cell is that of an *E. coli* strain that lacks degP and prc genes and harbors a mutant spr gene.

It should be noted that methods and compositions of the invention as described above also provide advantages and benefits in antibody production processes besides those indicated above. For example, methods of the invention may make it easier to refold full length antibodies found in refractiles.

BRIEF DESCRIPTION OF THE DRAWINGS

FIGS. 1A-C show the expression cassette sequences of plasmid paTF50 (SEQ ID NOs: 1-3).

FIGS. 2A-D show the expression cassette sequences of plasmid pxTF2AP22 (SEQ ID NOs: 4-6).

FIGS. 3A-C show the expression cassette sequences of plasmid pxVG2AP11 (SEQ ID NOs: 7-9).

FIGS. 4A-D show the expression cassette sequences of plasmid pxVG11VNERK (SEQ ID NOs: 10-12).

FIGS. 5A-B show the 1133 base-pair ClaI-NheI fragment containing the tac promoter followed by the coding sequence for the chaperone fkpA, as described in Example 1 (SEQ ID NOs: 13-15).

FIGS. 6A-C show the approximately 1926 base-pair EcoRI-ApaI fragment encoding the phoA promoter, light chain, tac promoter, and the first part of heavy chain, as described in Example 1 (SEQ ID NOs: 16-18).

FIGS. 7A-C show the sequence of the phoA promoter, light chain, tac promoter, and heavy chain for plasmid pxTF7T3H, as described in Example 1 (SEQ ID NOs: 19-21).

MODES FOR CARRYING OUT THE INVENTION

Figure 8B:
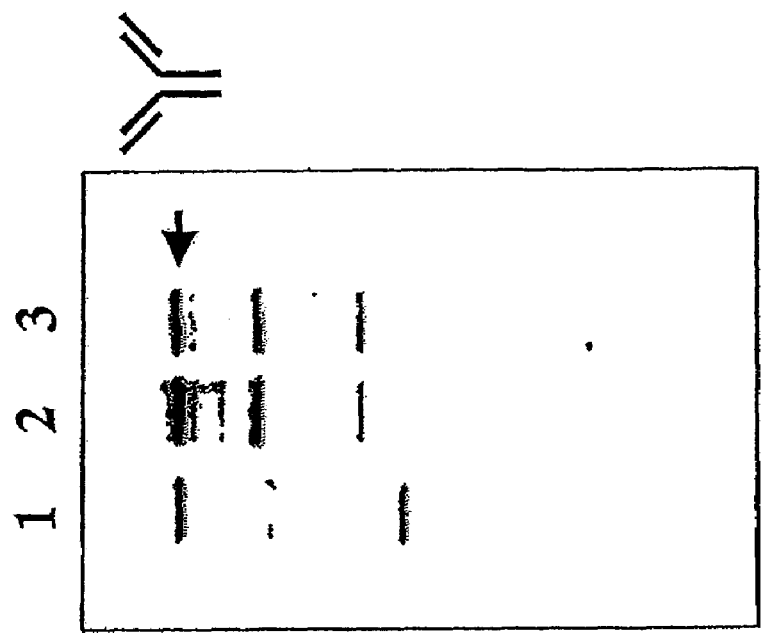
FIGS. 8A & B show western blot analyses for the conversion of single hinge cysteines to serines for the anti-tissue factor full-length antibody as well as the anti-VEGF VNERK full-length antibody. Lanes 1 reflect products with the original wild type hinges; lanes 2 reflect products with the second hinge cysteine converted to a serine; and lanes 3 reflect products with the first hinge cysteine converted to a serine. The arrows point to the full-length antibody species heavy-heavy-light-light.

The invention provides methods, compositions, kits and articles of manufacture for producing or that comprise immunoglobulins, preferably antibodies, comprising an alteration that reduces or eliminates the ability of heavy chains to form disulfide (preferably inter-molecular) linkages. Preferably these immunoglobulins comprise an alteration of at least one disulfide-forming cysteine residue such that the cysteine residue is incapable of forming a disulfide linkage. In one aspect, said cysteine(s) is of the hinge region of the heavy chain (thus, such hinge regions are referred to herein as "variant hinge region"). The invention provides immunoglobulins that when expressed are less likely to aggregate and more likely to fold-and assemble appropriately into functional immunoglobulins. In some aspects, such immunoglobulins lack the complete repertoire of heavy chain cysteine residues that are normally capable of forming disulfide linkages, either intermolecularly (such as between two heavy chains) or intramolecularly (such as between two cysteine residues in a single polypeptide chain). Generally and preferably, the disulfide linkage formed by the cysteine residue(s) that is altered (i.e., rendered incapable of forming disulfide linkages) is one that, when not present in an antibody, does not result in a substantial loss of the normal physicochemical and/or biological characteristics of the immunoglobulin. Preferably, but not necessarily, the cysteine residue that is rendered incapable of forming disulfide linkages is a cysteine of the hinge region of a heavy chain. Contrary to art teachings, it is herein shown that immunoglobulins comprising variant hinge regions in which at least one cysteine is incapable of disulfide linkage formation nonetheless possess essentially the same, and in certain contexts improved, physicochemical and/or biological functions as compared to wild type immunoglobulins. It is a further unexpected finding that immunoglobulin heavy chains comprising such variant hinge regions exhibit significantly reduced aggregation, for example and in particular when expressed in the periplasm. In addition, it has been discovered that there is a surprisingly significant increase in the amount of proper folding and assembly of immunoglobulins comprising such variant hinge regions into functional antibodies. Thus, the invention further provides methods for decreasing immunoglobulin self aggregation and for improving efficiency of light and heavy chain assembly, in particular when expressed in prokaryotic systems, for example in E. coli. The invention further provides methods for improving production of immunoglobulins comprising rendering at least one (or any number up to all) cysteine of a heavy chain binge region incapable of forming disulfide linkages, whereby increased proper folding and/or assembly of biologically active antibodies is achieved. Antibodies produced by methods of the invention comprise an incomplete repertoire or a complete absence of the disulfide linkages normally formed by cysteines, for example those formed by hinge cysteines. Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Definitions

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated.

Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be-replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Secretion signal sequence" or "signal sequence" refers to a nucleic acid sequence encoding a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). Antibodies and immunoglobulins of the invention have reduced (fewer) disulfide linkages. In one aspect, antibodies and immunoglobulins of the invention comprise a hinge region in which at least one cysteine residue is rendered incapable of forming a disulfide linkage, wherein the disulfide linkage is preferably intermolecular, preferably between two heavy chains. A hinge cysteine can be rendered incapable of forming a disulfide linkage by any of a variety of suitable methods known in the art, some of which are described herein, including but not limited to deletion of the cysteine residue or substitution of the cysteine with another amino acid.

The light chains of antibodies from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region. An antibody variant of the invention can be a full length antibody. A full length antibody can be human, humanized and/or affinity matured.

"Antibody fragments" comprise only a portion of an intact antibody, wherein the portion preferably retains at least one, preferably most or all, of the functions normally associated with that portion when present in an intact antibody. An antibody fragment of the invention comprises a sufficient portion of the constant region (preferably the Fc region) to permit dimerization (or multimerization) of heavy chains with reduced disulfide linkage capability, for example where at least one of the hinge cysteines normally involved in inter-heavy chain disulfide linkage is altered as described herein. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, or ADCC function and/or complement binding (i.e., where the antibody has a glycosylation profile necessary for ADCC function or complement binding).

A "biologically active" or "functional" immunoglobulin is one capable of exerting one or more of its natural activities in structural, regulatory, biochemical or biophysical events. For example, a biologically active antibody may have the ability to specifically bind an antigen and the binding may in turn elicit or alter a cellular or molecular event such as signaling transduction or enzymatic activity. A biologically active antibody may also block ligand activation of a receptor or act as an agonist antibody. The capability of an antibody to exert one or more of its natural activities depends on several factors, including proper folding and assembly of the polypeptide chains. Preferably, a "biologically active" antibody is an antibody that is intended to be used primarily to achieve a biological/physiological response, in vivo or ex vivo, for example to alleviate or treat diseases. Thus, for example, a "biologically active" antibody preferably does not include an antibody produced solely as a reference or control antibody used as a comparitor.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, Ann. *Allergy, Asthma & Immunol.* 1:105-115 (1998); Harris, *Biochem. Soc. Transactions* 23:1035-1038 (1995); Hurle and Gross, *Curr. Op. Biotech.* 5:428433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896.(1992).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

The "hinge region," and variations thereof, as used herein, includes the meaning known in the art, which is illustrated in, for example, Janeway et al., Immuno Biology: the immune system in health and disease, (Elsevier Science Ltd., NY) (4th ed., 1999); Bloom et al., *Protein Science* (1997), 6:407-415; Humphreys et al., *J. Immunol. Methods* (1997), 209:193-202.

An "altered" or "variant" heavy chain, as used herein, generally refers to a heavy chain with reduced disulfide linkage capability, for e.g., wherein at least one cysteine residue has been rendered incapable of disulfide linkage formation. Preferably, said at least one cysteine is in the hinge region of the heavy chain.

The phrase "amount of aggregation (or self aggregation) of variant immunoglobulin heavy chain is x % less than the amount of aggregation (or self aggregation) of a reference immunoglobulin heavy chain", and variations thereof, as used herein, means the amount of detectable insoluble aggregates of variant heavy chain polypeptides of the invention is x % less than the amount of detectable insoluble aggregates of the wild type counterpart of the altered heavy chain polypeptide. Thus, for example, if 50% of the wild type form of a heavy chain in a cell is found in insoluble aggregates while only 30% of an altered form of the heavy chain in a cell is found in insoluble aggregates, the amount of aggregation of the altered heavy chain is deemed to be 40% less. As would be understood in the art, the amount of a heavy chain polypeptide may be determined quantitatively or qualitatively, so long as a comparison between altered (variant) heavy chain and wild type heavy chain can be done. Aggregation of heavy chain polypeptides can be detected, and the amount assessed, using methods well known in the art, for example, by comparing reduced versus non-reduced whole cell lysates on an SDS gel, as indicated by, for example, degree/extent of "streakiness" of bands on an SDS-PAGE blot. Another illustrative assay is the reversed phase assay as described herein (see Example 9) which indicates total amounts of heavy chain polypeptides generated versus soluble amounts of heavy chain polypeptides (which is an indication of amounts of non-aggregated heavy chains), thus providing a basis for assessing amounts of aggregated heavy chain polypeptides. A reference immunoglobulin is preferably similar, preferably substantially identical, in amino acid sequence to the altered heavy chain polypeptide to which it is compared in this context, except for modifications in the altered heavy chain that confers reduced disulfide linkage capability, for e.g. where a cysteine(s) in the altered heavy chain polypeptide is rendered incapable of forming a disulfide linkage with another cysteine. The amount of wild type heavy chain polypeptide aggregate can be determined in parallel to or separately from determination of the amount of altered (variant) heavy chain polypeptide aggregate.

The phrase "amount of biologically active variant immunoglobulin is at least x % greater than the amount of a reference immunoglobulin", and variations thereof, as used herein, means the amount of immunoglobulin comprising a variant heavy chain that has reduced disulfide linkage capability (for e.g. where a hinge region cysteine(s) has been rendered incapable of disulfide formation) is at least x % greater than the amount of biologically active wild type counterpart of the variant immunoglobulin. Thus, for example, if y amount of biologically active wild type form of an immunoglobulin is produced while z amount of biologically active variant form of the immunoglobulin is produced, the amount of the variant form of immunoglobulin produced is deemed to be $((z-y)/y) \times 100\%$ greater. As would be understood in the art, the amount of a biologically active immunoglobulin may be determined quantitatively or qualitatively, so long as a comparison between variant immunoglobulin and wild type immunoglobulin can be done. Amount of biologically active immunoglobulin can be detected, and the amount determined, using methods well known in the art, some of which are described herein. It is understood that an immunoglobulin is deemed biologically active if it possesses at least one of its normal biological activities. The term "biologically active" is defined herein, and includes, but is not limited to, the activities described herein. A reference immunoglobulin is preferably similar, preferably substantially identical, in amino acid sequence to the variant immunoglobulin to which it is compared in this context, except for modifications in the altered heavy chain that confers reduced disulfide linkage capability, for e.g., where a cysteine(s) in the hinge region of the variant immunoglobulin is rendered incapable of forming a disulfide linkage with another cysteine. The amount of biologically active wild type immunoglobulin can be determined in parallel to or separately from determination of the amount of biologically active altered immunoglobulin.

The phrase "substantially similar," as used herein, denotes a sufficiently high degree of similarity between two numeric values (generally one associated with an antibody of the invention and the other associated with a reference antibody (as described herein)) such that one of skill in the art would consider the difference between the two values to be of little or no biological significance within the context of the biological characteristic measured by said values. The difference between said two values is preferably less than about 50%, preferably less than about 40%, preferably less than about 30%, preferably less than about 20%, preferably less than about 10% as a function of the value for the reference antibody.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Binding affinity" generally refers to the strength of the sum total of noncovalent interactions between a single binding site of a molecule (e.g., an antibody) and its binding partner (e.g., an antigen or FcRn receptor). The affinity of a molecule X for its partner Y can generally be represented by the dissociation constant (Kd). Affinity can be measured by commn methds known in the art, including those described herein. Low-affinity antibodies bind antigen (or FcRn receptor) weakly and tend to dissociate readily, whereas high-affinity antibodies bind antigen (or FcRn receptor) more tightly and remain bound longer.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $\theta^I_1$, see, e.g., Agnew *Chem Intl. Ed. Engl.* 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin (including morpholinodoxorubicin, cyanomorpholino-doxorubicin, 2-pyrrolinodoxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimnidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A "blocking" antibody or an "antagonist" antibody is one which inhibits or reduces biological activity of the antigen it binds. Such blocking can occur by any means, e.g. by interfering with: ligand binding to the receptor, receptor complex formation, tyrosine kinase activity of a tyrosine kinase receptor in a receptor complex and/or phosphorylation of tyrosine kinase residue(s) in or by the receptor. For example, a VEGF antagonist antibody binds VEGF and inhibits the ability of VEGF to induce vascular endothelial cell proliferation. Preferred blocking antibodies or antagonist antibodies substantially or completely inhibit the biological activity of the antigen.

An "agonist antibody" is an antibody which binds and activates antigen such as a receptor. Generally, the receptor activation capability of the agonist antibody will be at least qualitatively similar (and may be essentially quantitatively similar) to a native agonist ligand of the receptor.

An antibody of the invention "which binds antigen essentially as effectively as" a reference antibody is one capable of binding that antigen with affinity and/or avidity that is within about 10 fold, preferably about 5 fold, and more preferably about 2 fold, of the binding affinity and/or avidity of the reference antibody.

A "tumor antigen," as used herein, includes the meaning known in the art, which includes any molecule expressed on (or associated with the development of) a tumor cell that is known or thought to contribute to a tumorigenic characteristic of the tumor cell. Numerous tumor antigens are known in the art. Whether a molecule is a tumor antigen can also be determined according to techniques and assays well known to those skilled in the art, such as for example clonogenic assays, transformation assays, in vitro or in vivo tumor formation assays, gel migration assays, gene knockout analysis, etc.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (TTP) or autoimmune thrombocytopenia etc.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result. A "therapeutically effective amount" of the antibody may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Methods of the Invention

The expression of antibodies and antibody fragments in vivo, for example in *E. coli*, often results in significant aggregation of the precursor chains, in particular the heavy chains. This side reaction results in lower production levels of the desired completely folded antibody or antibody fragment. Whereas both heavy and light chains can be found in insoluble aggregates, it is predominantly the heavy chain which suffers this fate. Heavy chain generally folds only in the presence of light chain, and usually only a small fraction of the total heavy chain that is expressed undergoes proper folding. The nature of heavy chain aggregation is unknown. The present invention provides methods that significantly reduces antibody chain (in particular heavy chain) aggregation. The invention also provides methods of improving immunoglobulin production in vivo wherein proper folding and assembly of an immunoglobulin is significantly improved.

Accordingly, in one aspect, the invention provides methods of producing a biologically active immunoglobulin, said methods comprising expressing in a host cell an antibody in which at least one, at least two, at least three, at least four, or between two and eleven inter-heavy chain disulfide linkages are eliminated, and recovering said antibody from the host cell. Expression of said antibody can be from a polynucleotide encoding an antibody, said antibody comprising a variant heavy chain with reduced disulfide linkage capability, followed by recovering said antibody from the host cell comprising the polynucleotide. Preferably, said heavy chain comprises a variant hinge region of an immunoglobulin heavy chain, wherein at least one cysteine of said variant hinge region is rendered incapable of forming a disulfide linkage.

The invention also provides methods for reducing aggregation of immunoglobulin heavy chains, especially when the heavy chains are expressed in prokaryotic host cells. Aggregation of immunoglobulin heavy chains results in formation of insoluble complex that leads to undesirable effects. For example, as described above, aggregation of heavy chains may directly reduce immunoglobulin production in vivo by reducing the amount of heavy chain polypeptides that are available for and capable of proper folding and assembly. Furthermore, heavy chain aggregates provide a surface for the promotion of more, undesirable heavy chain aggregation. It has been unexpectedly discovered that reducing/eliminating heavy chain disulfide linkages, such as through rendering at least one cysteine of the hinge region of a heavy chain incapable of forming a disulfide linkage, significantly reduces aggregation without causing appreciable loss of biological activity of the heavy chain as compared to a wild type heavy chain (or the antibody comprising said variant heavy chain) expressed under similar conditions. In one embodiment, the amount of aggregation is at least about 10% less than the amount of aggregation of a reference immunoglobulin heavy chain expressed under similar culture conditions. In one embodiment, the hinge region of said reference immunoglobulin heavy chain is the wild type counterpart of the hinge region of the variant immunoglobulin heavy chain. In one embodiment, the amount of aggregation is at least about 25% less than the amount of aggregation of a reference immunoglobulin heavy chain expressed under similar culture conditions. In one embodiment, the amount of aggregation is at least about 50% less than the amount of aggregation of a reference immunoglobulin heavy chain expressed under similar culture conditions. In one embodiment, the amount of aggregation is at least about 75% less than the amount of aggregation of a reference immunoglobulin heavy chain expressed under similar culture conditions. In one embodiment, the amount of aggregation is from about 5% to about 90% less than the amount of aggregation of a reference immunoglobulin heavy chain expressed under similar culture conditions. In one embodiment, the amount of aggregation is from about 15% to about 80% less than the amount of aggregation of a reference immunoglobulin heavy chain expressed under similar culture conditions. In one embodiment, the amount of aggregation is from about 30% to about 70% less than the amount of aggregation of a reference immunoglobulin heavy chain expressed under similar culture conditions. In one embodiment, the amount of aggregation is from about 40% to about 60% less than the amount of aggregation of a reference immunoglobulin heavy chain expressed under similar culture conditions Generally, methods of the invention are useful for reducing aggregation of heavy chains in prokaryotic host cells, for example in the periplasm of E. coli. Host cells can be any cell suitable for expression of a heavy chain encoded by a particular polynucleotide. Host cells include prokaryotic cells, such as E. coli.

It is further anticipated that any cysteine in an immunoglobulin heavy chain can be rendered incapable of disulfide linkage formation, similarly to the hinge cysteines described herein, provided that such alteration does not substantially reduce the biological function of the immunoglobulin. For example, IgM and IgE lack a hinge region, but each contains an extra heavy chain domain; at least one (in some embodiments, all) of the cysteines of the heavy chain can be rendered incapable of disulfide linkage formation in methods of the invention so long as it does not substantially reduce the biological function of the heavy chain and/or the antibody which comprises the heavy chain.

Heavy chain hinge cysteines are well known in the art, as described in, for example, "Sequences of proteins of immunological interest" by Kabat. As is known in the art, the number of hinge cysteines varies depending on the class and subclass of immunoglobulin. See, for example, Janeway, "Immunobiology", 4th Ed., (Garland Publishing, NY). For example, in human IgG1s, there are two hinge cysteines that are separated by two prolines, and these are normally paired with their counterparts on an adjacent heavy chain in intermolecular disulfide linkages. Other examples include human IgG2 which contains 4 hinge cysteines, IgG3 which contains 11 hinge cysteines, and IgG4 which contains 2 hinge cysteines. Accordingly, in one embodiment, methods of the invention comprise expressing in a host cell an immunoglobulin heavy chain comprising a variant hinge region, wherein at least one cysteine of said variant hinge region is rendered incapable of forming a disulfide linkage, allowing said heavy chain to complex with a light chain to form a biologically active antibody, and recovering said antibody from the host cell. In another embodiment, methods of the invention comprise expressing in a host cell an immunoglobulin heavy chain comprising a variant hinge region, wherein at least two cysteines of said variant hinge region are rendered incapable of forming a disulfide linkage, allowing said heavy chain to complex with a light chain to form a biologically active antibody, and recovering said antibody from the host cell. In one embodiment, methods of the invention comprise expressing in a host cell an immunoglobulin heavy chain comprising a variant hinge region, wherein at least three cysteines of said variant hinge region are rendered incapable of forming a disulfide linkage, allowing said heavy chain to complex with a light chain to form a biologically active antibody, and recovering said antibody from the host cell. In one embodiment, methods of the invention comprise expressing in a host cell an immunoglobulin heavy chain comprising a variant hinge region, wherein from about two to about eleven cysteines of said variant hinge region are rendered incapable of forming a disulfide linkage, allowing said heavy chain to complex with a light chain to form a biologically active antibody, and recovering said antibody from the host cell. In one embodiment, methods of the invention comprise expressing in a host cell an immunoglobulin heavy chain comprising a variant hinge region, wherein at least four cysteines of said variant hinge region are rendered incapable of forming a disulfide linkage, allowing said heavy chain to complex with a light chain to form a biologically active antibody, and recovering said antibody from the host cell. In one embodiment, methods of the invention comprise expressing in a host cell an immunoglobulin heavy chain comprising a variant hinge region, wherein all cysteines of said variant hinge region are rendered incapable of forming a disulfide linkage, allowing said heavy chain to complex with a light chain to form a biologically active antibody, and recovering said antibody from the host cell.

Light chains and heavy chains constituting antibodies of the invention as produced according to methods of the invention may be encoded by a single polynucleotide or by separate polynucleotides.

Cysteines normally involved in disulfide linkage formation can be rendered incapable of forming disulfide linkages by any of a variety of methods known in the art, that would be evident to one skilled in the art in view of the criteria described herein. For example, a hinge cysteine can be substituted with another amino acid, such as serine, which is not capable of disulfide bonding. Amino acid substitution can be achieved by standard molecular biology techniques, such as site directed mutagenesis of the nucleic acid sequence encoding the hinge region that is to be modified. Suitable techniques include those-described in Sambrook et al., supra. Other techniques for generating immunoglobulin with a variant hinge region include synthesizing an oligonucleotide comprising a sequence that encodes a hinge region in which the codon that encodes the cysteine that is to be substituted is replaced with a codon that encodes the substitute amino acid. This oligonucleotide can then be ligated into a vector backbone comprising other appropriate antibody sequences, such as variable regions and Fc sequences, as appropriate. Details of examples of these techniques are further described in the Examples section below. In another example, a hinge cysteine can be deleted. Amino acid deletion can be achieved by standard molecular biology techniques, such as site directed mutagenesis of the nucleic acid sequence encoding the hinge region that is to be modified. Suitable techniques include those described in Sambrook et al., supra. Other techniques for generating immunoglobulin with a variant hinge region include synthesizing an oligonucleotide comprising a sequence that encodes a hinge region in which the codon that encodes the cysteine that is to be modified is deleted. This oligonucleotide can then be ligated into a vector backbone comprising other appropriate antibody sequences, such as variable regions and Fc sequences, as appropriate.

Antigen Specificity

The present invention is applicable to antibodies of any appropriate antigen binding specificity. Preferably, the antibodies of the invention are specific to antigens that are biologically important polypeptides. More preferably, the antibodies of the invention are useful for therapy or diagnosis of diseases or disorders in a mammal. Immunoglobulins made according to the present invention are particularly useful as therapeutic antibodies such as blocking antibodies, agonist antibodies, neutralizing antibodies or antibody conjugates. Aglycosylated immunoglobulins made according to the invention in prokaryotic cells (such as E. coli) are also useful for these purposes. Non-limiting examples of therapeutic antibodies include anti-VEGF, anti-IgE, anti-CD11, anti-CD18, anti-CD40, anti-tissue factor (IF), anti-HER2, and anti-TrkC antibodies. Antibodies directed against non-polypeptide antigens (such as tumor-associated glycolipid antigens) are also contemplated.

Where the antigen is a polypeptide, it may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins such as CD11a, CD11b, CD11c, CD18, an ICAM, VLA-4 and VCAM; a tumor associated antigen such as HER2,IHER3 or HER4 receptor; and fragments of any of the above-listed polypeptides.

Preferred antigens for antibodies encompassed by the present invention include CD proteins such as CD3, CD4, CD8, CD19, CD20, CD34, and CD46; members of the ErbB receptor family such as the EGF receptor, HER2, HER3 or HER4 receptor; cell adhesion molecules such as LFA-1, Mac1, p150.95, VLA-4, ICAM-1, VCAM, α4/β7 integrin, and αv/β3 integrin including either α or β subunits thereof (e.g. anti-CD11a, anti-CD18 or anti-CD11b antibodies); growth factors such as VEGF; tissue factor (TF); TGF-β; alpha interferon (α-IFN); an interleukin, such as IL-8; IgE; blood group antigens Apo2, death receptor; flk2/flt3 receptor; obesity (OB) receptor; mpl receptor; CTLA-4; protein C etc. The most preferred targets herein are VEGF, TF, CD19, CD20, CD40, TGF-β, CD11a, CD18, Apo2 and C24.

In some embodiments, an antibody of the invention is capable of binding specifically to a tumor antigen. In some embodiments, an antibody of the invention is capable of binding specifically to a tumor antigen wherein the tumor antigen is not a cluster differentiation factor (i.e., a CD protein). In some embodiments, an antibody of the invention is capable of binding specifically to a CD protein. In some embodiments, an antibody of the invention is capable of binding specifically to a CD protein other than CD3 or CD4. In some embodiments, an antibody of the invention is capable of binding specifically to a CD protein other than CD19 or CD20. In some embodiments, an antibody of the invention is capable of binding specifically to a CD protein other than CD40. In some embodiments, an antibody of the invention is capable of binding specifically to CD19 or CD20. In some embodiments, an antibody of the invention is capable of binding specifically to CD40. In some embodiments, an antibody of the invention is capable of binding specifically to CD11.

In one embodiment, an antibody of the invention is capable of binding specifically to a cell survival regulatory factor. In some embodiments, an antibody of the invention is capable of binding specifically to a cell proliferation regulatory factor. In some embodiments, an antibody of the invention is capable of binding specifically to a molecule involved in cell cycle regulation. In other embodiments, an antibody of the invention is capable of binding specifically to a molecule involved in tissue development or cell differentiation. In some embodiments, an antibody of the invention is capable of binding specifically to a cell surface molecule. In some embodiments, an antibody of the invention is capable of binding to a tumor antigen that is not a cell surface receptor polypeptide.

In one embodiment, an antibody of the invention is capable of binding specifically to a lymphokine. In another embodiment, an antibody of the invention is capable of binding specifically to a cytokine.

In one embodiment, antibodies of the invention are capable of binding specifically to a molecule involved in vasculogenesis. In another embodiment, antibodies of the invention are capable of binding specifically to a molecule involved in angiogenesis.

Soluble antigens or fragments thereof, optionally conjugated to other molecules, can be used as immunogens for generating antibodies. For transmembrane molecules, such as receptors, fragments of these molecules (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

The antibodies of the present invention may be monospecific, bispecific, trispecific or of greater multispecificity. Multispecific antibodies may be specific to different epitopes of a single molecule or may be specific to epitopes on different molecules. Methods for designing and making multispecific antibodies are known in the art. See, e.g., Millstein et al. (1983) *Nature* 305:537-539; Kostelny et al. (1992) *J. Immunol.* 148:1547-1553; WO 93/17715.

Vector Construction

Polynucleotide sequences encoding the immunoglobulin polypeptides of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the immunoglobulins are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237, and the "Examples" section herein below.

In addition, phage vectors containing replicon and control sequences that are compatible with the host microorganism can be used as transforming vectors in connection with these hosts. For example, bacteriophage such as λGEM.™.-11 may be utilized in making a recombinant vector which can be used to transform susceptible host cells such as *E. coli* LE392.

In some embodiments, a heavy chain and a light chain of an antibody of the invention are encoded on a single polynucleotide. In some of these embodiments, an expression vector used in methods of the invention comprises at least two promoter-cistron pairs, one for the immunoglobulin light chain and the other for the immunoglobulin heavy chain. Promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature. In some embodiments, a heavy chain and a light chain of an antibody of the invention are encoded on separate polynucleotides.

Although both constitutive and inducible promoters can be used in the present invention, inducible promoters under high regulation are generally preferred in the expression vectors disclosed herein. A large number of promoters recognized by a variety of potential host cells are well known. The selected promoter can be operably linked to cistron DNA encoding a light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) *Cell* 20: 269) using linkers or adaptors to supply any required restriction sites. More preferred promoter for use in this invention is the PhoA promoter.

In one embodiment, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

Immunoglobulins of the present invention can also be expressed from an expression system in which the quantitative ratio of expressed light and heavy chains can be modulated in order to maximize the yield of secreted and properly assembled full length antibodies. Such modulation is accomplished by simultaneously modulating translational strengths for light and heavy chains.

One technique for modulating translational strength is disclosed in Simmons et al. U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One preferred method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of full length products under various TIR strength combinations. TIR strengths can be determined by quantifying the expression level of a reporter gene as described in detail in Simmons et al. U.S. Pat. No. 5,840,523. For the purpose of this invention, the translational strength combination for a particular pair of TTRs within a vector is represented by (N-light, M-heavy), wherein N is the relative TIR strength of light chain and M is the relative TIR strength of heavy chain. For example, (3-light, 7-heavy) means the vector provides a relative TIR strength of about 3 for light chain expression and a relative TIR strength of about 7 for heavy chain expression. Based on the translational strength comparison, the desired individual TIRs are selected to be combined in the expression vector constructs of the invention.

Prokaryotic host cells suitable for expressing immunoglobulins of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus.* Preferably, gram-negative cells are used. More preferably, *E. coli* cells are used as hosts for the invention. Preferred *E. coli* strain are strain W3110 (Bachmann, *Cellular and Molecular Biology,* vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Of course other strains and derivatives thereof, such as *E. coli* 294 (ATCC 31,446), *E. coli* B, *E. coli*$_\lambda$ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Preferably the host cell should secrete minimal amounts of proteolytic enzymes, and additional protease inhibitors may desirably be incorporated in the cell culture. Also, methods of the invention may also utilize host cells comprising mutation(s) in the thioredoxin and/or glutathione pathways; indeed, the invention provides a method of generating full length antibodies that accumulate in the cytoplasm of a host cell comprising mutation(s) in the thioredoxin and/or glutathione pathways.

Immunoglobulin Production

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For $E.$ $coli$ growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For $E.$ $coli$, the pH is preferably from about 6.8 to about 7.4, and more preferably about 7.0.

If an inducible promoter is used in the expression vector of the invention, protein expression is induced under conditions suitable for the activation of the promoter. In one aspect of the invention, two PhoA promoters are used for controlling transcription of the light and heavy chains. Accordingly, the transformed host cells may be cultured in a phosphate-limiting medium for induction. Preferably, a phosphate-limiting medium is the medium as described in detail below in Example 2 or 3. A variety of other inducers may be used, according to the vector construct employed, as is known in the art.

The immunoglobulin polypeptides of the present invention expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

In one embodiment of the invention, immunoglobulin production is conducted in large quantity by a fermentation process. Various large-scale batch-fed fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper folding and assembly of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) $J$ $Bio$ $Chem$ 274:19601-19605; Georgiou et al., U.S. Pat. No. 6,083,715; Georgiou et al., U.S. Pat. No. 6,027,888; Bothmann and Pluckthun (2000) $J.$ $Biol.$ $Chem.$ 275:17100-17105; Ramm and Pluckthun (2000) $J.$ $Biol.$ $Chem.$ 275:17106-17113; Arie et al. (2001) $Mol.$ $Microbiol.$ 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease L Protease Mi, Protease V, Protease VI and combinations thereof. Some $E.$ $coli$ protease-deficient strains are available and described in, for example, Joly et al. (1998), supra; Georgiou et al., U.S. Pat. No. 5,264,365; Georgiou et al., U.S. Pat. No. 5,508,192; Hara et al., $Microbial$ $Drug$ $Resistance,$ 2:63-72 (1996).

In a one embodiment, $E.$ $coli$ strains deficient for proteolytic enzymes and transformed with plasmids overexpressing one or more chaperone proteins are used as host cells in the expression system of the invention. Some of these strains are further described in the Examples section below.

Antibody Purification

In one embodiment, the immunoglobulin polypeptide produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the immunoglobulins of the invention. Protein A is a 41 kD cell wall protein from $Staphylococcus$ $aureas$ which binds with a high affinity to the Fc region of antibodies. Lindmark et al (1983) $J.$ $Immunol.$ $Meth.$ 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the immunoglobulin of interest to Protein A. The solid phase is then washed to remove contaminants non-specifically bound to the solid phase. Finally the immunoglobulin is recovered from the solid phase by elution.

Activity Assays

The immunoglobulins of the present invention can be characterized for their physical/chemical properties and biological functions by various assays known in the art. In one aspect of the invention, it is important to compare the altered immunoglobulin of the present invention to a reference (generally wild type counterpart) immunoglobulin. Particularly, the quantity of an altered immunoglobulin of the present invention expressed according to a method of the invention can be compared to that of a reference immunoglobulin expressed under similar culture conditions. Methods for protein quantification are well known in the art. For example, samples of the expressed proteins can be compared for their quantitative intensities on a Coomassie-stained SDS-PAGE. Alternatively, the specific band(s) of interest (e.g., the full length band) can be detected by, for example, western blot gel analysis and/or AME5-RP assay.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that is aglycosylated. The unique features of the antibody (i.e., having an intact Fc region, yet lacking effector functions) make it a desired candidate for many applications in which the half life of the antibody in vivo is important yet the effector functions (i.e., complement and ADCC) are unnecessary or deleterious. In certain embodiments, the Fc activities of the produced immunoglobulin are measured to ensure that only the desirable properties are maintained. For example, Fc receptor (FcR) binding assays can be conducted to ensure that the antibody lacks FcγR1 binding (hence lacks ADCC toxicity), but retains FcRn binding ability. C1q binding assays may also be carried out to confirm that the antibody is unable to bind C1q and hence lacks CDC activity. In vitro and in vivo cytotoxicity assays can be conducted to confirm the depletion of CDC and/or ADCC activities. Techniques for carrying out these assays are known in the art. Illustrative procedural details are provided in the Examples section.

Humanized Antibodies

The present invention encompasses humanized antibodies. Various methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N— or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |
| Thr (T) | ser | ser |

TABLE 1-continued

| Original Residue | Exemplary Substitutions | Preferred Substitutions |
|---|---|---|
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.
Non-conservative substitutions will entail exchanging a member of one of these classes for another class.

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG$^4$ Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one-or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an FcγR may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an FcγRI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an FcγRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter *Nature* 322:738-40 (1988); U.S. Pat. No. 5,648,260; U.S. Pat. No. 5,624,821; and WO94/29351 concerning Fc region variants.

Immunoconjugates

The invention also pertains to immunoconjugates comprising an immunoglobulin polypeptide of the invention conjugated to a cytotoxic agent such as a chemotherapeutic agent (as defined and described herein above), toxin (e.g. a small molecule toxin or an enzymatically active toxin of bacterial, fungal, plant or animal origin, including fragments and/or variants thereof), or a radioactive isotope (i.e., a radioconjugate).

Conjugates of an antibody and one or more small molecule toxins, such as a calicheamicin, a maytansine (U.S. Pat. No. 5,208,020), a trichothene, and CC1065 are also contemplated herein.

In one embodiment of the invention, the immunoglobulin is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an immunoglobulin conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an immunoglobulin of the invention and a compound with nucleolytic activity (e.g. a ribonuclease or a DNA endonuclease such as a deoxyribonuclease; DNase).

A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the immunoglobulin of the invention and cytotoxic agent may be made using a variety of bifunctional protein coupling agents such as N-succinimidyl-3-(2-pyridyldithiol)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(pdiazoniumbenzoyl)-ethylenediamine), diisocyanates (such as tolyene 2,6-diisocyanate), and bis-active fluorine compounds (such as 1,5-difluoro-2,4-initrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the immunoglobulin and cytotoxic agent may be made, e.g. by recombinant techniques or peptide synthesis.

In yet another embodiment, an immunoglobulin of the invention may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Derivatives

The antibodies and antibody variants of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and or type of polymers used for derivatization can be determined based on considerations including, but not limited to, the particular properties or functions of the antibody to be improved, whether the antibody derivative will be used in a therapy under defined conditions.

In general, an immunoglobulin produced by the prokaryotic expression system described herein is aglycosylated and lacks the effector activities of the Fc region. In some instances, it may be desirable to at least partially restore one or more effector functions of the native immunoglobulin (generally an antibody). The present invention contemplates a method for restoring the effector function(s) by attaching suitable moieties to identified residue sites in the Fc region of the aglycosylated antibody. A preferred moiety for this purpose is PEG, although other carbohydrate polymers can also be used. Pegylation may be carried out by any of the pegylation reactions known in the art. See, for example, EP 0401384; EP 0154316; WO 98/48837. In one embodiment, cysteine residues are first substituted for residues at identified positions of the antibody, such as those positions wherein the antibody or antibody variant is normally glycosylated or those positions on the surface of the antibody. Preferably, the cysteine is substituted for residue(s) at one or more positions 297, 298, 299, 264, 265 and 239 (numbering according to the EU index as in Kabat). After expression, the cysteine substituted antibody variant can have various forms of PEG (or pre-synthesized carbohydrate) chemically linked to the free cysteine residues.

Pharmaceutical Formulations

Therapeutic formulations comprising an antibody of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate)microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No.3,773, 919), copolymers of L-glutamic acid and γ ethyl-L-glutamate, non-degradable ethylene-vinyl acetate, degradable. lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. In this regard, reduction/elimination of disulfide forming cysteine residues as described herein may be particularly advantageous.

Uses

An immunoglobulin of the present invention may be used, for example, to purify, detect, and target a specific polypeptide it recognizes, including both in vitro and in vivo diagnostic and therapeutic methods.

In one aspect, an immunoglobulin of the invention can be used in immunoassays for qualitatively and quantitatively measuring specific antigens in biological samples. Conventional methods for detecting antigen-antibody binding includes, for example, an enzyme-linked immunosorbent assay (ELISA), a radioimmunoassay (RIA) or tissue immunohistochemistry. Many methods may use a label bound to an antibody for detection purposes. The label used with the antibody is any detectable functionality (moiety) that does not interfere with its binding to antibody. Numerous labels are known, including the radioisotopes $^{32}P$, $^{32}S$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotinlavidin, spin labels, bacteriophage labels, stable free radicals, imaging radionuclides (such as Technecium) and the like. Production and detection of signal associated with certain labels can be direct, or indirect involving interactions between two or more interactive moieties, such as a ligand-receptor pair, enzyme-substrate pair and fluorescence resonance energey transfer pair.

Conventional methods are available to bind these labels covalently to the immunoglobulin polypeptides. For instance, coupling agents such as dialdehydes, carbodiimides, dimaleimides, bis-imidates, bis-diazotized benzidine, and the like may be used to tag the antibodies with the above-described fluorescent, chemilumninescent, and enzyme labels. See, for example, U.S. Pat. No. 3,940,475 (fluorimetry) and U.S. Pat. No. 3,645,090 (enzymes); Hunter et al. *Nature* 144: 945 (1962); David et al. *Biochemistry* 13:1014-1021 (1974); Pain et al. *J. Immunol. Methods* 40:219-230 (1981); and Nygren *Histochem. and Cytochem* 30:407-412 (1982). Preferred labels herein are enzymes such as horseradish peroxidase and alkaline phosphatase. The conjugation of such label, including the enzymes, to the immunoglobulin polypeptide is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981 ), pp. 147-166. Such bonding methods are suitable for use with the immunoglobulin polypeptides of this invention.

Alternative to labeling the immunoglobulin, antigen can be assayed in biological fluids by a competition immunoassay utilizing a competing antigen standard labeled with a detectable substance and an unlabeled antibody. In this assay, the biological sample, the labeled antigen standards and the antibody are combined and the amount of labeled antigen standard bound to the unlabeled antibody is determined. The amount of tested antigen in the biological sample is inversely proportional to the amount of labeled antigen standard bound to the antibody.

In one aspect, an aglycosylated immunoglobulin of the invention is particularly useful to detect and profile expressions of specific surface antigens in vitro or in vivo. As discussed before, the aglycosylated antibody does not exert effector functions (i.e., ADCC or CDC activity). Therefore, when the antibody binds to the cell surface antigen, it will not initiate undesirable cytotoxic events. The surface antigen can be specific to a particular cell or tissue type, therefore serving as a marker of the cell or tissue type. Preferably, the surface antigen marker is differentially expressed at various differentiation stages of particular cell or tissue types. The immunoglobulin directed against such surface antigen can thus be used for the screening of cell or tissue populations expressing the marker. For example, the immunoglobulin of the invention can be used for the screening and isolation of stem cells such as embryonic stem cells, hematopoietic stem cells and mesenchymal stem cells. The immunoglobulin of the invention can also be used to detect tumor cells expressing tumor-associated surface antigens such HER2, HER3. or HER4 receptors.

An immunoglobulin of the invention may be used as an affinity purification agent. In this process, the immunoglobulin polypeptide is immobilized on a solid phase such as Sephadex resin or filter paper, using methods well known in the art. The immobilized immunoglobulin is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the immunoglobulin.

The immunoglobulins of the invention can be used as an antagonist to partially or fully block the specific antigen activity both in vitro and in vivo. Moreover, at least some of the immunoglobulins of the invention can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the immunoglobulin of the invention can be used for inhibiting antigen activities by contacting the immunoglobulin with the antigen such that antigen activity is inhibited. Preferably, the antigen is a human protein molecule.

In another embodiment, an immunoglobulin of the invention can be used in a method for inhibiting an antigen in a subject suffering from a disorder in which the antigen activity is detrimental, comprising administering to the subject an immunoglobulin of the invention such that the antigen activity in the subject is inhibited. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An immunoglobulin of the invention can be administered to a human subject for therapeutic purposes. Moreover, an immunoglobulin of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but not limited to, anti-VEGF, anti-IgE, anti-CD11, anti-interferon and anti-tissue factor antibodies. The immunoglobulins of the invention can be used to diagnose, treat, inhibit or prevent diseases, disorders or conditions associated with abnormal expression and/or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one aspect, a blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. The invention also encompasses antibodies that either preferably or exclusively bind to ligand-receptor complexes. An immunoglobulin of the invention can also act as an agonist of a particular antigen receptor, thereby potentiating, enhancing or activating either all or partial activities of the ligand-mediated receptor activation.

In certain embodiments, an immunoconjugate comprising an immunoglobulin conjugated with a cytotoxic agent is administered to the patient. Preferably, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Immunoglobulins of the present invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. For instance, anti-VEGF antibodies blocking VEGF activities may be combined with anti-ErbB antibodies (e.g. HERCEPTIN® anti-HER2 antibody) in a treatment of metastatic breast cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the immunoglobulin of the invention can occur prior to, and/or following, administration of the adjunct therapy or therapies.

The immunoglobulin of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the immunoglobulin is suitably administered by pulse infusion, particularly with declining doses of the antibody. Preferably the dosing is given by injections, most preferably intravenous or subcutaneous injections, depending in part on whether the administration is brief or chronic.

The immunoglobulin composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The immunoglobulin need not be, but is optionally formulated with one or more agents currently used to prevent or treat the disorder in question. The effective amount of such other agents depends on the amount of immunoglobulins of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an immunoglobulin of the invention (when used alone or in combination with other agents such as chemotherapeutic agents) will depend on the type of disease to be treated, the type of antibody, the severity and course of the disease, whether the immunoglobulin is administered for preventive or therapeutic purposes, previous therapy, the patient's clinical history and response to the immunoglobulin, and the discretion of the attending physician. The immunoglobulin is suitably administered to the patient at one time or over a series of treatments. Depending on the type and severity of the disease, about 1 μg/kg to 15 mg/kg (e.g. 0.1 mg/kg-10 mg/kg) of immunoglobulin is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. The preferred dosage of the antibody or antibody fragment will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the immunoglobulin. However, other dosage regimens may be useful. The progress of this therapy is easily monitored by conventional techniques and assays.

Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an immunoglobulin of the invention. The label or package insert indicates that the composition is used for treating the condition of choice, such as cancer. Moreover, the article of manufacture may comprise (a) a first container with a composition contained therein, wherein the composition comprises an immunoglobulin of the invention; and (b) a second container with a composition contained therein, wherein the composition comprises a further cytotoxic agent. The article of manufacture in this embodiment of the invention may further comprise a package insert indicating that the first and second immunoglobulin compositions can be used to treat cancer. Alternatively, or additionally, the article of manufacture may further comprise a second (or third) container comprising a pharmaceutically-acceptable buffer, such as bacteriostatic water for injection (BWH), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

The following Examples are provided to illustrate, but not limit, the invention.

EXAMPLES

Example 1

Construction of Expression Vectors

To assess the effects of reducing/eliminating the ability of heavy chains to form disulfide linkages, various expression constructs were utilized in experiments to assess effects of eliminating disulfide forming capabilities of cysteine residues in antibody heavy chains as described herein. All plasmids for the expression of full-length antibodies were based on a separate cistron system (Simmons et al., *J. Immunol. Methods* (2002), 263:133-147) which relied on separate phoA promoters (AP) (Kikuchi et al., *Nucleic Acids Res.* 9:5671-5678, 1981) for the transcription of both heavy and light chains, followed by trp Shine-Dalgarno sequences for translation initiation (Yanofsky et al., *Nucleic Acids Res.* 9:6647-6668, 1981, and Chang et al., *Gene* 55:189-196, 1987). Additionally the heat-stable enterotoxin II signal sequence (SET) (Picken et al., *Infect. Immun.* 42:269-275, 1983, and Lee et al., *Infect. Immun.* 42:264-268, 1983) was used for the periplasmic secretion of heavy and light chains. Fine control of translation for both chains was achieved with previously described STII signal sequence variants of measured relative translational strengths, which contain silent codon changes in the translation initiation region (TIR) (Simmons and Yansura, *Nature Biotechnol.* 14:629-634, 1996; Simmons et al., *J. Immunol. Methods* (2002), 263:133-147). Finally the λ to transcriptional terminator (Schlotissek and Grosse, *Nucleic Acids Res.* 15:3185, 1987) was placed downstream of the coding sequences for both light and heavy chains. All plasmids use the framework of a pBR322-based vector system (Sutcliffe, Cold Spring Harbor Symp. Quant. Biol. 43:77-90, 1978).

The Fc fusion plasmids were identical to the full-length antibody constructs, with the exception that there is only one polypeptide chain to be expressed, which is a derivative of heavy chain. All of the control elements including the AP promoter, STII signal sequence, and the λ to transcriptional terminator were the same.

Plasmid paTF50

Figure 1A:
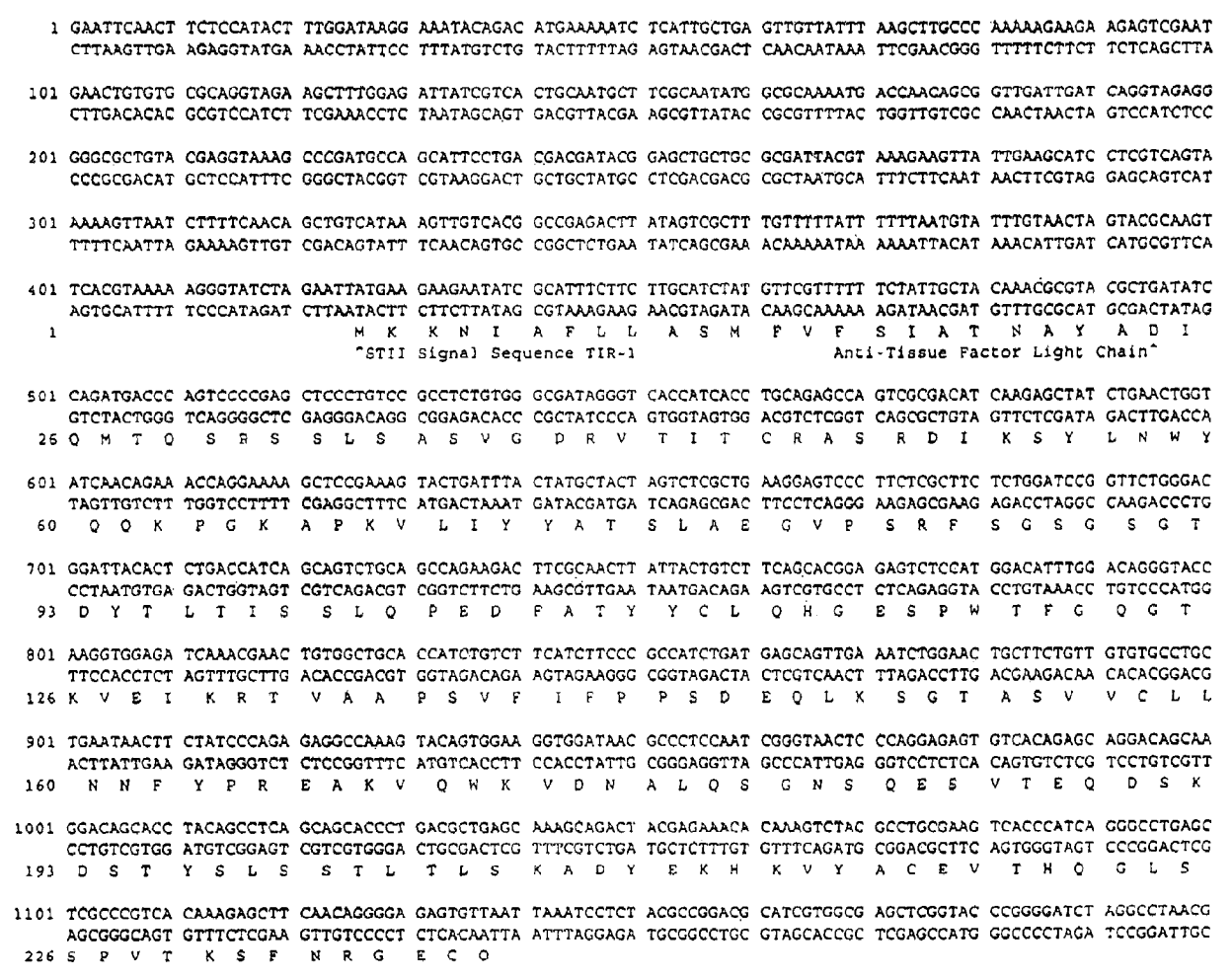
Figure 1B:
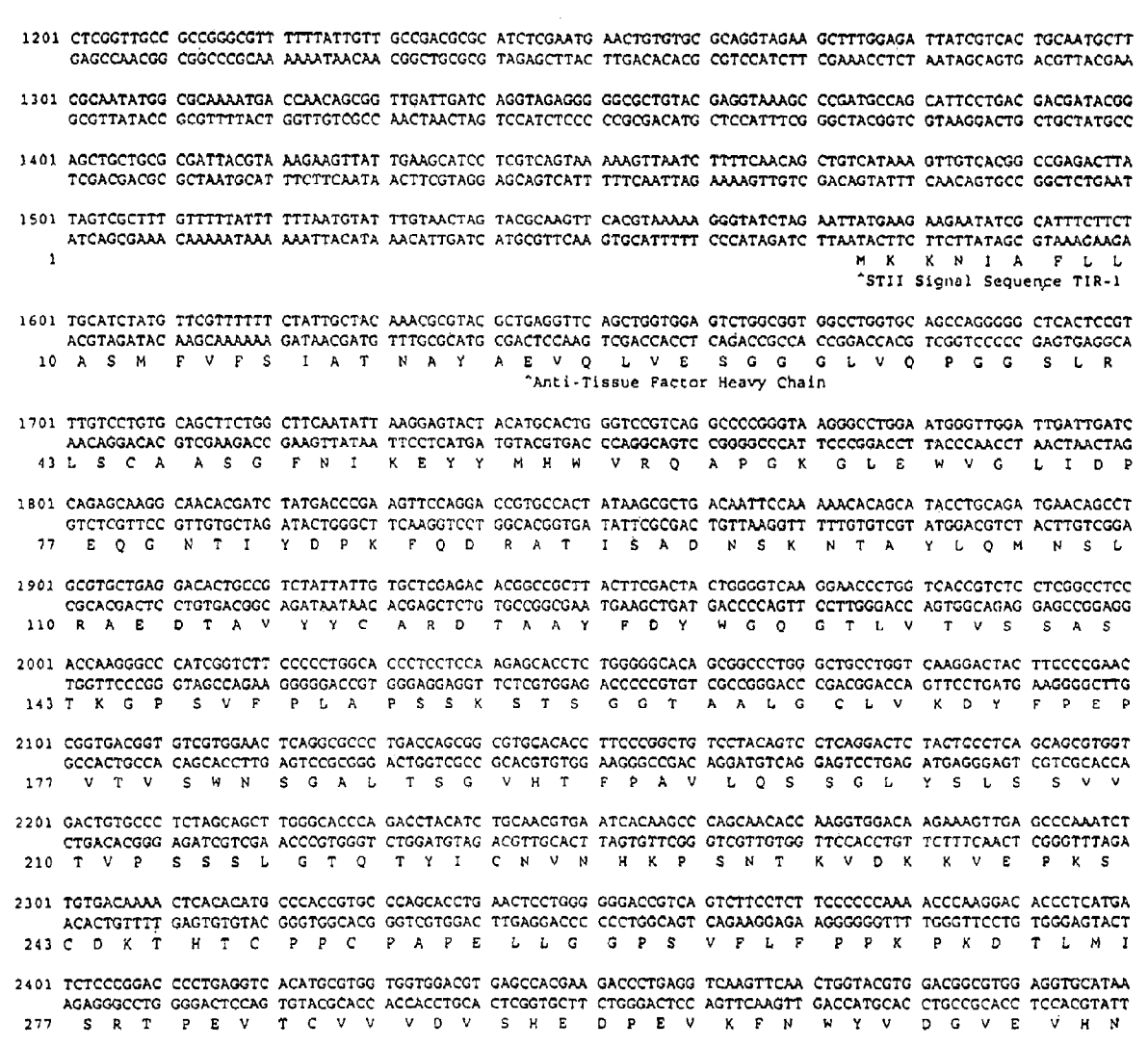

Plasmid paTF50 was constructed by cloning an expression cassette into the framework of the *E. coli* plasmid pBR322 at the EcoRI site. Sutcliffe (1978) Cold Spring Harbor Symp. Quant. Biol. 43:77-90. The expression cassette sequence of paTF50 (for anti-TF; SEQ ID NOs: 1-3) are provided in FIG. 1.

Plasmid pxTF2AP22

Figure 2A:
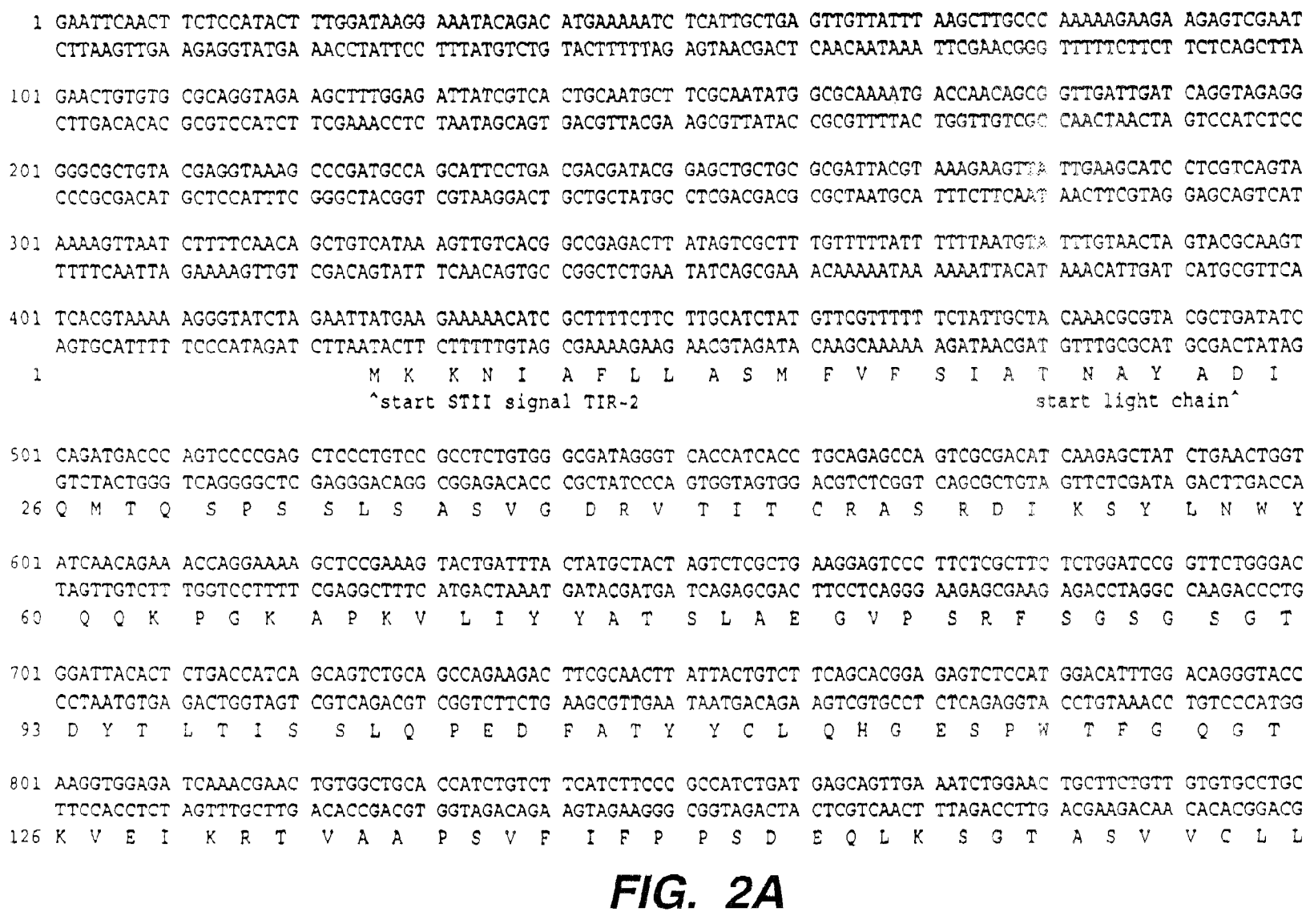

Plasmid pxTF2AP22 is a paTF50 variant comprising the expression cassette nucleotide sequence depicted in FIG. 2 (SEQ ID NOs: 4-6).

Plasmid pxVG2AP11

Figure 3A:
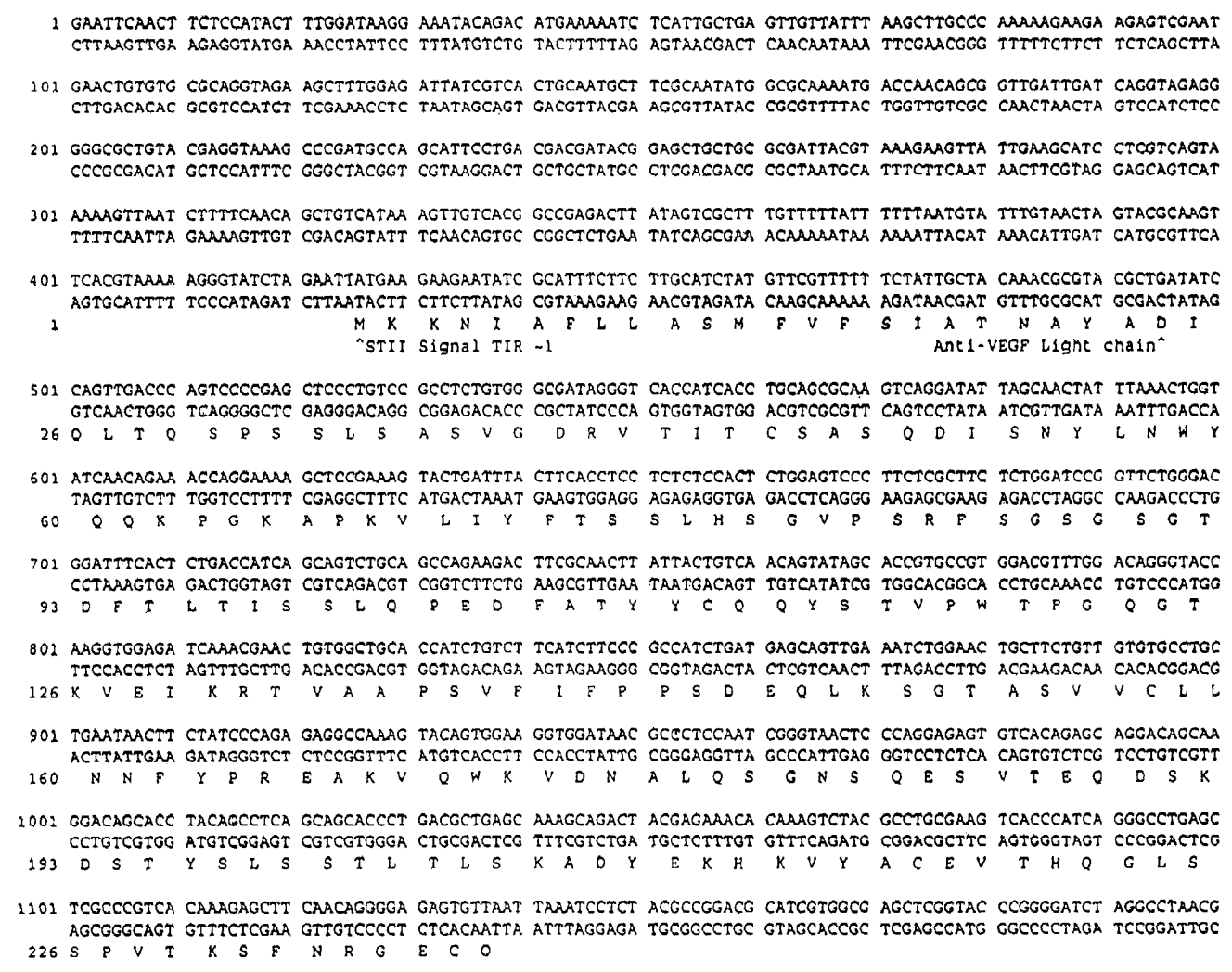
Figure 3B:
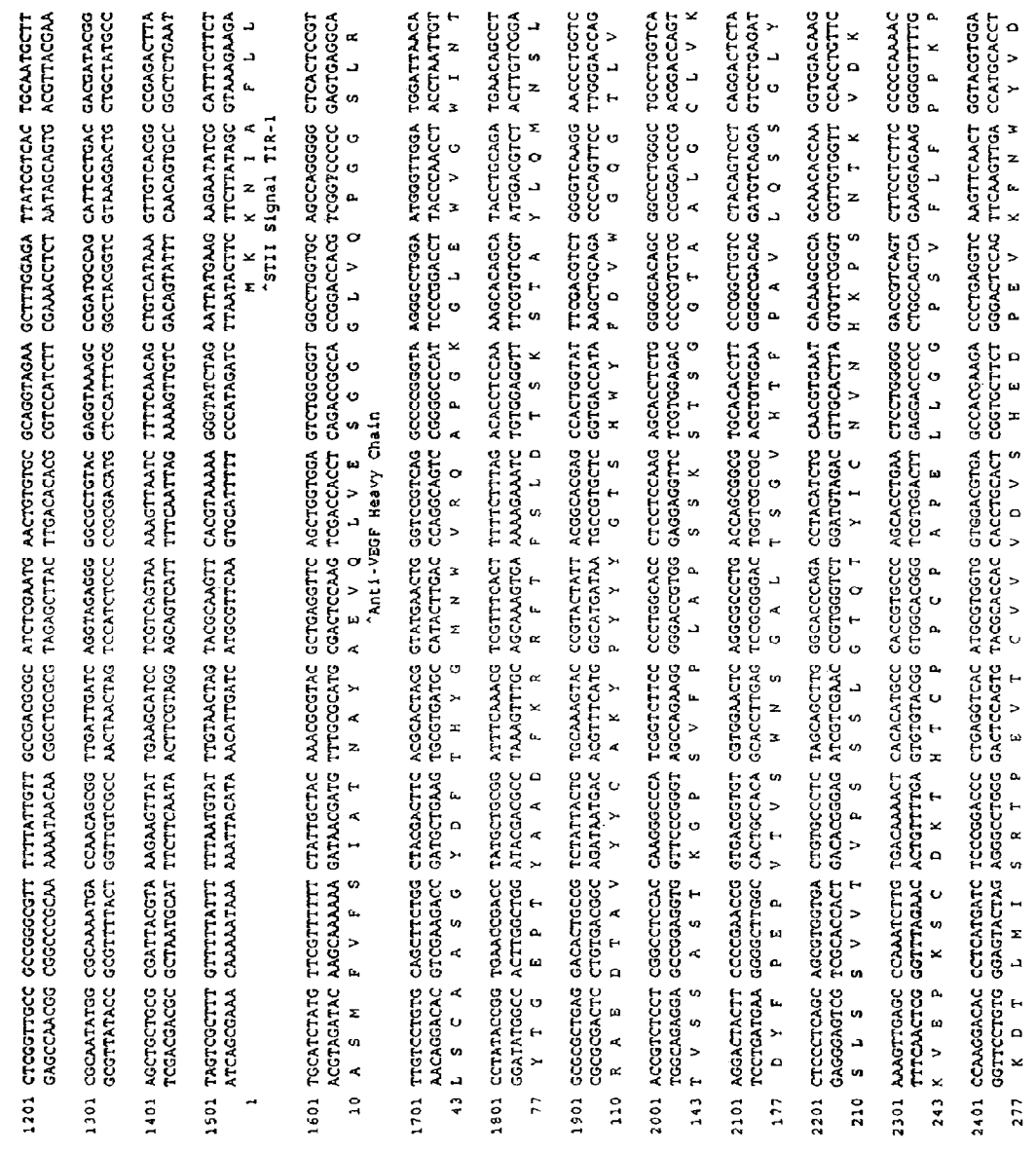

Plasmid pxVG2AP11 was constructed by cloning an expression cassette into the framework of the *E. coli* plasmid pBR322 at the EcoRI site. Sutcliffe (1978) Cold Spring Harbor Symp. Quant. Biol. 43:77-90. The expression cassette sequence of pxVG2AP11 (for anti-VEGF; SEQ ID NOs: 7-9) are provided in FIG. 3.

Plasmid pxVG11VNERK

For the construction of this plasmid, the $V_L$ and $V_H$ regions of paTF50 were replaced with the $V_L$ and $V_H$ of anti-VEGF (VNERK), a higher affinity variant of the humanized antibody described in Presta et al., *Cancer Res.* 57:4593-4599 (1997). The expression cassette nucleotide sequence for this plasmid is depicted in FIG. 4 (SEQ ID NOs: 10-12).

Plasmid pVG27

The plasmid pVG27 is an intermediate in which both hinge cysteines of a Fab-CH2 have been converted to serines, and was constructed by ligating together four DNA fragments. The first DNA fragment was the vector pY0317CH2 in which the ApaI-SphI fragment, encoding amino acids 130-346 of heavy had been removed. The plasmid pY0317CH2 is a derivative of the vector pAK19 (Carter et al., *Bio/Technology* 10:12-16, 1992) in which the variable domaines for light and heavy chains have been replaced with those for an anti-VEGF antibody Y0317 (Chen et al., *J. Mol. Biol.* 293:865-881, 1999). Additionally pY0317CH2 contains the CH2 domain of a human IgG1. The second part in the ligation was an approximately 279-base pair ApaI-BanII fragment from pY0317(Chen et al., *J. Mol. Biol.* 293:865-881, 1999). The third part in the ligation was a BanII-AlwNI synthetic DNA duplex with the following sequence covering the hinge region:

(SEQ ID NO: 22)
5'-CAAATCTTGTGACAAAACTCACACTAGTCCACCGTCTCCAGCAC (SEQ ID NO: 23)
TCGGGTTTAGAACACTGTTTTGAGTGTGATCAGGTGGCAGAGGTC-5'

The final part was an AlwNI-SphI fragment from pY0317CH2 encoding amino acids 238-346.

Plasmid paTF180

The plasmid paTF180 was designed to express a full-length anti-tissue factor antibody in which both hinge cysteines have been converted to serines, and was constructed by ligating together two pieces of DNA. The first part was the vector paTF50 in which the approximately 505 base-pair ApaI-SacII fragment had been removed. The second was a 505 base-pair ApaI-SacII fragment from pVG27 containing the converted hinge region.

Plasmid pVG60

The plasmid pVG60 was designed to express a full-length anti-VEGF antibody (VNERK) in which both hinge cysteines have been converted to serines, and was constructed by ligating together two DNA pieces. The first part was the vector pxVG11VNERK in which the 505 base-pair ApaI-SacII fragment had been removed. The second was a 505 base-pair ApaI-SacII fragment from pVG27 containing the converted hinge region.

Plasmid pVG80

The plasmid pVG80 was designed to express a full-length anti-VEGF antibody (Y0317) in which both hinge cysteines have been converted to serines, and was constructed by ligating together two DNA pieces. The first part was the vector pxVG2AP11 in which the 505 base-pair ApaI-SacII fragment had been removed. The second was a 505 base-pair ApaI-SacII fragment from pVG27 containing the converted hinge region.

Plasmid paTF258

The plasmid paTF258 was designed to express a full-length anti-tissue factor antibody in which the second hinge cysteine had been converted to a serine, and was constructed by ligating together four DNA pieces. The first of these was the vector paTF50 in which the 505 base-pair ApaI-SacII fragment had been removed. The second was a 306 base-pair ApaI-NspI fragment from paTF50 encoding most of the CH1 domain up to the hinge region. The third piece was a 63 base-pair NspI-StyI synthetic DNA duplex with the following sequence:

(SEQ ID NO: 24)
5'-CCCACCGTCGCCGGCACCTGAACTCCTGGGGGGACCGTCAGTCTTCC
TCTTCCCCCCAAAACC (SEQ ID NO: 25)
GTACGGGTGGCAGCGGCCGTGGACTTGAGGACCCCCCTGCAGTCAGAAGG
AGAAGGGGGGTTTTGGGTTC-5'

The last piece was a 128 base-pair StyI-SacII fragment from paTF50 encoding part of the CH2 domain. The last two pieces were preligated and purified on a PAG prior to ligating with the first two parts.

Plasmid pVG126

The plasmid pVG126 was designed to express a full-length anti-VEGF(VNERK) antibody in which the second hinge cysteine had been converted to a serine, and was constructed by ligating together four DNA pieces. The first of these was the vector pxVG11VNERK in which the 505 base-pair ApaI-SacII fragment had been removed. The second was a 306 base-pair ApaI-NspI fragment from paTF50 encoding most of the CH1 domain up to the hinge region. The third piece was a 63 base-pair NspI-StyI synthetic DNA duplex with the following sequence:

(SEQ ID NO: 26)
5'-CCCACCGTCGCCGGCACCTGAACTCCTGGGGGGACCGTCAGTCTTCC
TCTTCCCCCCAAAACC (SEQ ID NO: 27)
GTACGGGTGGCAGCGGCCGTGGACTTGAGGACCCCCCGCTGGCAGTCAGA
AGGAGAAGGGGGGTTTTGGGTTC-5'

The last piece was a 128 base-pair StyI-SacII fragment from paTF50 encoding part of the CH2 domain. The last two pieces were preligated and purified on a PAG prior to ligating with the first two parts.

Plasmid 12aTF262

The plasmid paTF262 was designed to express a full-length anti-tissue factor antibody in which the first hinge cysteine had been converted to a serine, and was constructed by ligating together four DNA pieces. The first of these was the vector paTF50 in which the 505 base-pair ApaI-SacII fragment had been removed. The second was a 306 base-pair ApaI-SpeI fragment from paTF180 encoding most of the CH1 domain up to the hinge region. The third was a 63 base-pair synthetic DNA duplex with the following sequence:

(SEQ ID NO: 28)
5'-CTAGTCCACCGTGCCCAGCACCTGAACTCCTGGGGGACCGTCAGTCT
TCCTCTTCCCCCCAAAACC (SEQ ID NO: 29)
AGGTGGCACGGGTCGTGGACTTGAGGACCCCCCTGGCAGTCAGAAGGAGA
AGGGGGGTTTTGGGTTC-5'

The last piece was a 128 base-pair StyI-SacII fragment from paTF50 encoding part of the CH2 domain. The last two pieces were preligated and purified on a PAG prior to ligating with the first two parts.

Plasmid pVG136

The plasmid pVG136 was designed to express a full-length anti-VEGF (VNERK) antibody in which the first hinge cysteine had been converted to a serine, and was constructed by ligating together four DNA pieces. The first of these was the vector pxVG11VNERK in which the 505 base-pair ApaI-SacII fragment had been removed. The second was a 306 base-pair ApaI-SpeI fragment from paTF180 encoding most of the CH1 domain up to the hinge region. The third was a 63 base-pair synthetic DNA duplex with the following sequence:

(SEQ ID NO: 30)
5'-CTAGTCCACCGTGCCCAGCACCTGAACTCCTGGGGGGACCGTCAGTC
TTCCTCTTCCCCCCAAAACC (SEQ ID NO: 31)
AGGTGGCACGGGTCGTGGACTTGAGGACCCCCCTGGCAGTCAGAAGGAGA
AGGGGGGTTTTGGGTTC-5'

The last piece was a 128 base-pair StyI-SacII fragment from paTF50 encoding part of the CH2 domain. The last two pieces were preligated and purified on a PAG prior to ligating with the first two parts.

Plasmid paTF320

The plasmid paTF320 was designed to express a full-length anti-tissue factor antibody in which both hinge cysteines have been converted to serines. It was constructed by ligating together two pieces of DNA, the first of which was the vector paTF2AP22 in which the 505 base-pair ApaI-SacII fragment had been removed. The second part was a 505 base-pair ApaI-SacII fragment from pVG27 encoding the hinge region in which both cysteines had been converted to serines.

Plasmid pVG110

The plasmid pVG110 was designed to express a full-length anti-VEGF(VNERK) antibody in which both hinge cysteines had been converted to serines. It was constructed by ligating together two pieces of DNA, the first of which was the vector pVNERK-22 in which the 505 base-pair ApaI-SacII fragment had been removed. The second part was a 505 base-pair ApaI-SacII fragment from pVG27 encoding the hinge region in which both cysteines had been converted to serines.

Plasmid pVNERK-22

The plasmid pVNERK-22 was designed to express a full-length anti-VEGF(VNERK) antibody. It was constructed by ligating together four pieces of DNA, the first of which was the vector pSTBKPhoA#107 (variant 3 in Simmons and Yansura, *Nature Biotechnol.* 14:629-634, 1996) in which the smaller MluI-BamHI fragment had been removed. The second part was a 605 base-pair MluI-AlwNI fragment from pxVG11VNERK encoding most of light chain. The third was a 547 base-pair AlwNI-BsiWI fragment from pxTF2AP22 encoding the end of light chain, the terminator, the heavy phoA promoter and the heavy STII signal sequence. Finally, the last piece was an 1811 base-pair BsiWI-BamHI fragment from pxVG11VNERK.

Plasmid pY0317H22

The plasmid pY0317H22 was designed to express a full-length anti-VEGF(Y0317) antibody with both hinge cysteines converted to serines. It was constructed by ligating together three DNA pieces, the first of which was the vector pVG110 in which the smaller EcoRI-SacII fragment had been removed. The second part was a 1633 base-pair EcoRI-MluI fragment prepared by digesting pVG110 with EcoRI first, and then partially digesting with MluI. This fragment encodes the phoA promoter and STII signal sequence for light chain, all of light chain, and the phoA promoter and STII signal sequence for heavy chain. The final piece was an 899 base-pair MluI-SacII fragment from pVG80 encoding much of heavy chain including the hinge region.

Plasmid pmFLT10

The plasmid pmFLT10 was designed to express the murine Flt receptor ECD fused to a murine IgG2b Fc, and was constructed by ligating together four DNA fragments. The first was the vector pPho41 in which the smaller MluI-BamHI fragment had been removed. The plasmid pPho41 is the variant 4 construct in Simmons and Yansura, *Nature Biotechnol.* 14:629-634, 1996. The second part in the ligation was a 920 base-pair MluI-ApaI fragment prepared by PCR using the following primers with the plasmid pmsflt123.IgG.pRK as a template (and later digesting with MlUI and ApaI).

```
FLTF
                                        (SEQ ID NO: 32)
5'-TAGCTACAAACGCGTATGCCTCGAAGTTAAAAGTGCCTGAACTG

FLTR
                                        (SEQ ID NO: 33)
5'-GCTGAAATGGGCCCCACATGCACGGAGGTGTTGAAAGA
```

The third part of the ligation was a 711 base-pair ApaI-HindIII fragment from pmsflt123.IgG.pRK, which is a plasmid encoding the murine Flt receptor ECD as well as a murine IgG2b Fc. The fourth part was a 346 base-pair HindIII-BamHI fragment from pBR322. The second and third parts of the ligation were preligated and isolated before being ligated to the first and fourth part.

Plasmid pmFLThg

The plasmid pmFLThg is a derivative of pmFLT10 in which the four hinge cysteines of the Fc fusion have been converted to serines. It was constructed by the ligation of two pieces of DNA, the first of which was the vector pmFLT10 in which the small 66 base-pair ApaI-XhoI fragment had been removed. The second part in the ligation was a 66 base-pair synthetic ApaI-XhoI duplex with the following sequence:

```
                                        (SEQ ID NO: 34)
5'-CATTTCAACAATCAACCCCTCTCCTCCATCCAAGGAGTCTCACAAAT
CTCCAGCTCCTAACC (SEQ ID NO: 35)
CCGGGTAAAGTTGTTAGTTGGGGAGAGGAGGTAGGTTCCTCAGAGTGTTT
AGAGGTCGAGGATTGGAGCT-5'
```

Plasmid pE25-22

The plasmid pE25-22 was designed to express a full-length anti-IgE antibody. It was constructed by ligating together four pieces of DNA, the first of which was the vector pST2HC in which the small MluI-BstEII fragment had been removed. The vector pST2HC is a derivative of variant 3 (Simmons and Yansura, *Nature Biotechnol.* 14:629-634, 1996) in which the phoA gene has been replaced by an anti-tissue factor heavy chain. The second part was 617 base-pair MluI-AlwNI fragment from phumae11v25pA19 encoding most of the light chain for the E25 anti-IgE antibody (the humanized MaE11 IgG1 described in Presta et al., *J. Immunol.* 151:2623-2632, 1993). The third part was a 547 base-pair AlwNI-BsiWI fragment from pxTF2AP22 encoding the end of light chain, the heavy AP promoter and the heavy STII signal sequence. Finally the fourth part in the ligation was a 355 base-pair BsiWI-BstEII fragment from phumae11v25pA19 encoding the beginning of heavy chain.

Plasmid pE25-22CS

The plasmid pE25-22CS is a derivative of pE25-22 in which the two hinge cysteines have been converted to serines, and was constructed by ligating together four pieces of DNA. The first was the vector pBR322 in which the small EcoRI-ClaI fragment had been removed. The second piece was a 1645 base-pair fragment prepaired by digesting pE25-22 with EcoRI first and then partially digesting with MluI. This EcoRI-MluI fragment encodes the light AP promoter, signal sequence, light chain, and the heavy AP promoter and its signal sequence. The third part was a 358 base-pair MluI-BstEII fragment from phumae11v25pA19 (the humanized MaE11 IgG1 described in Presta et al., *J. Immunol.* 151:2623-2632, 1993) encoding the beginning of the heavy chain. The final part was a 1089 base-pair BstEII-ClaI fragment from paTF180 encoding the remainder of heavy chain.

Plasmid pJJ247

To construct pJJ247, the plasmid encoding both dsbA and dsbC, pJJ142 (described in greater detail below) was digested with KpnI and ScaI. DsbC was PCR amplified from plasmid pJJ141 (described in greater detail below) using the following primers:

```
                                        (SEQ ID NO: 36)
tacdsbCf1:  CATACTGGTACCAGGATCTAGAGGGAAGATTTATG (SEQ ID NO: 37)
tacdsbCr2:  CTGGTGAGTACTCAACCAAGTCATTCTG
```

The primers contain restriction sites (KpnI, ScaI) which are underlined. After PCR amplification, the fragment was purified by agarose gel electrophoresis and digested with the appropriate enzymes and ligated to KpnI/ScaI digested pJJ142. The resulting plasmid, pJJ247, encodes a tac promoter driving the expression of both dsbA and dsbC with dsbA first in the series. The plasmid was sequenced from the middle of the dsbA gene through the 3' end of the dsbC gene.

To construct the dsbC plasmid pJJ141, the kanamycin resistant plasmid pACYC177 was digested with AatII and HincII disrupting ampicillin resistance. The tac-dsbC plasmid pJJ40, described in U.S. Pat. No. 5,639,635, was digested with ClaI and then filled in with Klenow and deoxynucleotides. After phenol:chloroform extraction and precipitation, the linearized vector was digested with AatII and the 1.6 kb fragment was purified from an agarose gel and ligated to AatII/HincII digested pACYC177. The final plasmid pJJ141 encodes tac-dsbC and confers kanamycin resistance. Similarly, the dsbA plasmid pJJ142 was constructed using the same AatII/HincII cut parent vector ligated with a AatII/ClaI (filled in ClaI site) fragment from pJJ37, which encodes dsbA and is also described in U.S. Pat. No. 5,639,635.

Plasmid pSD12-2

Figure 5A:
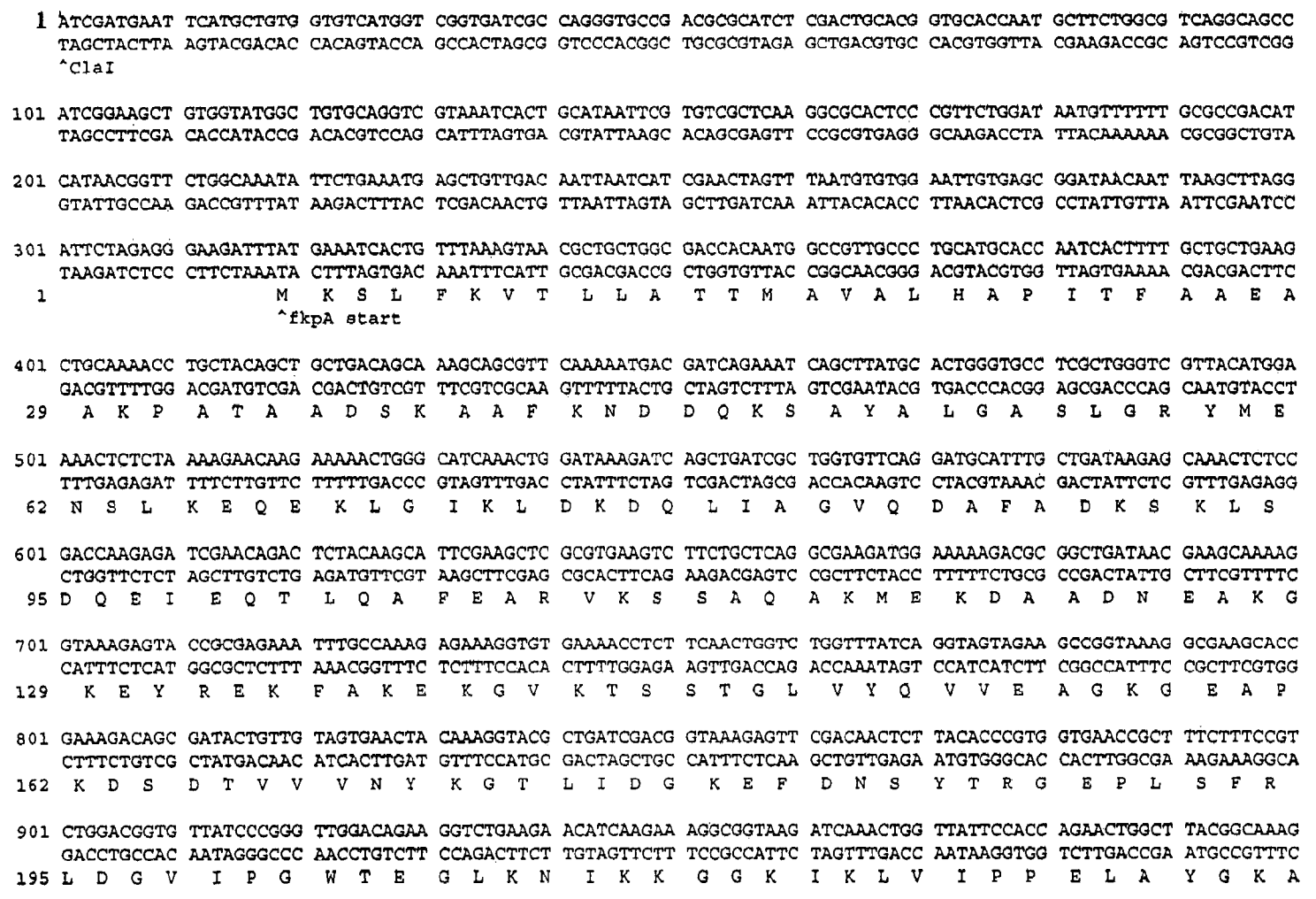

The plasmid pSD12-2 was designed to express a full-length anti-tissue factor antibody with relative TIR strengths of 2 for light and 2 for heavy chain, and additionally express the chaperone fkpA under the control of the tac promoter. It was constructed by ligating together two DNA pieces, the first of which was the vector paTF320 in which the small ClaI-NheI fragment had been removed. The second part in the ligation was a 1133 base-pair ClaI-NheI fragment containing the tac promoter followed by the coding sequence for the chaperone fkpA. The beginning of the fkpA gene has silent codon changes to modulate the expression level of fkpA and the sequence is depicted in FIG. 5 (SEQ ID NOs: 13-15).

Plasmid pxTF7T3FL

Figure 6B:
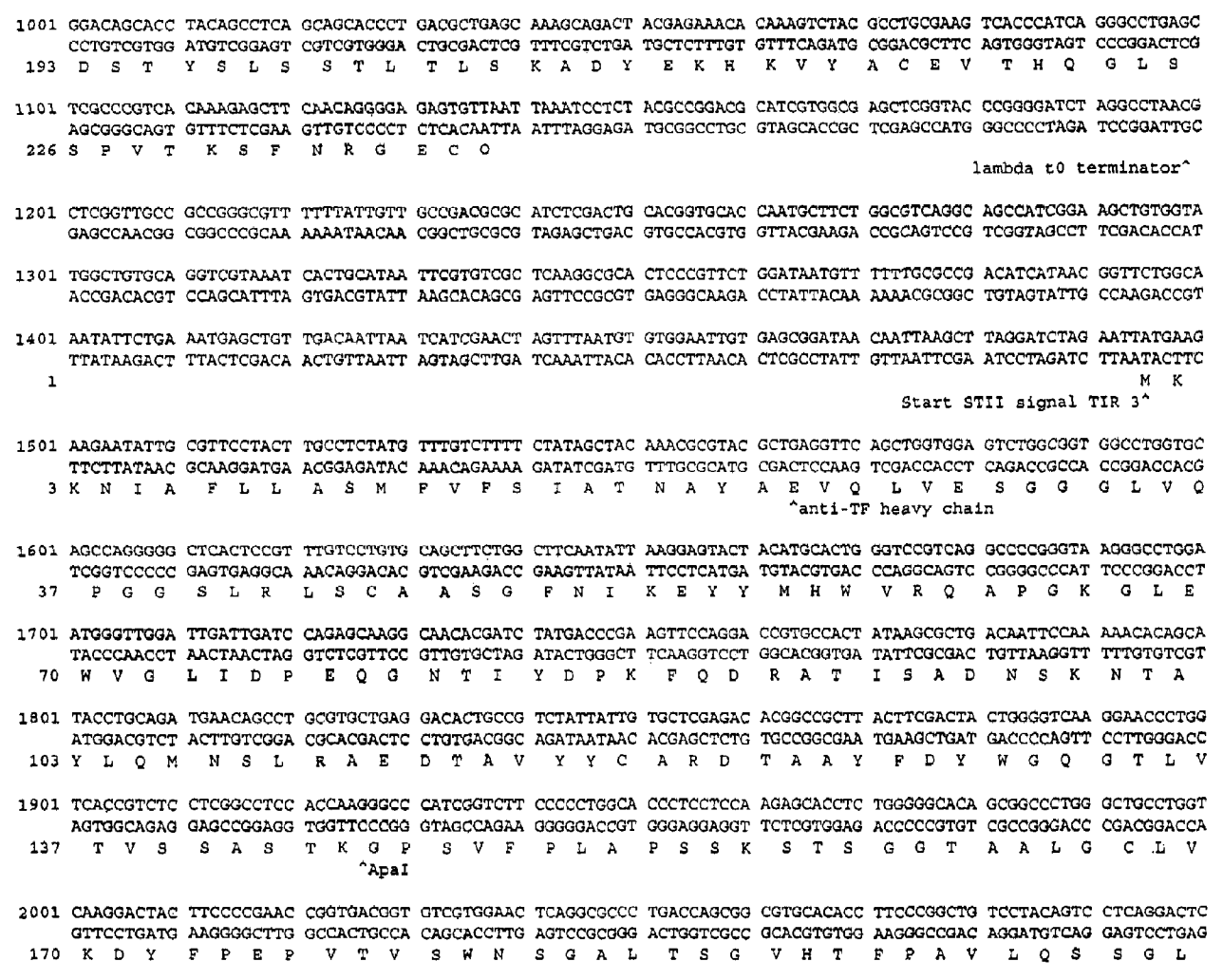
Figure 6C:
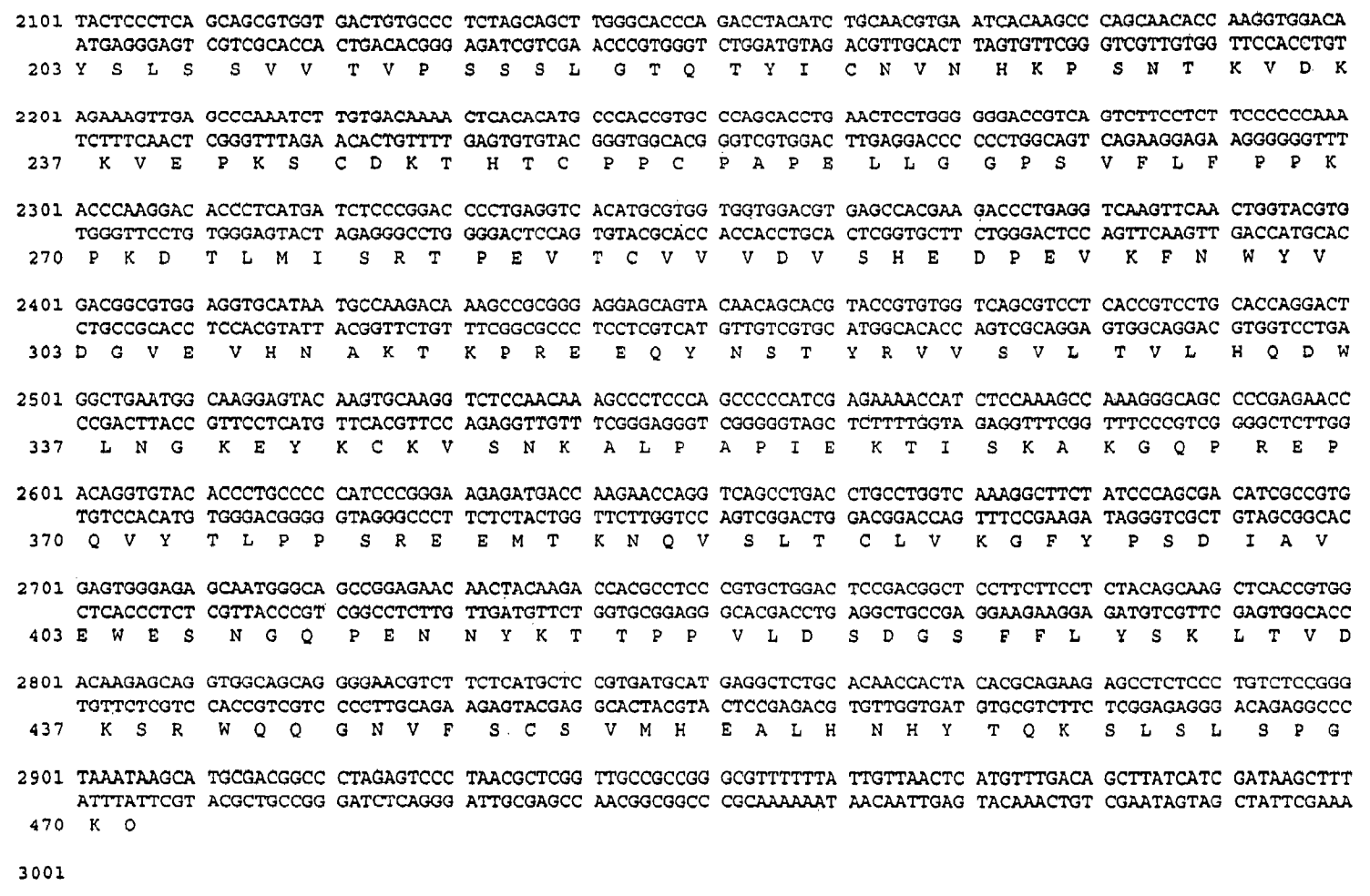

The plasmid pxTF7T3FL was designed to express a full-length anti-tissue factor antibody with the phoA promoter controlling light chain with a TIR strength of 7, and with the tac promoter controlling heavy chain with a TIR strength of 3. It was constructed by ligating together two pieces of DNA, the first of which was the vector paTF20 in which the smaller EcoRI-ApaI fragment had been removed. The plasmid paTF20 was designed to express a full-length anti-tissue factor antibody polycistronically with one phoA promoter and TIR strengths of 1 for light and 1 for heavy, and has been previously described. Simmons et al. *J. Immunol. Methods* 263:133-147 (2002). The second piece in the ligation was an approximately 1926 base-pair EcoRI-ApaI fragment encoding the phoA promoter, light chain, tac promoter, and the first part of heavy chain. The sequence of this fragment including the last part of heavy chain is depicted in FIG. 6 (SEQ ID NOs: 16-18).

Plasmid pxTF7T3H

The plasmid pxTF7T3H is identical to pxTF7T3FL except for the hinge region where both cysteines have been converted to serines. The sequence of the phoA promoter, light chain, tac promoter, and heavy chain is depicted in FIG. 7.(SEQ ID NOs: 19-21).

Example 2

Effects of Conversion of Hinge Cysteines to Serines

The hinge cysteines were chosen as a starting place to identify particular residues, focusing in particular on cysteines, that may be prone to play a role in heavy chain aggregation. In human IgG1s, there are two hinge cysteines that are separated by two prolines, and these are normally paired with their counterparts on an adjacent heavy chain. Each cysteine was converted to serine separately initially, so that the respective effects on aggregation and folding could be observed. Two different antibodies were chosen as candidates for the experiment, an anti-tissue factor antibody (D3H44, Presta et al., *Thromb. Haemost.* 85:379-389 (2001)) and an anti-VEGF antibody (VNERK, a high affinity version of the humanized antibody described in Presta et al., *Cancer Res.* 57:4593-4599 (1997). Constructs were prepared for the first (paTF262) and second (paTF258) cysteine conversions for the anti-tissue factor antibody as well as the first (pVG136) and second (pVG126) cysteines in the hinge region of the anti-VEGF antibody. These constructs had relative translation initiation strengths of 1 for light chain and 1 for heavy chain (Simmons and Yansura, *Nature Biotechnology*, 14:629-634(1996)).

Small-scale inductions of antibodies were carried out using the parent constructs (paTF50 for anti-tissue factor, and pxVG11VNERK for anti-VEGF) as well as the cysteine to serine modified constructs. For small scale expression of each construct, the *E. coli* strain 33D3 (W3110 ΔfhuA (ΔtonA) ptr3 lac Iq lacL8 ΔompTΔ(nmpc-fepE) degP41 kan$^R$) was used as host cells. Following transformation, selected transformant picks were inoculated into 5 ml Luria-Bertani medium supplemented with carbenicillin (50 ug/ml) and grown at 30° C. on a culture wheel overnight. Each culture was then diluted (1:50 or 1:100) into C.R.A.P. phosphate-limiting media (3.57 g (NH4)2SO4, 0.71 g NaCitrate-2H2O, 1.07 g KCl, 5.36 g Yeast Extract (certified), 5.36 g HycaseSF-Sheffield, adjusted pH with KOH to 7.3, qs to 872 ml with SQ H2O and autoclaved; cool to 55° C. and supplemented with 110 ml 1M MOPS pH 7.3, 11 ml 50% glucose, 7 ml 1M MgSO4). Carbenicillin was then added to the induction culture at a concentration of 50 ug/ml and the culture was grown for approximately 24 hours at 30° C. on a culture wheel. Unless otherwise noted, all shake flask inductions were performed in a 2 ml volume.

Non-reduced whole cell lysates from induced cultures were prepared as follows: (1) 1 $OD_{600}$-ml pellets were centrifuged in a microfuge tube; (2) each pellet was resuspended in 90 ul TE (10 mM Tris pH 7.6, 1 mM EDTA); (3) 10 ul of 100 mM iodoacetic acid (Sigma I-2512) was added to each sample to block any free cysteines and prevent disulfide shuffling; (4) 20 ul of 10% SDS was added to each sample. The samples were vortexed, heated to about 90° C. for ~3 minutes and then vortexed again. After the samples had cooled to room temperature, ~750-1000 ul acetone was added to precipitate the protein. The samples were vortexed and left at room temperature for about 15 minutes. Following centrifugation for 5 minutes in a microcentrifuge, the supernatant of each sample was aspirated off and each protein pellet was resuspended in 50 ul $dH_2O$+50 ul 2× NOVEX sample buffer. The samples were then heated for ~3-5 minutes at about 90° C., vortexed well and allowed to cool to room temperature. A final 5 minute centrifugation was then done and the supernatants were transferred to clean tubes.

Following preparation, 5-10 ul of each sample was loaded onto a 10 well, 1.0 mm NOVEX manufactured 12% Tris-Glycine SDS-PAGE and electrophoresed at ~120 volts for 1.5-2 hours. The resulting gels were then either stained with Coomassie Blue or used for Western blot analysis.

For Western blot analysis, the SDS-PAGE gels were electroblotted onto a nitrocellulose membrane (NOVEX). The membrane was then blocked using a solution of 1× NET (150 mM NaCl, 5 mM EDTA, 50 mM Tris pH 7.4, 0.05% Triton X-100)+0.5% gelatin for approximately 30 min.-1 hour rocking at room temperature. Following the blocking step, the membrane was placed in a solution of 1×NET+0.5% gelatin+anti-Fab antibody (peroxidase-conjugated goat IgG fraction to human IgG Fab; CAPPEL #55223). The anti-Fab antibody dilution ranged from 1:50,000 to 1:1,000,000 depending on the lot of antibody. The membrane was left in the antibody solution overnight at room temperature with rocking. The next morning, the membrane was washed a minimum of 3×10 minutes in 1× NET+0.5% gelatin and then 1×15 minutes in TBS (20 mM Tris pH 7.5, 500 mM NaCl). The protein bands bound by the anti-Fab antibody were visualized by using Amersham Pharmacia Biotech ECL detection and exposing the membrane to X-Ray film.

Figure 8A:
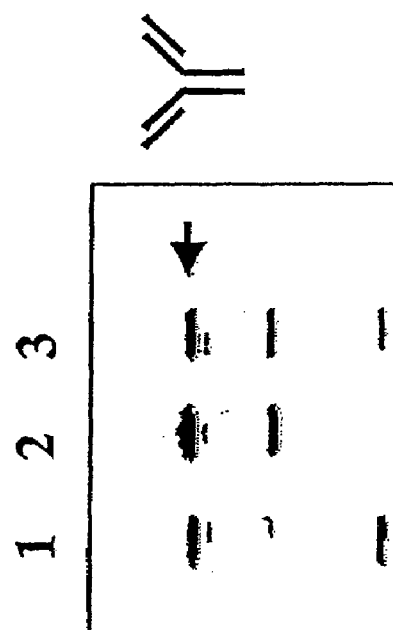

The results are shown in FIG. 8, and they reveal that there was a noticeable increase in the fully folded and assembled full-length antibody for any of the new constructs. Conversion of any one of the cysteines at the hinge region to serine for either antibody therefore resulted in a noticeable and measurable shift from aggregated heavy chain to the folded heavy chain in the completed tetrameric molecule.

Conversion of Both Hinge Cysteines

Figure 9:
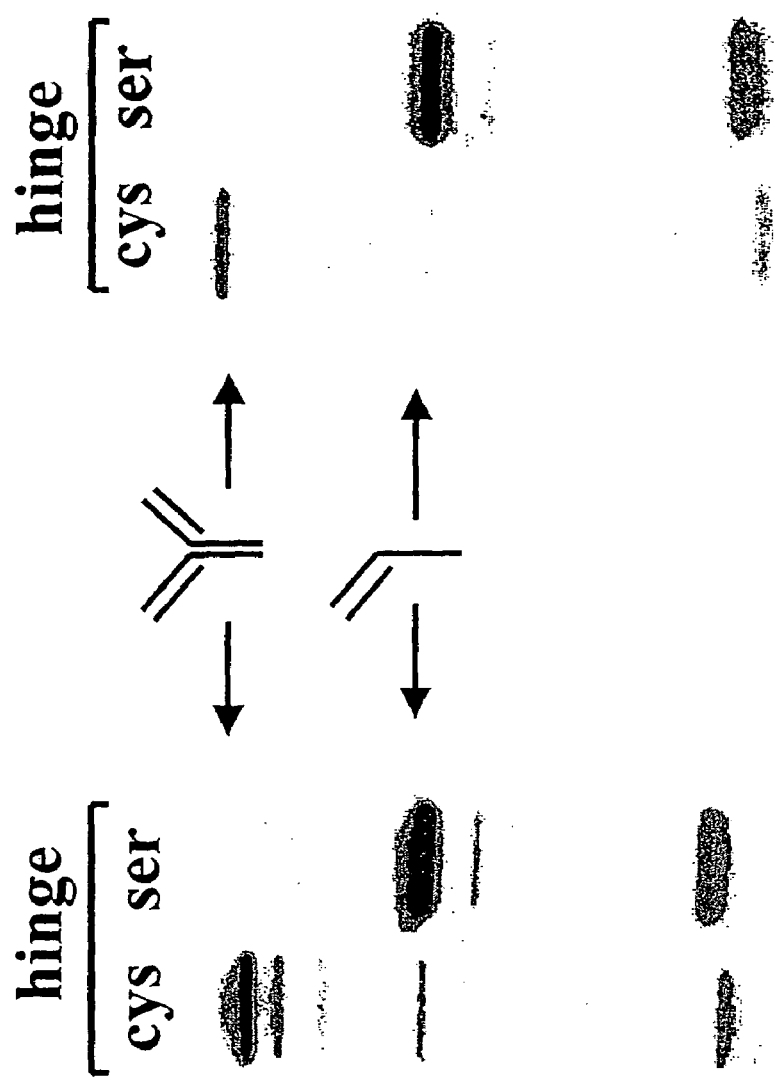
FIG. 9 shows western blot analyses for the conversion of both hinge cysteines to serines for the anti-tissue factor full-length antibody as well as the anti-VEGF VNERK full-length antibody. The "cys" lanes refer to products with the original wild type hinge sequence, and the "ser" lanes refer to products with the hinge regions where both cysteines have been converted to serines. The top arrows point to the heavy-heavy-light-light species, while the lower arrows point to the half-antibody heavy-light species.

The hinge cysteines were then both changed to serines at the same time in both the anti-tissue factor (paTF180) as well as the anti-VEGF (pVG60) antibody constructs. Antibody expression was then again induced using these plasmids as previously described. Whole cell lysates were prepared, separated by SDS-PAGE, transferred onto nitrocellulose, and detected with the previously described goat anti-human Fab conjugated antibody. The results as shown in FIG. 9 indicate that this time there was an even more dramatic increase in heavy chain folding and assembly when both hinge cysteines were replaced at the same time. As expected, the maximum observable size on an SDS-PAGE gel (which is denaturing) for antibodies with both hinge cysteines replaced with serines is a half structure where one heavy chain and one light chain are covalently attached to each other by a disulfide bond.

Conversion of Both Hinge Cysteines for an Additional Antibody

Figure 10:
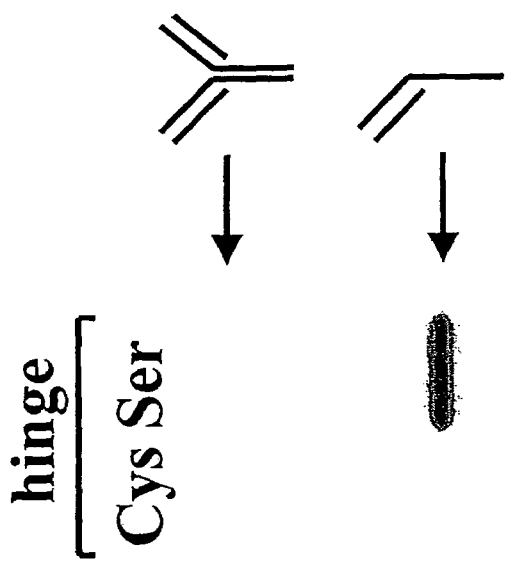
FIG. 10 shows a western blot analysis for the conversion of both hinge cysteines to serines for the anti-VEGF Y0317 full-length antibody. The "cys" lane refers to products obtained with the construct with original wild type hinge, while the ser lane refers to products obtained with the construct where both hinge cysteines were converted to serines. The top arrow points to the heavy-heavy-light-light species, which is a very faint band in the "cys" lane, while the lower arrow points to the half-antibody heavy-light species.

To further confirm the results observed for the two previous antibodies, an additional candidate antibody was tested. Another anti-VEGF antibody (YO317, Chen et al., *J. Mol. Biol.*, 293:865-881 (1999)) with lower levels of expression than the two previous antibodies, was modified to replace both hinge cysteines with serines. The parent (pxVG2AP11) and the cysteine to serine modified version (pVG80) were then expressed in the same manner as previously described. Whole cell lysates were prepared, separated by SDS-PAGE, transferred to nitrocellulose, and detected with the previously described goat anti-human Fab conjugated antibody. The results, as shown in FIG. 10, show a significant improvement in folding and assembly of this antibody as seen by the intense band for the half structure detected in the presence of SDS.

Fc Fusions with Hinge Cysteines Replaced by Serines

Figure 11:
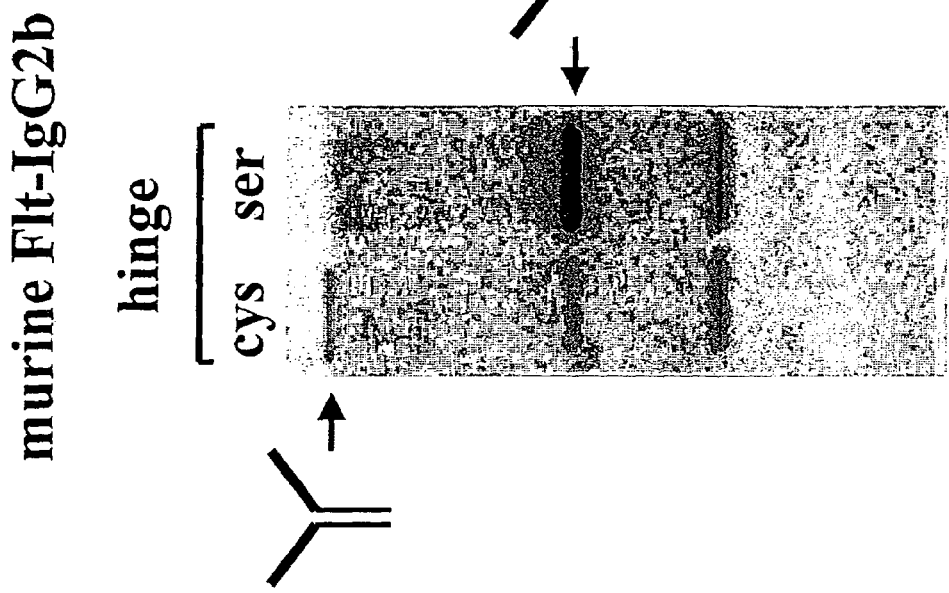
FIG. 11 shows a western blot analysis for the conversion of all four hinge cysteines of the murine Flt-IgG2b Fc fusion to serines. The "cys" lane reflects products obtained with the construct for wild type murine Fc hinge, while the "ser" lane reflects products obtained with the construct with all four cysteines converted to serines. The top arrow points to the covalent dimer Fc fusion, while the lower arrow points to the half or monomer Fc fusion.

The involvement of cysteines, in particular hinge cysteines, in aggregation of antibody fragments was also examined. An Fc fusion was tested. Fc fusions are essentially antibodies in which the Fab regions have been replaced with an alternative protein of interest. In order to test this idea, a murine Flt-IgG2b construct was altered to convert all four hinge cysteines to serines. This Fc fusion comprises the murine Flt receptor (murine version of the human, Peters et al., *Proc. Natl. Acad. USA*, 90:8915-8919 (1993)) extracellular domain fused at the hinge region to a murine IgG2b Fc fragment with four disulfides at the hinge. Using the parent plasmid (plasmid pmFLT10) and the cysteine to serine converted construct (plasmid pmFLTmg), these Fc fusions were expressed in *E.coli* as described above. Whole cell lysates were separated by SDS-PAGE, transferred to nitrocellulose, and Fc fragments detected with an anti-murine IgG2b peroxidase-conjugated antibody. The results are shown in FIG. 11, and they strongly support the idea that the conversion of the hinge cysteines to another amino acid such as serine, results in less aggregation and more Fc fusion folding. As expected, only a half structure could be detected on an SDS PAGE gel due to the denaturing conditions.

Example 3

10 Liter Fermentation Experiments with Hinge Cysteine Mutants

The organisms used for these fermentations include: 33D3 W3110 ΔfhuA (ΔtonA) ptr3 lac Iq lacL8 ΔompTΔ(nmpc-fepE) degP41 kan$^R$; 61D6 W3110 ΔfhuA (ΔtonA) ptr3 lac Iq lacL8 ΔompTA(nmpc-fepE) degP41; and 62A7 W3110 ΔfhuA (ΔtonA) ptr3 lac Iq lacL8 ΔompTΔ(nmpc-fepE) degP41 ilvG repaired.

For each 10-liter fermentation, 0.5 mL of frozen stock culture (containing 10-15% DMSO) was thawed into a 2L shake flask containing 500 ml of LB medium supplemented with either 0.5 ml of tetracycline solution (5 mg/ml) or 10 mL of ampicillin solution (2 mg/mL) and 2.5 ml 1M sodium phosphate solution. This seed culture was grown for approximately 16 hours at 30° C. with shaking and was then used to inoculate the 10-liter fermentor.

The fermentor initially contained approximately 7.0 liters of medium containing 1.1 g of glucose, 100 ml of 1M magnesium sulfate, 10 ml of a trace element solution (100 ml hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, 5 g manganese-sulfate monohydrate, in a final volume of 1 liter), either 20 ml of a tetracycline solution (5 mg/ml in ethanol) or 250 mL of an ampicillin solution (2 mg/mL), 1 bag of HCD salts, (37.5 g ammonium sulfate, 19.5 g potassium phosphate dibasic, 9.75 g sodium phosphate monobasic dihydrate, 7.5 g sodium citrate dihydrate, 11.3 g potassium phosphate monobasic), 200 g of NZ Amine A (a protein hydrolysate), and 100 grams of Yeast Extract. Fermentations were performed at 30° C. with 20 slpm of air flow and were controlled at a pH of 7.0±0.2 (although occasional excursions beyond this range occurred in some cases). The back pressure of the fermentor was maintained at 1 bar gauge and the agitation rate was set to 650 rpm. The back pressure of the fermentor and agitation rate can also be varied to manipulate the oxygen transfer rate in the fermentor, and, consequently, control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Additions of L-61 (an antifoam—others can be used) were also used in some cases to control foaming. When the culture reached a cell density of approximately 40 OD550, an additional 100 ml of 1M magnesium sulfate was added to the fermentor. Additionally, a concentrated salt feed (12.5 g ammonium sulfate, 32.5 g potassium phosphate dibasic, 16.25 g sodium phosphate monobasic dihydrate, 2.5 g sodium citrate dihydrate, 18.75 g potassium phosphate monobasic, 10 ml of 2.7% ferric chloride and 10 ml of trace elements in a fmal volume of 1250 ml) to the fermentor was started at a rate of 2.5 ml/min when the culture reached approximately 20 OD550 and continued until approximately 1250 ml were added to the fermentation. Fermentations were typically continued for 70-80 hours. During the fermentation, once the dissolved oxygen setpoint for the fermentation was reached, the concentrated glucose solution was fed based on the dissolved oxygen probe signal in order to control the dissolved oxygen concentration at the setpoint. Consequently, in this control scheme, manipulations of fermentor operating parameters such as the agitation rate or back pressure which affect the oxygen transfer capacity in the fermentation correspondingly also manipulated the oxygen uptake rate or metabolic rate of the cells. A mass spectrometer was used to monitor the composition of the off-gas from the fermentations and enable the calculation of the oxygen uptake and-carbon dioxide evolution rates in the fermentations.

Non-reduced soluble samples were prepared as follows: frozen, 1 mL whole broth samples taken during the course of the fermentation were thawed at room temperature. 100 μL of the thawed whole broth was added to 300-500 μL of extraction buffer. (Extraction buffer: 10 mM Tris, pH 6.8, 5 mM EDTA, freshly added 0.2 mg/1 mL of hen egg lysozyme, and freshly prepared iodoacetic acid (IAA) to a final concentration of 5-10 mM.) The whole broth samples plus extraction buffer were incubated on ice for 5-10 minutes, then sonicated 2×10 pulses, then centrifuged at 4 C and 14,000 rpm for 15-20 minutes. Alternatively, non-reduced soluble samples were prepared by taking 200 μL of the thawed whole broth and adding 400 μL of CelLytic™ B-II (Sigma-Aldrich) extraction buffer containing 5-10 mM of IAA. The whole broth samples and the CelLytic™ B-II extraction buffer with IAA were incubated with gentle shaking at room temperature for 30 to 60 minutes, then centrifuged to clarify the supernatant.

Samples of the soluble fractions were submitted for analysis by an AME5-RP assay (described in Battersby, J. E., et. al, J. of Chromatography A, 927: 61-76, 2001). This assay is a dual column HPLC assay where the first column is an affinity column that captures light chain and the second column is a reversed-phase column. An Integral Workstation was configured in the dual column mode. The solvent reservoirs were: Solvent 1A, affinity loading buffer; Solvent 1B, reversed-phase aqueous buffer and affinity elution buffer, 0.1% TFA in water; Solvent 2A, water; Solvent 2B, reversed-phase organic elution buffer, 0.09% TFA/80% acetonitrile. The first column was the affinity column (30×2.1 mm) containing the immobilized anti-light-chain (kappa) Fab antibody (AME5) immobilized on controlled pore glass. All procedures involving the affinity column were performed at ambient temperature. The second column was the reversed-phase column containing the polymer based POROS R220 packing material (30×2.1 mm). The reversed-phase column temperature was maintained at 60° C.

The affinity column was equilibrated in 30% loading buffer (5 ml) and a 50 μl sample was loaded at a flow rate of 0.1 ml/min. The flow-through was directed to waste. After the sample was loaded the affinity column was washed with 30% loading buffer (2 ml), followed by 100% loading buffer (5 ml) to reduce non-specifically bound components. A final wash with water prepared the affinity column for elution (3 ml). The affinity column was now connected to the reversed-phase column (by valve switching) and eluted with elution buffer (2 ml) at a flow rate of 2 ml/min to transfer the affinity-captured components to the reversed phase column. During this transfer step the Integral IV detector is located after the affinity column and before the reversed-phase column and hence monitors the elution of the affinity column (which becomes the load to the reversed-phase column). In addition to this detector, a second detector was added after the reversed-phase column to monitor its flow-through to confirm that all the components eluted from the affinity column were in fact captured by the reversed-phase column.

Re-equilibration of the affinity column was subsequently performed with loading buffer (4 ml) after removing its connection to the reversed-phase column.

The loaded reversed-phase column was washed with aqueous 0.1% TFA (2 ml). The flow rate was set to 1 ml/min and a rapid gradient (1 min) was run to 35% solvent 2B (0.09% TFA/80% acetonitrile) followed by a shallow gradient to 50% solvent 2B over 14 min. Elution is completed by a gradient to 90% solvent 2B over 4 min. The reversed phase column was then returned to initial conditions over 1 min. and re-equilibrated for 3 min at 2 ml/min. The column eluate was monitored at 280 and 214 nm. Quantitation was performed by comparison of the integrated peak areas with those of standards of known concentrations.

Fractions (0.25 μl) were collected across the gradient profile, pooled as appropriate and lyophilized. Peak fractions were partially characterized using the usual procedures employed in N-terminal sequence analysis, and SDS-PAGE analysis. They were also analyzed by liquid chromatography/mass spectrometry (LC/MS). N-terminal sequence analysis, LC/MS, and SDS-PAGE revealed that Peak 5 on the chromatogram contained predominantly full-length antibodies in the tetrameric form (i.e., two light chains and two heavy chains). Due to the denaturing nature of the AME5-RP assay, when samples contained antibody with both hinge cysteines mutated to serine, little to no detectable Peak 5 was seen. Instead, these antibodies ran as Peak 4 on the chromatogram.

Fermentations were done with the following αTF plasmids: paTF50 (hinge cysteines); pxTF2AP22 (hinge cysteines); paTF180 (hinge cysteines mutated to serines); and paTF320 (hinge cysteines mutated to serines).

TABLE 2

| Plasmid | TIR (LC, HC) | Hinge Cysteines | E. coli host | AME5-RP, mg/L |
|---|---|---|---|---|
| paTF50 | 1, 1 | yes | 61D6 | 127 |
| paTF180 | 1, 1 | no | 33D3 | 197 |
| pxTF2AP22 | 2, 2 | yes | 61D6 | 118 |
| paTF320 | 2, 2 | no | 61D6 | 650 |

As can be seen from the data in Table 2, mutating the hinge cysteines to serines results in increased fermentation titers for the αTF antibody as determined by the AME5-RP assay.

Additional fermentations were done with two different αVegF antibodies to determine if a similar result could be obtained. In one set of fermentation experiments, the following αVegF (VNERK variant as noted above) plasmids were used: pVG11VNERK (hinge cysteines); pVNERK22 (hinge cysteines); pVG60 (hinge cysteines mutated to serines); and pVG110 (hinge cysteines mutated to serines).

TABLE 3

| Plasmid | TIR (LC, HC) | Hinge Cysteines | E. coli host | AME5-RP, mg/L |
|---|---|---|---|---|
| pVG11VNERK | 1, 1 | yes | 61D6 | 53 |
| pVG60 | 1, 1 | no | 33D3 | 88 |
| pVNERK22 | 2, 2 | yes | 33D3 | 24 |
| pVG110 | 2, 2 | no | 61D6 | 180 |

In another set of fermentation experiments, the following αVegF (Y0317 variant as described above) plasmids were used: pxVG2AP11 (hinge cysteines); pVG80 (hinge cysteines mutated to serines); and pY0317H22 (hinge cysteines mutated to serines).

TABLE 4

| Plasmid | TIR (LC, HC) | Hinge Cysteines | E. coli host | AME5-RP, mg/L |
|---|---|---|---|---|
| pxVG2AP11 | 1, 1 | yes | 61D6 | 8 |
| pVG80 | 1, 1 | no | 61D6 | 40 |
| pY0317H22 | 2, 2 | no | 61D6 | 224 |

An additional set of fermentation experiments was done with a pair of αIgE (E25) plasmids. The following plasmids were used: pE25-22 (hinge cysteines); and pE25-22CS (hinge cysteines mutated to serines).

TABLE 5

| Plasmid | TIR (LC, HC) | Hinge Cysteines | E. coli host | AME5-RP, mg/L |
|---|---|---|---|---|
| pE25-22 | 2, 2 | yes | 62A7 | 59 |
| pE25-22CS | 2, 2 | no | 62A7 | 300 |

Fermentations were also done with a set of plasmids encoding αTF where the expression of light chain was under the control of the alkaline phosphatase promoter and the expression of heavy chain was under the control of the tacII promoter. Fermentations were conducted as described above except that isopropyl β-D thiogalactopyranoside (IPTG) was added to the culture 40-55 hours after inoculation to give a final concentration of 0.5-2.0 mM. The following plasmids were used: pxTF7T3FL (hinge cysteines) and pxTF7T3H (hinge cysteines mutated to serines).

TABLE 6

| Plasmid | TIR (LC, HC) | Hinge Cysteines | E. coli host | AME5-RP, mg/L |
|---|---|---|---|---|
| pxTF7T3FL | 7, 3 | yes | 61D6 | 47 |
| pxTF7T3H | 7, 3 | no | 61D6 | 357 |

In all of the cases shown above, mutating the hinge cysteines to serines resulted in increased fermentation titers.

Example 4

Co-Expression of Dsb Proteins and Hinge Cysteine Mutants in E. coli

The organism used for these fermentations was 61D6 W3110 ΔfhuA (ΔtonA) ptr3 lac Iq lacL8 ΔompTΔ(nmpc-fepE) degP41.

A plasmid encoding anti-Tissue Factor and with the hinge cysteines mutated to serines (paTF320) was used to transform competent cells of the above organism. A plasmid encoding both dsbA and dsbC under the control of the tacII promoter (pJJ247) was co-transformed with the anti-Tissue Factor plasmid in some cases. When both the anti-Tissue Factor plasmid and the dsbA/dsbC plasmid were used together to transform competent cells, transformants were plated on LB agar plates containing 50 µg/mL of both carbenicillin and kanamycin.

Fermentations were done at the 10-liter scale as described in Example 3. When fermentations were done with the cultures that had both the paTF320 and the pJJ247 plasmid present, 50 mL of a 200 mM solution of isopropyl β-D-thiogalactopyranoside (IPTG) was added to the fermentation culture when the OD550 reached 150-200. Note, however, that IPTG additions can be made at times other than the one described and different amounts of IPTG than described can also be added. Soluble samples were prepared and submitted to the AME5-RP assay as described in Example 3.

As seen in Table 2, the fermentation with the plasmid paTF320 alone resulted in an AME5-RP titer of 650 mg/L. When the cells were co-transformed with both the plasmid paTF320 and the plasmid pJJ247 and grown in a 10 liter fermentation culture, the resulting AME5-RP titer was 1330 mg/L. Thus, co-expressing both dsbA and dsbC with an antibody mutant with respect to hinge cysteines can result in increased fermentation titers.

Example 5

Co-Expression of FkpA and Hinge Cysteine Mutants in E. coli

The organism used for these fermentations was 61D6 W3110 ΔfhuA (ΔtonA) ptr3 lac Iq lacL8 ΔompTΔ(nmpc-fepE) degP41.

A plasmid encoding anti-Tissue Factor with the hinge cysteines mutated to serines (paTF320) was used to transform competent cells of the above organism. Plasmid pSD12-2, encoding both anti-Tissue Factor and fkpA, was also used to tranform competent cells of 61D6. This plasmid encodes both anti-Tissue Factor (hinge cysteines mutated to serines) under the control of alkaline phosphatase promoters and fkpA under the control of the tacII promoter. Cells transformed with plasmid pSD12-2 were selected on LB agar plates containing 50 µg/mL of carbenicillin.

Fermentations were done at the 10-liter scale as described in Example 3. When fermentations were done with the cultures that contained the pSD 12-2 plasmid present, 50 mL of a 200 mM solution of isopropyl β-D-thiogalactopyranoside (IPTG) was added to the fermentation culture when the OD550 reached 150-200. Note, however, that IPTG additions can be made at times other than the one described and different amounts of IPTG than described can also be added. Soluble samples were prepared and submitted to the AME5-RP assay as described in Example 3.

As seen in Table 2, the fermentation with the plasmid paTF320 alone resulted in an AME5-RP titer of 650 mg/L. When the cells that were transformed with the plasmid pSD12-2 were grown in a 10 liter fermentation culture, the resulting AME5-RP titer was 1050 mg/L. Coexpressing FkpA with the hinge cysteine mutant of anti-Tissue Factor can also result in significant increases in the fermentation titer.

Example 6

Purification of Full Length Hinge Variant (Cysteine to Serine Mutant) Antibodies Expressed in E. coli (αVegF VNERK Variant and αTF)

Full-length antibodies with variant hinge regions, i.e., containing the hinge cysteine to serine mutations, were purified using conventional chromatography steps, essentially as described in Presta et al., Thromb. Haemost. (2001), 85:379-389. Briefly, fermentation products were purified as follows: bacteria cell paste was diluted 1:5 (w/v) in 20 mM Tris pH 7.5, 5 m M EDTA, then lysed using an M110Y microfluidizer (Microfluidics Corp., Newton, Mass.). Polyethylene imine (BASF Corp., Rensselaer, N.Y.) was added to the supernatant to a final concentration of 0.2%, followed by stirring the mixture at room temperature for 30-90 minutes, then centrifugation (4300×g, 30 min). The supernatant was filtered (0.2 μm) and applied to a Protein A affinity resin, Prosep A (Millipore Corp., Bedford, Mass.). The *E.coli* derived IgG$_1$ was eluted using 0.1 M acetic acid pH 2.9. The αVegF Protein A pool was conditioned by adjusting the pH to 5.5 and diluting with purified water. The αTF Protein A pool was treated similarly, except that the pH was adjusted to 6.5 instead of 5.5, following the addition of urea to give a final concentration of 2M. The conditioned Protein A pool was filtered (0.2 μm) and applied to SP Sepharose FF or SP Sepharose HP (Amersham Pharmacia Biotech, Uppsala, Sweden). The SP Sepharose FF or HP column was washed with 20 mM MES pH 5.5 or 6.5, followed by IgG$_1$ elution using a linear gradient from 0 to 0.25 M NaCl in 20 mM MES pH 5.5 for αVegF or pH 6.5 for αTF. SP Sepharose FF or HP gradient fractions were analyzed by SDS-PAGE and pooled. In some cases, the SP Sepharose FF or HP pool was adjusted to pH 8.0 and diluted with purified water and applied to Q Sepharose FF (Amersham Pharmacia Biotech, Uppsala, Sweden). The αVegF antibody is found in the column flow-through. The αTF antibody is eluted from the Q Sepharose FF using a linear gradient from 50 to 250 mM NaCl in 25 mM Tris pH 8.0. The Q Sepharose FF flow-through pool (αVegF) was formulated by concentration using a 30 kDa regenerated cellulose membrane (Millipore Corp., Bedford, Mass.), followed by dialysis into 10 mM histidine pH 5.5, 0.10 M NaCl. The αTF Q Sepahrose FF pool was formulated by ultrafiltration using a 10 kDa regenerated cellulose membrane (Millipore Corp., Bedford, Mass.), followed by diafiltration into 20 mM sodium acetate pH 5.5, 0.14 M NaCl.

Example 7

Characterization of Full Length Antibodies with Variant Hinge Region (Hinge Cysteine to Serine Mutation) Produced in *E. coli* (αVegF VNERK Variant and αTF Variant)

To further confirm that the antibodies produced in the *E. coli* host cells of the present invention as described above possess desired properties, the anti-VegF and anti-TF antibody products prepared by the procedures of Example 3 (and 6) were further characterized by a series of assays including Mass Spectrometry, Size-Exclusion Chromatography, Amino Acid Analysis, N-terminal Sequencing, and Native Polyacrylamide Gel Electrophoresis (Native PAGE). Results of these analyses are summarized below.

MALDI-TOF-MS Analysis:

MALDI-TOF-MS was performed on a Voyager DE Biospectrometry WorkStation (Perseptive Biosystems, Framingham, Mass.) equipped with delayed extraction. A nitrogen laser was used to irradiate samples with ultraviolet light (337 nm) and an average of 240 scans was taken. The instrument was operated in linear configuration (1.2 m flight path), and an acceleration voltage of 20 kV was used to propel ions down the flight tube after a 60 ns delay. Samples (1.0 ul) were mixed with 1 ul of matrix and 1 ul of this mixture was added to the target and dried under vacuum (50×10-3 Torr). Protein standards were used to achieve a two point external calibration for mass assignment of ions. 4-Hydroxycinnamic acid matrix was used in the analysis of the anti-TF antibodies.

Size Exclusion Chromatography (SEC):

Samples of purified αVegF with the hinge cysteines mutated to serines were ran on a TSK G3000SW-XL column (7.8×300 mM; TosoHaas) on an HP11OO instrument. The column was equilibrated with 100 mM potassium phosphate buffer pH 6.3 containing 250 mM sodium chloride at flow rate of 0.5 ml/min. Samples were diluted to 1 mg/ml with the elution buffer and approximately 100 ug was injected to the column. The run time was 30 min. Samples of gel filtration standards (Bio-Rad) were also injected after five-fold dilutions with the elution buffer.

Samples of purified αTF with the hinge cysteines mutated to serines were run on a Pharmacia Superdex 200 (10×300) mm column on an HP1090 instrument. The column was run at 0.75 ml/min in 20 mM NaPO4, 140 mM NaCl, pH 7.2 and peaks detected at wavelengths 214 and 280 nm. Purified αTF and αVegF were also incubated in 6M urea at 40° C. for 20 minutes prior to injection onto the SEC column. In these cases, the SEC running buffer had 6M urea in addition to the phosphate buffer given above. The flow rate and the column type were as described above.

Amino-Terminal Sequence Analysis:

The sample was exchanged into 0.1% acetic acid by dialysis. An aliquot containing 83 ug was loaded for N-terminal sequence analysis by the Edman degradation method using an Applied Biosystems 477A/120A automated protein sequencer. Peak height comparison to an external standard was used to quantitate PTH-amino acids.

Amino Acid Analysis:

Aliquots containing 15 ug of desalted samples were dried in hydrolysis ampoules by evaporation in a Savant SpeedVac. After addition of 6 N HCl (Pierce), the ampoules were sealed under reduced pressure and incubated for 24 or 72 hours at 110° C. Additional aliquots were subjected to performic acid oxidation by incubation for four hours at 0-5° C. with a solution prepared an hour earlier containing 10% hydrogen peroxide and 90% formic acid. The performic acid was subsequently removed by evaporation in a Savant SpeedVac, after which the samples were subjected to 24-hour hydrolysis in 6 N HCl as described above. For Trp determinations, triplicate aliquots containing 25 ug of each lot were dried in ampoules and incubated at 110° C. for 24 hours under a nitrogen atmosphere in a 7% mercaptoacetic acid (Baker)/ 93% 6 N HCl (Pierce) solution under reduced pressure. After hydrolysis, all samples were dried by evaporation in a Savant SpeedVac.

Hydrolysates were reconstituted in a 0.2 N sodium citrate buffer, pH 2.2 (Beckman) and subjected to amino acid analysis using a Beckman 6300 cation exchange instrument with post-column ninhydrin detection. The signal representing the sum of the absorbance at 440 nm and 570 nm was monitored by a PE Nelson Turbochrom 4 data system. Amino acid quantitation was achieved by peak area or peak height comparisons to external standard mixtures containing 1 or 2 nmol of each component.

Native PAGE Analysis:

Purified antibody samples were diluted with Novex$^R$ Tris-Glycine Native Sample Buffer (Invitrogen, Carlsbad, Calif.) and loaded onto a pre-cast Novex$^R$ 16% Tris glycine gel. The gel was run in Novex$^R$ Tris-Glycine Native Running Buffer at 125 volts for 6-12 hours. The gel was stained with Coomassie Brilliant blue stain and destained per standard protocols.

The results obtained from the various assays described above confirmed that the anti-TF and anti-VegF antibodies produced in *E. coli* using the expression vectors of the present invention where the hinge cysteine residues had been mutated to serine residues share similar structure characteristics to those wild type anti-TF and anti-VegF antibodies containing the hinge cysteine residues produced in *E. coli*. Although the hinge cysteine to serine variant antibodies did not have a covalent link (disulfide linkage) dimerizing the heavy chains, they appeared to have a similar apparent molecular weight under non-denaturing conditions as wild type counterpart antibodies that did contain the hinge cysteines. Incubating the antibodies with the hinge cysteine mutated to serines in 6 M urea at 40° C. prior to SEC in 6 M urea showed that the antibodies ran at the size expected for a wild type antibody (note that despite the presence of a denaturant such as urea, these hinge variant antibodies had apparent molecular weights equivalent to their wild type counterparts, likely due to non-covalent interactions between the hinge variant heavy chains).

Example 8

Functional Analysis of the Variant Antibodies (Hinge Cysteine to Serine Mutants) Produced in E. coli The antibodies produced and purified from E. coli according to the previous Examples were full length and aglycosylated, but missing the covalent disulfide bonds in the hinge region linking the two heavy chains together. The following experiments were performed to illustrate that the antibodies: 1) exhibited tight bivalent antigen binding ability; 2) exhibited strong FcRn binding; and 3) exhibited at least equivalent biological activity compared to their wild type counterparts.

VegF Antigen Binding Affinity

Figure 12:
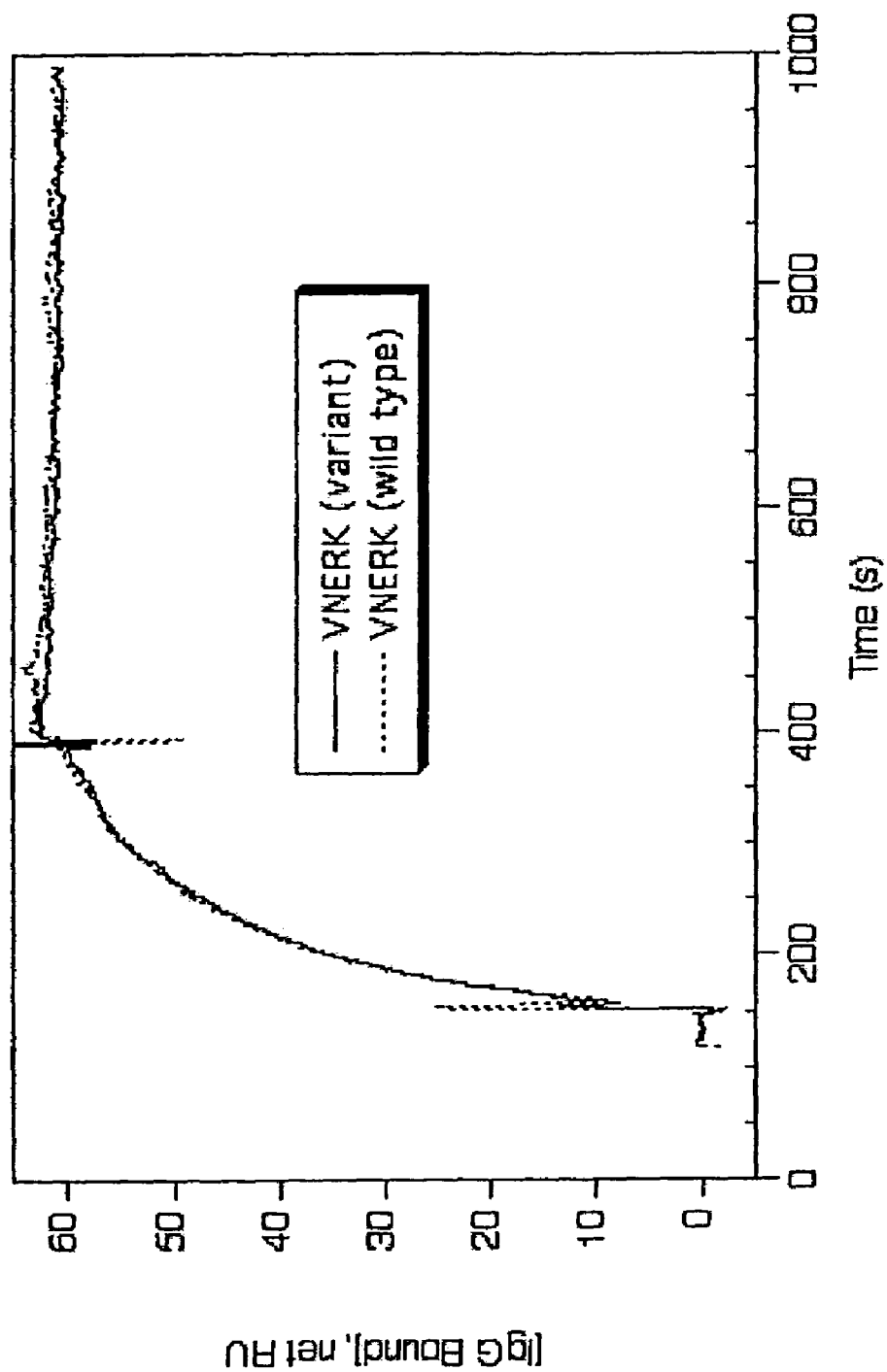
FIG. 12 shows BIAcore sensorgrams of anti-VEGF antibody variants. Shown are response curves at 500 nM VNERK hinge variant produced in E. coli and VNERK hinge wild type produced in E. coli.

A BIAcore-3000 surface plasmon resonance (SPR) system (Biacore Inc., Piscataway, N.J.) was used to determine association ($k_{on}$) and dissociation ($k_{off}$) constants of anti-VEGF variants for binding-to human VEGF essentially as previously described (Chen et al., J. Mol. Biol.(1999), 293, 865-881). A CM-5 biosensor chip (Biacore, Inc.) was activated according to the manufacturer's instructions for amine coupling. Human VEGF 165 was coupled to the chip at a density of 21 response units (RU) in 10 mM sodium acetate buffer, pH 4.8. Unreacted groups were blocked with 1 M ethanolamine. VEGF 165 was made in E. coli as described in Simmons & Yansura, Nat. Biotech. (1996), 14:629-634, followed by refolding. The kinetics of IgG variants binding to immobilized VEGF were measured with 2-fold serial dilutions beginning with 500 nM IgG in running buffer (PBS, 0.05% Tween, 0.01% sodium azide) at a flow rate of 20 µl/min (see FIG. 12). Binding measurements were carried out at 37° C. Regeneration of the chip after each cycle was with 20 mM HCl, followed by washing, an injection of 100 mM Tris pH 8.0, and additional washing.

The kinetic curves were fit to a 1:1 Langmuir binding model using BIAcore evaluation software version 3, which calculated association ($k_{on}$) and dissociation ($k_{off}$) rates. An apparent equilibrium constant, $K_d$, was calculated from $k_{off}/k_{on}$ for each variant (Table 7). The E. coli-derived preparations of VNERK wild type and VNERK variant showed comparable binding affinity, indicating that altering hinge disulfides does not significantly affect antigen binding.

TABLE 7

BIAcore measurements of VEGF binding at 37° C.

| Variant | Hinge region | Source | $k_{on}$ ($10^5$/M/s) | $k_{off}$ ($10^{-6}$/s) | $K_d$, 37° C. (nM) |
|---|---|---|---|---|---|
| VNERK | wild type | E. coli | 0.23 | 5.9 | 0.25 |
| VNERK | variant | E. coli | 0.27 | 6.1 | 0.22 |

As Table 7 shows, wild type and hinge variant VNERK exhibited similar antigen binding affinities.

FcRn Binding Affinity Measurement by ELISA

ELISA plates were coated with 2 µg/ml NeutrAvidin (Pierce, Rockford, Ill.), in 50 mM carbonate buffer, pH 9.6, at 4° C. overnight. Plates were washed with PBS-0.05% polysorbate (wash buffer), pH 7.4, and blocked with PBS-0.5% BSA, pH 7.4 at room temperature for one hour. Human FcRn (Shields, R. L., et. al., J. Biol. Chem. (2001), 276, 6591-6604) was biotinylated using biotin-X-NHS (Research Organics, Cleveland, Ohio) and added to the plates at 2 µg/ml in PBS-0.5% BSA, 0.05% polysorbate 20 (sample buffer), pH 7.4. The plates were incubated for one hour. Eight twofold serial dilutions of either anti-VegF or anti-TF IgG antibodies (1.6-200 ng/ml) in sample buffer, pH 6.0, were added to the plates and the plates were incubated for two hours. Plates were washed with wash buffer, pH 6.0. Bound IgG was detected by adding peroxidase labeled goat F(ab')$_2$ anti-human IgG F(ab')$_2$ (Jackson ImmunoResearch, West Grove, Pa.) in sample buffer, pH 6.0, followed by 3,3',5,5'-tetramethyl benzidine (Kirkegaard & Perry Laboratories) as the substrate. Absorbance was read at 450 nm on a Titertek multiskan (MCC/340) reader (ICN, Costa Mesa, Calif.). Titration curves were fit with a four-parameter nonlinear regression curve-fitting program (KaleidaGraph, Synergy software, Reading, Pa.).

Figure 13:
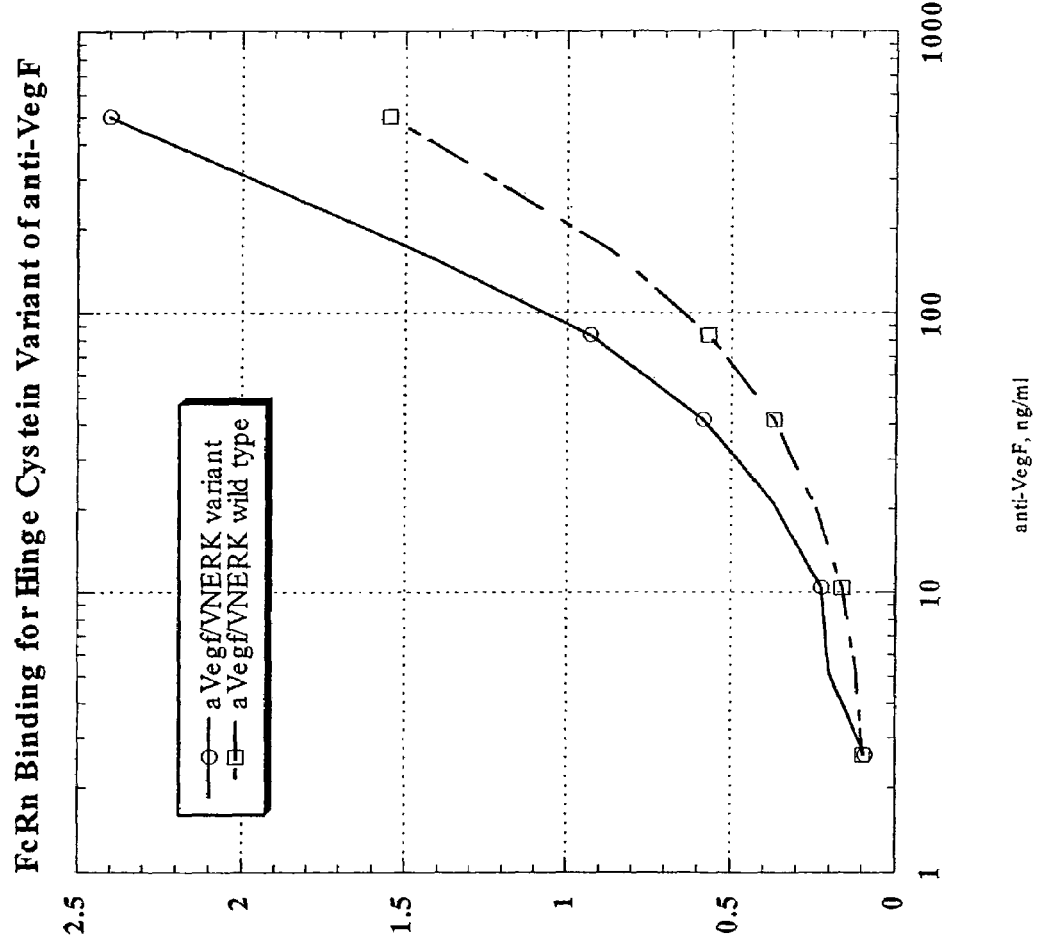
FIG. 13 shows a plot of FcRn binding for an anti-VEGF antibody (VNERK) with a variant hinge region compared to a wild type counterpart.
Figure 14:
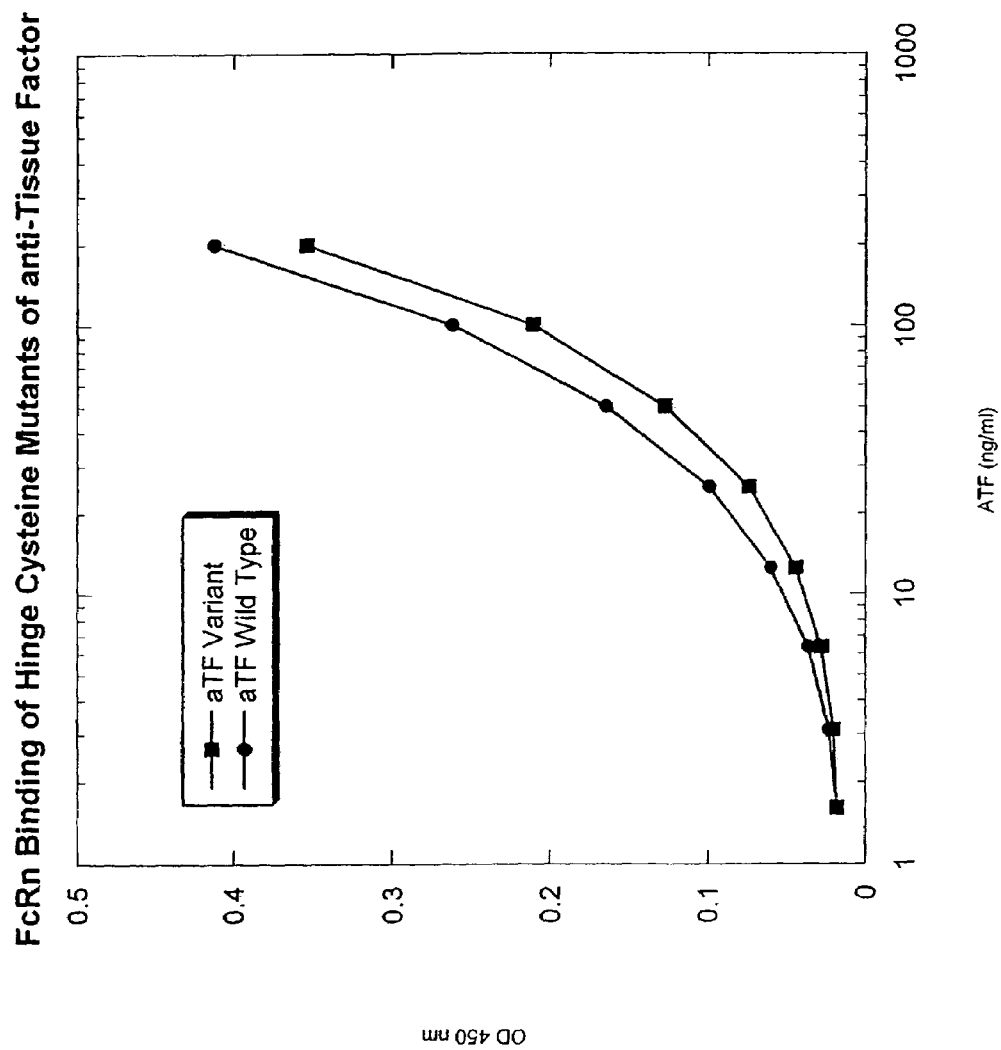
FIG. 14 shows a plot of FcRn binding for an anti-Tissue Factor antibody with a variant hinge region compared to a wild type counterpart.

FIGS. 13 & 14 show that the FcRn binding activity of the E. coli-made anti-VegF and anti-TF antibodies with the variant hinge (cysteines mutated to serines) was comparable to the E. coli-made wild type anti-VegF and anti-TF antibodies (with the hinge cysteines).

Antigen Binding of Antibodies Assessed by ELISA

MaxiSorp 96-well microwell plates (Nunc, Roskilde, Denmark) were coated overnight at 4° C. with 0.5 µg/ml soluble TF comprising residues 1-219 (Kelley, R. F., et. al., Biochem. (1995), 10383-10392) in 50 mM carbonate buffer, pH 9.6. Plates were blocked with 0.5% bovine serum albumin, in phosphate buffered saline (PBS), pH 7.4. Serially diluted antibody standards (0.20-25 ng/ml in 2-fold serial dilution) and samples (minimum dilution 1:10 in 3-fold serial dilution) in PBS containing 0.5% BSA, 0.05% polysorbate 20, 0.35 N NaCl, 5 mM EDTA, 0.25% CHAPS, 0.2% bovine γ-globulins (Sigma, St. Louis, Mo.) were added to the plates. After a 2 h incubation, antibody bound to the plates was detected using anti-human Fc HRP (Jackson ImmunoResearch, West Grove, Pa.) followed by 3,3',5,5'-tetramethyl benzidine (Kirkegaard & Perry Laboratories, Gaithersburg, Md.) as the substrate. Plates were washed between steps and all incubations were performed at room temperature on an orbital shaker. Absorbance was read at 450 nm on a Titerek stacker reader (ICN, Costa Mesa, Calif.). The titration curve was fitted using a four-parameter nonlinear regression curve-fitting program (KaleidaGraph, Synergy software, Reading, Pa.).

Figure 15:
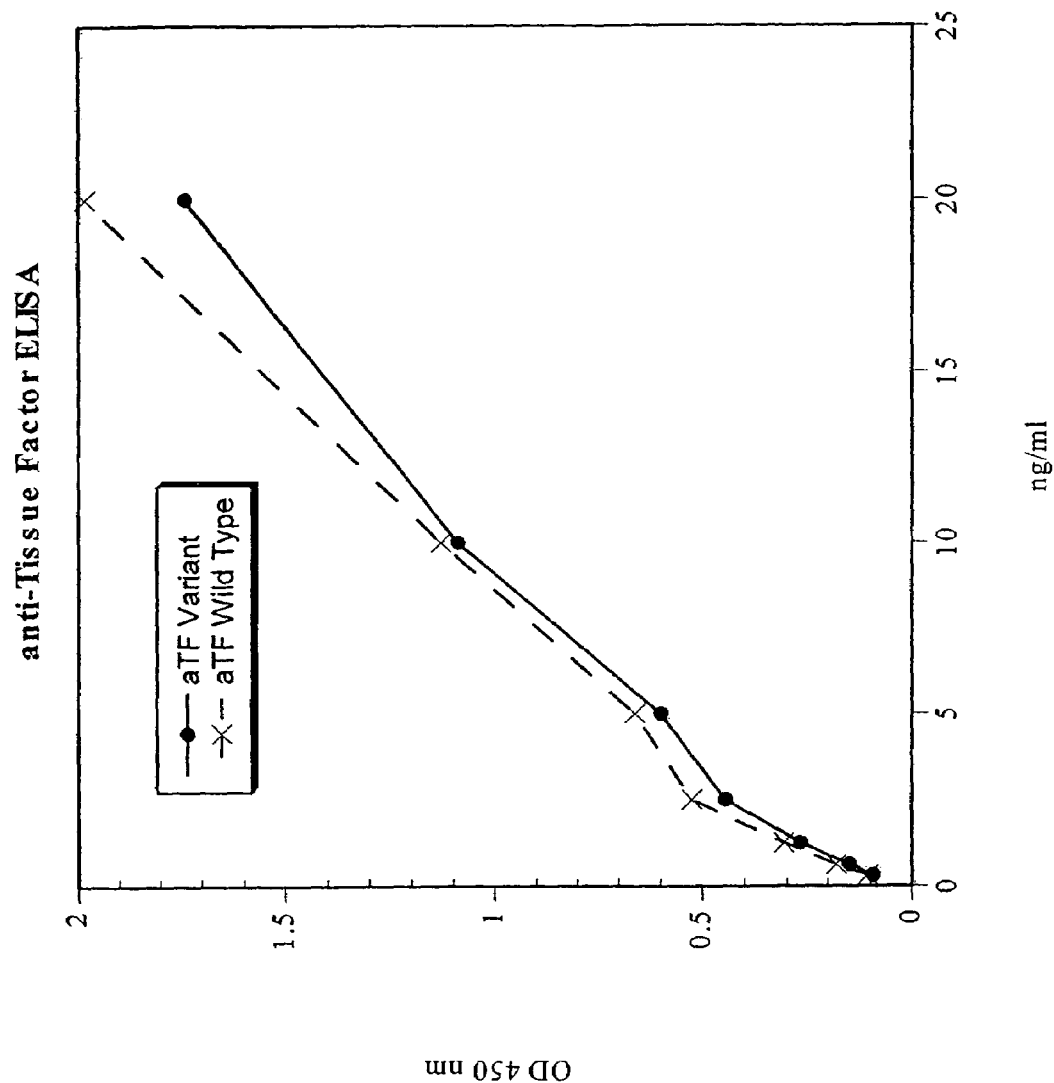
FIG. 15 shows a graph comparing antigen binding capabilities of anti-Tissue Factor antibodies with wild type or variant hinge regions.

Data points which fell in the linear range of the standard curve were used for calculating the anti-TF concentrations in samples. FIG. 15 shows the comparable antigen binding capabilities of anti-TF antibodies with wild type and mutant hinge region.

Protirombin Time Assay

Samples of purified anti-tissue factor containing either the hinge cysteines or the hinge cysteines mutated to serines were tested for biological activity in a prothrombin time assay as described in Presta, et. al., Thromb. Haemost. (2001), 85:379-389. Briefly, samples were tested for activity in a Prothrombin Time (PT) assay. Pooled normal human plasma anticoagulated with sodium citrate (0.38% final) was stored at −70° C. and defrosted in a 37° C. water bath the day of assay. Various concentrations of antibody samples were added to the plasma (dilution made into PBS; 1:10 dilution in plasma) and allowed to incubate at room temperature for 10 minutes. In an IL ACL 6000 coagulometer (Beckman Coulter Inc, Mesa Calif.) 50 ul plasma/antibody sample was mixed with 100 ul Innovin® (Dade Inc, Hialeah Fla.) recombinant human tissue factor/calcium chloride PT reagent. Time to clot formation, as detected optically, was measured. Results were expressed as fold prolongation of PT over mean control sample clotting times (plasma+PBS only). A 4-parameter curve (KaleidaGraph, Synergy Software, Reading Pa.) was fit to the dose-response data by the equation $((m1-m4)/(1+(m0/m3)\wedge m2))+m4$ where $m1$=the maximal clotting time, $m2$=the slope of the curve, $m3$=the inflection point of the curve, and $m4$=the minimal clotting time. The concentration of each sample which prolonged the clotting time two-fold was calculated from this curve by the equation $x=m3(((m1-m4)/(2-m4))-1)\wedge(1/m2)$.

Figure 16:
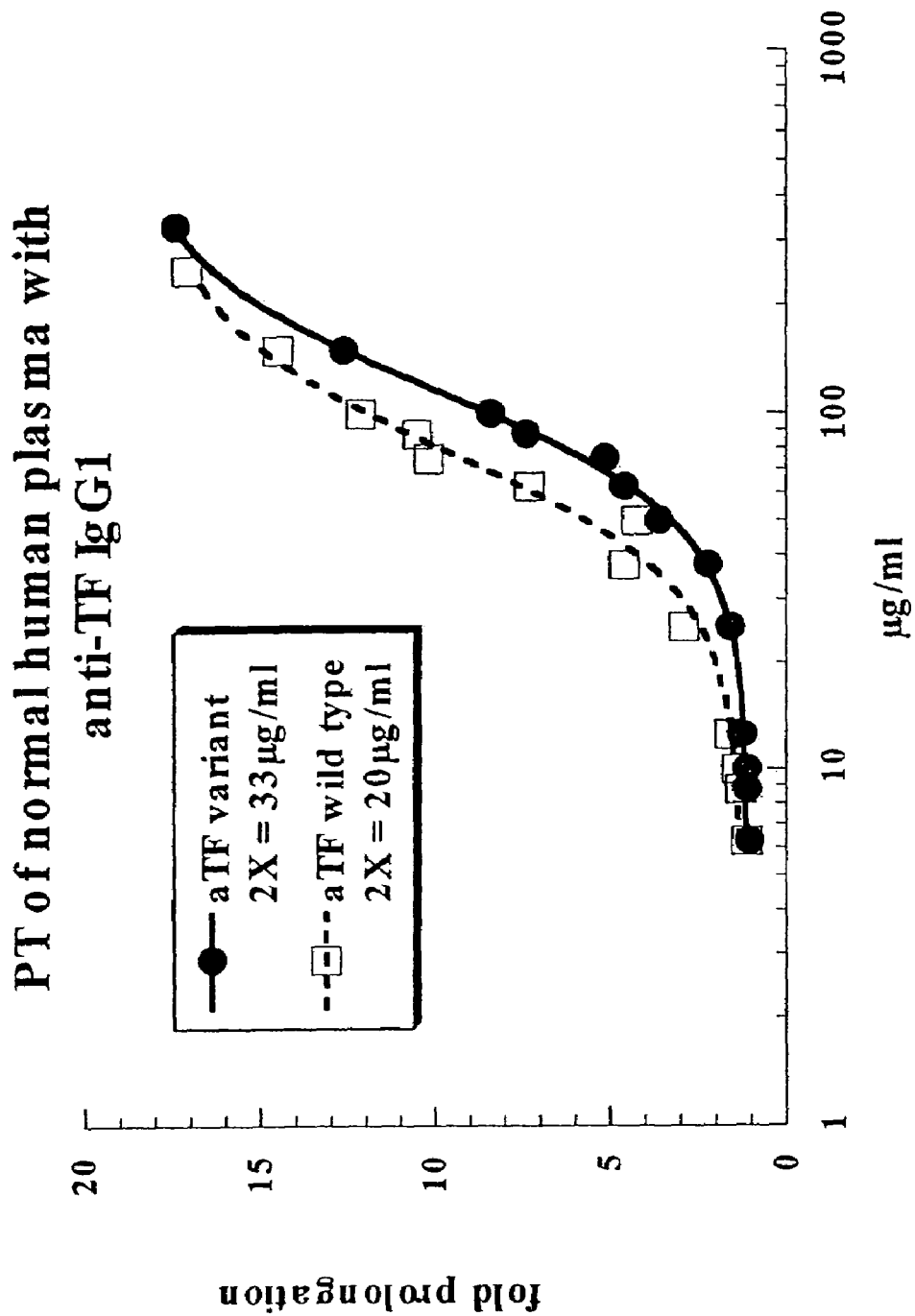
FIG. 16 shows a graph comparing the prothrombin time to clot formation function of anti-Tissue Factor antibodies with wild type or variant hinge regions.

FIG. 16 shows that the antibody containing the hinge cysteines and the antibody containing the hinge cysteines mutated to serines had comparable activities in this assay.

In Vivo Efficacy

Figure 17:
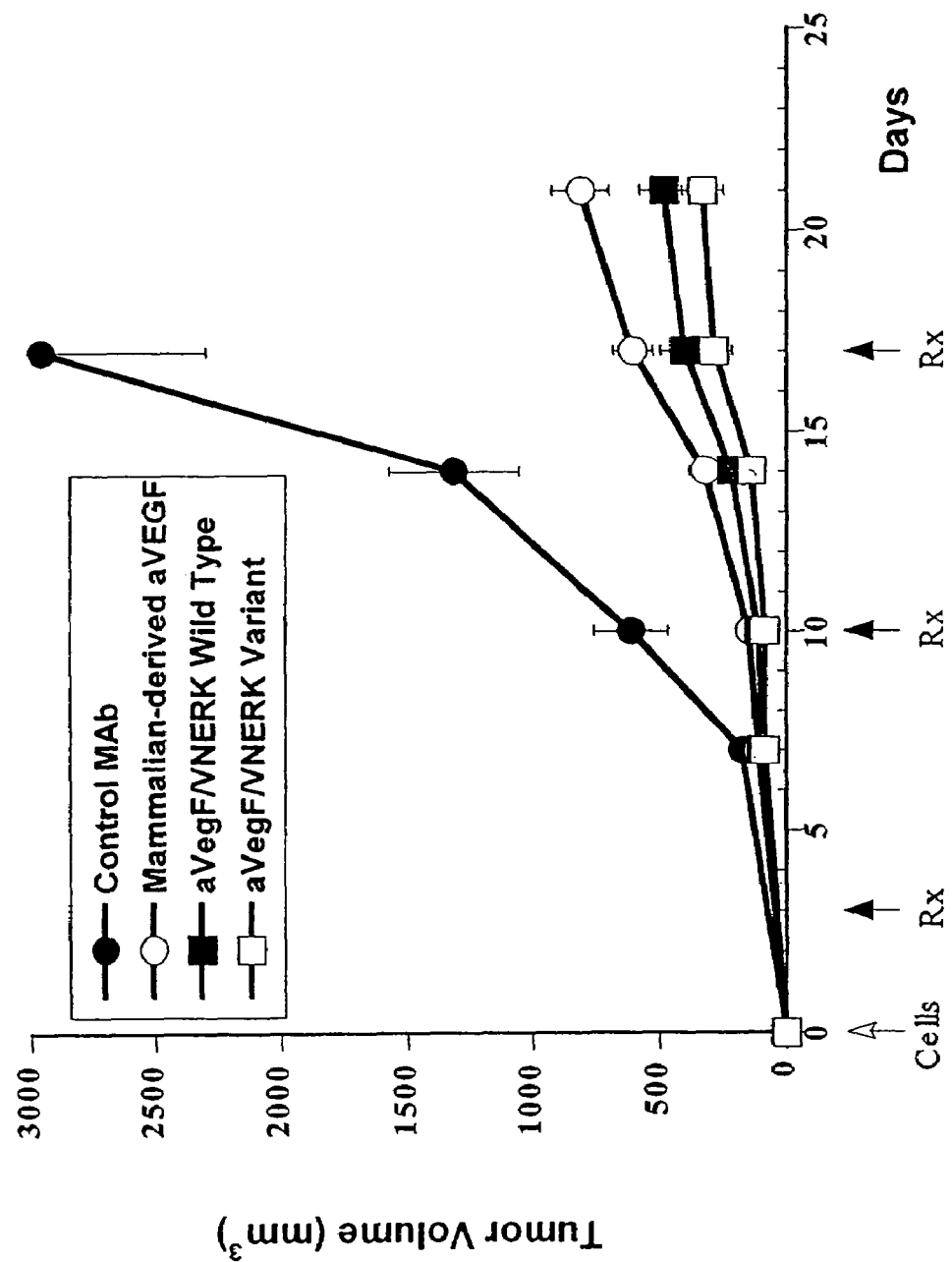
FIGS. 17 & 18 depict comparative results of an in vivo tumor inhibition bioassay of anti-VEGF antibodies with wild type (aVegF/VNERK wild type or aVegF wild type) or variant hinge regions (aVegF/VNERK Variant or aVegF Variant).
Figure 18:
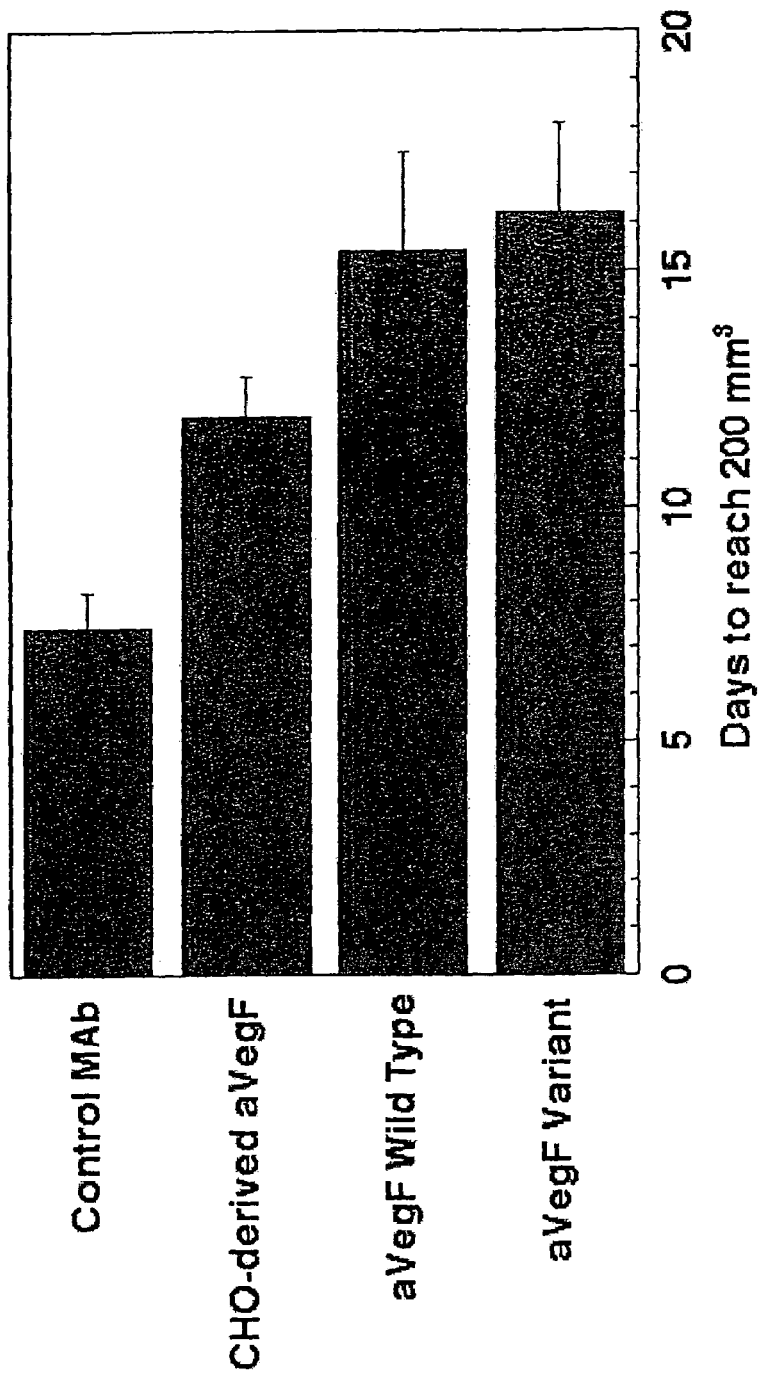

Nude mice were inoculated with 5 million A673 rhabdomyosarcoma cells subcutaneously in the flank. Three days later, mice received an IV injection of an isotype-matched control antibody, humanized and glycosylated anti-VEGF (rhuMAb VEGF), E. coli-produced anti-VEGF VNERK (with wild type hinge) or the hinge cysteine mutant of VNERK (VNERK variant), all at 5 mg/kg. IV dosing was repeated every 7 days. Tumor volume was measured with calipers and plotted as a function of time (FIG. 17). The time for each tumor to grow to 200 $mm^3$ was extrapolated from the growth curves, and the results are shown in FIG. 18. Both FIGS. 17 and 18 show that the antibody made with the hinge cysteines mutated to serines had comparable in vivo anti-tumor activity to the wild type counterpart antibody (that had intact hinge cysteines).

Pharmacokinetics Study of the Variant α-VegF Antibodies

Study Design:

Catheters were surgically implanted into jugular and femoral veins of eighteen male Sprague Dawley rats (body weight 222 to 260 g). After forty eight hours of recovery, rats were divided into four dose groups (n=3/group) and received a single IV bolus of variant (no hinge cysteines) VNERK or wild type VNERK as described in Table 8 below.

TABLE 8

| Group | Dose group | Nominal Dose (mg/kg) | Dose Conc. (mg/mL) | Dose Vol. (mL) |
| --- | --- | --- | --- | --- |
| 1 | Variant VNERK | 1 | 1.0 | 0.25 |
| 2 | Variant VNERK | 10 | 4.4 | 0.57 |
| 3 | Wild type VNERK | 1 | 1.0 | 0.25 |
| 4 | Wild type VNERK | 10 | 10.7 | 0.23 |

Serial blood samples (0.3 mL) were collected just prior to dosing and at 10, 30 min, 1.5, 3, 4, 8 hr and 1, 2, 3, 4, 7, 9, 11, 14, 17, 21, 24, 28 and 35 days after dose administration.

Blood was collected in serum separator tubes, allowed to clot (~30 min) at room temperature, and centrifuged. Serum was harvested and immediately stored at −70° C. until analyzed for drug concentrations by ELISA.

ELISA:

MaxiSorp 96-well microwell plates (Nunc, Roskilde, Denmark) were coated overnight at 4° C. with 0.5 μg/ml VEGF165 in 50 mM carbonate buffer, pH 9.6. Plates were blocked with 0.5% bovine serum albumin, in phosphate buffered saline (PBS), pH 7.4. Serially diluted antibody standards (0.20-25 ng/ml in 2-fold serial dilution) and samples (minimum dilution 1:20 in 3-fold serial dilution) in PBS containing 0.5% BSA, 0.05% polysorbate 20, 0.35 N NaCl, 5 mM EDTA, 0.25% CHAPS, 0.2% bovine γ-globulins (Sigma, St. Louis, Mo.) were added to the plates. After a 2 h incubation, antibody bound to the plates was detected by adding goat anti-human IgG F(ab')2 HRP (Jackson ImmunoResearch, West Grove, Pa.) followed by 3,3',5,5'-tetramethyl benzidine (Kirkegaard & Perry Laboratories, Gaithersburg, Md.) as the substrate. Plates were washed between steps and all incubations were performed at room temperature on an orbital shaker. Absorbance was read at 450 nm on a Titerek stacker reader (ICN, Costa Mesa, Calif.). The titration curve was fitted using a four-parameter nonlinear regression curve-fitting program (KaleidaGraph, Synergy software, Reading, Pa.).

Data points that fell in the linear range of the standard curve were used for calculating the anti-VEGF antibody concentrations in samples.

Data Analysis:

Graphs of concentration versus time profiles were made using KaleidaGraph (KaleidaGraph V. 3.09, Synergy Software. Reading, Pa.). Values reported as less than reportable (LTR) were not included in the PK analysis and are not represented graphically. Pharmacokinetic parameters were determined by compartmental analysis using WinNonlin software (WinNonlin Pro V. 3.1, Pharsight Corporation. Mountain View, Calif.). Pharmacokinetic parameters were computed as described elsewhere (Ritschel W A and Kearns G L, Handbook of basic pharmacokinetics including clinical applications ($5^{th}$ edition; American Pharmaceutical Assoc., Washington, DC.).

Figure 19:
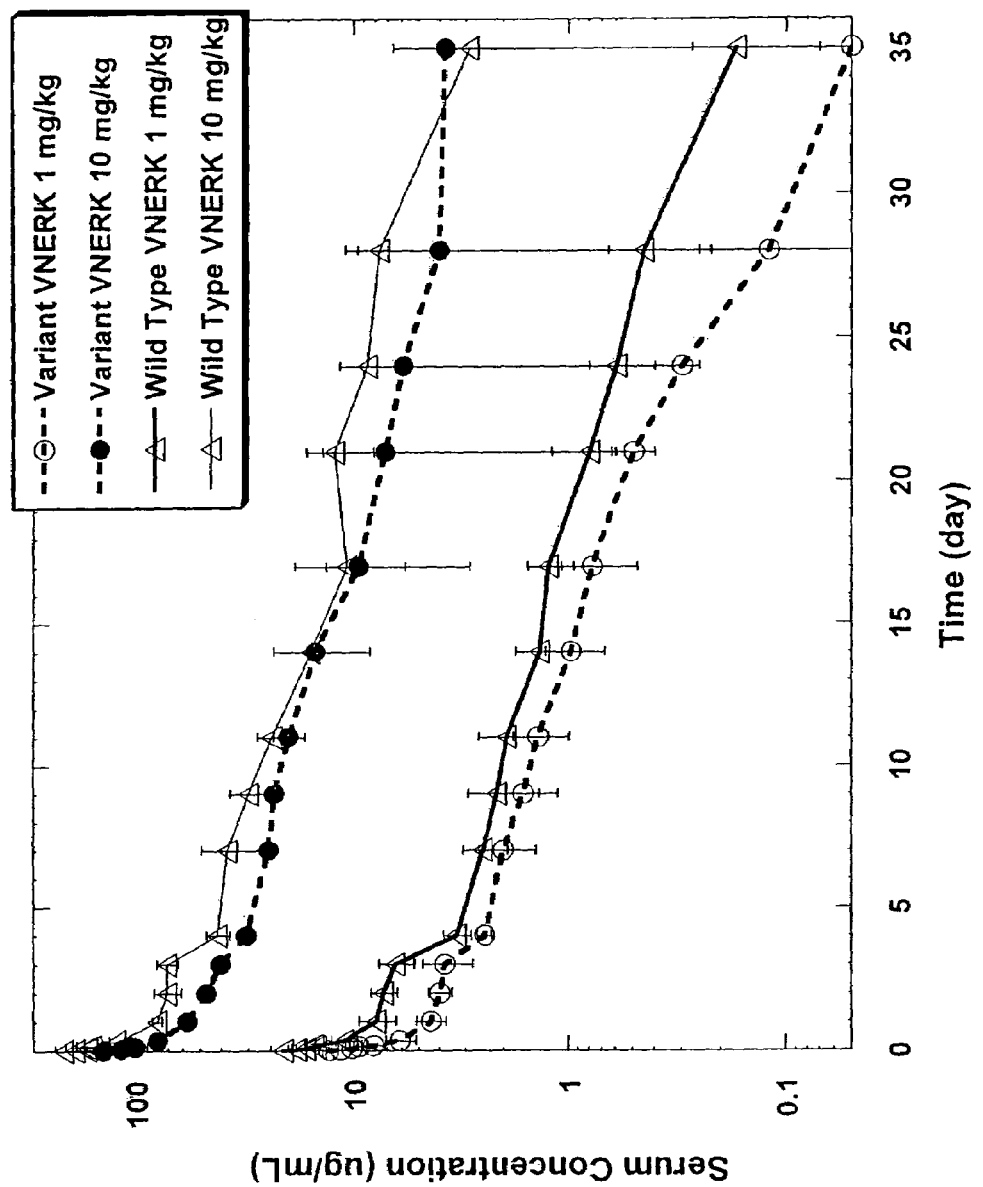
FIG. 19 shows a graph depicting serum concentration of anti-VEGF antibodies with wild type or variant hinge regions over time.

Results:

Group average serum concentration vs. time data (±SD) are presented in FIG. 19.

A two-compartment model with bolus input and first-order output (WinNonlin model #7) was used to fit observed serum concentration vs. time data. Calculated pharmacokinetic parameters (based on actual doses) are presented in Table 9 below.

Estimates of drug exposure (AUC) and maximal serum concentrations (Cmax) of variant and wild type VNERK at high dose (10 mg/kg) was approximately 10 to 15 fold higher than low dose (1 mg/kg) suggesting the drug exposure is proportional to dose. Both wild type and variant VNERK were cleared slightly faster at the 1 mg/kg dose level compared to the high dose.

When comparing wild type and variant VNERK, drug clearance was similar across the dose range studied. Other pharmacokinetic parameters, including distribution (alpha) half-lives, beta half-lives and distribution volumes (V1), were similar between these two antibody versions.

In summary, the pharmacokinetics of E. coli wild type and variant VNERK in rats were similar over the studied dose range.

TABLE 9

Pharmacokinetic Parameter Summary

| Parameter | Varient VNERK 1 mg/kg | Varient VNERK 10 mg/kg | Wild type VNERK 1 mg/kg | Wild type VNERK 10 mg/kg |
|---|---|---|---|---|
| AUC (h*μg/mL) | 4.25 ± 10 | 586 ± 80 | 62.1 ± 13 | 807 ± 180 |
| Cmax (μg/mL) | 12.8 ± 0.80 | 145 ± 13 | 20.2 ± 2.4 | 210 ± 23 |
| CL (mL/day/kg) | 17.2 ± 2.9 | 14.5 ± 1.8 | 15.4 ± 3.4 | 13.2 ± 2.5 |
| K10 half-life (day) | 2.29 ± 0.40 | 2.80 ± 0.24 | 2.18 ± 0.65 | 2.66 ± 0.44 |
| alpha half-life (day) | 0.138 ± 0.019 | 0.173 ± 0.062 | 0.153 ± 0.029 | 0.199 ± 0.062 |
| beta half-life (day) | 5.71 ± 0.92 | 6.99 ± 1.0 | 4.58 ± 1.7 | 6.20 ± 1.89 |
| $V_1$ (mL/kg) | 55.6 ± 0.83 | 58.4 ± 6.3 | 46.3 ± 5.9 | 49.4 ± 3.7 |
| Vss (mL/kg) | 134 ± 17 | 140 ± 15 | 93.0 ± 19 | 108 ± 9.1 |

Pharmacokinetics Study of the Variant α-TF Antibodies

Study Design:

Catheters were surgically implanted into jugular and femoral veins of eight male Sprague Dawley rats. After three days of recovery, rats were divided into two dose groups (n=4/group) and received a single IV bolus of variant (no hinge cysteines) or wild type (hinge cysteines) αTF.

Each form of αTF was diluted in placebo to 1.6 mg/mL. All rats were dosed via the femoral cannula at 3 mg/kg IV bolus. Rat weights on day 0 ranged from 0.272-0.304 kg. Dosing volumes ranged from 0.52-0.58 ml. Blood samples (~300 μl) were collected via the jugular cannula at 0 (pre-dose), 5, 30, 60 minutes, 2, 4, 8 hours, 1, 2, 3, 4, 7, 10, 14, 21, 28, and 42 days post administration. In the event of non-patent cannulae, blood was collected via the tail vein. Blood was collected into tubes containing 3.8% sodium citrate and centrifuiged. Upon centrifugation, plasma was collected and stored at −70° C. until assayed using an anti-Tissue Factor ELISA.

Data Analysis

Plasma drug concentration versus time profiles were plotted on a semilog plot using Microsoft Excel. Pharmacokinetic parameters were determined using WinNonLin Software (Version 3.0). The PK model used (Model #7) was an IV Bolus, 2 compartmental PK model assuming a first order elimination rate. Statistical analysis using ANOVA and t-test were done to determine differences in PK parameters among groups.

ELISA:

MaxiSorp 96-well microwell plates (Nunc, Roskilde, Denmark) were coated overnight at 4° C. with 0.5 μg/ml of soluble TF comprising residues 1-219 (as above) in 50 mM carbonate buffer, pH 9.6. Plates were blocked with 0.5% bovine serum albumin, in phosphate buffered saline (PBS), pH 7.4. Serially diluted antibody standards (0.20-25 ng/ml in 2-fold serial dilution) and samples (minimum dilution 1:10 in 3-fold serial dilution) in PBS containing 0.5% BSA, 0.05% polysorbate 20, 0.35 N NaCl, 5 MM EDTA, 0.25% CHAPS, 0.2% bovine γ-globulins (Sigma, St. Louis, Mo.) were added to the plates. After a 2-h incubation, antibody bound to the plates was detected using anti-human Fc HRP (Jackson ImmunoResearch), followed by 3,3',5,5'-tetramethyl benzidine (Kirkegaard & Perry Laboratories, Gaithersburg, Md.) as the substrate. Plates were washed between steps and all incubations were performed at room temperature on an orbital shaker. Absorbance was read at 450 nm on a Titerek stacker reader (ICN, Costa Mesa, Calif.). The titration curve was fitted using a four-parameter nonlinear regression curve-fitting program (KaleidaGraph, Synergy software, Reading, Pa.). Data points that fell in the linear range of the standard curve were used for calculating the anti-TF antibody concentrations in samples. Results are depicted in Table 10.

TABLE 10

Anti-TF Pharmacokinetic Parameter Summary

| Parameter | Varient anti-TF 3 mg/kg | Wild type anti-TF 3 mg/kg |
|---|---|---|
| AUC (Day*μg/mL) | 271.54 ± 68.42 | 278.54 ± 15.81 |
| CL (mL/day/kg) | 12.53 ± 3.05 | 13.57 ± 0.70 |
| alpha half-life (day) | 0.31 ± 0.16 | 0.35 ± 0.12 |
| beta half-life (day) | 8.86 ± 2.60 | 8.31 ± 0.41 |
| $V_1$ (mL/kg) | 62.59 ± 3.19 | 55.29 ± 4.33 |
| $V_2$ (mL/kg) | 81.45 ± 15.03 | 93.83 ± 11.10 |
| Vss (mL/kg) | 144.05 ± 14.10 | 149.12 ± 9.24 |

Similar to the results obtained with wild type and variant VNERK, wild type and variant anti-TF drug clearances were similar at the dose range studied. Other pharmacokinetic parameters, including distribution (alpha) half-lives, beta half-lives and distribution volumes (V1), were similar between these two antibody versions.

In summary, the pharmacokinetics of *E. coli*-derived wild type and variant anti-TF in rats were similar at the studied dose range.

Example 9

Determination of Assembly Efficiencies

To assess the assembly efficiencies of the light chain and heavy chain produced in the fermentations, a reversed-phase HPLC assay was used to quantitate light and heavy chains. Whole broth samples from small scale fermentations were used for this assay. The frozen whole broth samples were thawed at room temperature. An aliquot of whole broth was diluted in 6M Guanidine-HCl, 50 mM TRIS, pH 8.0 (typically 50 μL of sample was diluted with 900 μl of the guanidine solution). 50 μL of 2M dithiothreitol (freshly thawed) was then added. The samples were incubated at room temperature for 30-60 minutes prior to centrifuging at 13,000 rpm and 4-8° C. for 15-30 minutes. The supernatant was removed for further assay.

For the reversed-phase methodology, a Hewlett-Packard™ 1100 HPLC was used with a Perseptive Poros™ R-1 reversed phase column. Analyses were run with the column heated to 60-80° C. and UV absorbance at 278 nm was monitored. The column was equilibrated in a 30% acetonitrile solution in water with 0.1% trifluoroacetic acid. 25 µl of sample was next loaded on the column, and elution was performed using a linear gradient from 30% to 36% acetonitrile over 20 minutes followed by a 17 minute period of regeneration at 95% acetonitrile and re-equilibration at 30% acetonitrile. Peaks for light chain and heavy chain-related species were identified by comparison with standards. Fermentation samples from a blank run in which no recombinant protein was made were similarly prepared and analyzed to determine the appropriate baselines for the analyses. Integration of the peak areas was performed using the Hewlett-Packard™ 1100 software and standards were spiked into blank run samples to generate a calibration curve in order to quantify the relative quantity of the various species in the samples.

Whole broth samples from anti-Tissue Factor fermentations with the cultures 61D6/pxTF2AP22 and 61D6/paTF320 were analyzed to determine what percentage of the light chain and heavy chain produced during these fermentations was assembled into full-length antibody, as detected by the AME5-RP assay. The results of these calculations are shown in Table 11. These data show that when the hinge cysteines were mutated to serines, the amount of assembled antibody increased due to an increased efficiency of light chain and heavy chain assembly.

TABLE 11

| Plasmid | TIR (LC, HC) | Hinge Cysteines | AME5-RP, mg/L | % LC | % HC |
|---------|--------------|-----------------|---------------|------|------|
| pxTF2AP22 | 2, 2 | yes | 110 | 10 | 5 |
| pxTF2AP22 | 2, 2 | yes | 110 | 8 | 4 |
| paTF320 | 2, 2 | no | 605 | 34 | 22 |
| paTF320 | 2, 2 | no | 720 | 47 | 30 |

The invention claimed is:

1. An isolated, recombinant or synthetic polynucleotide encoding a variant antibody heavy chain lacking at least one amino acid in an antibody hinge region capable of forming a disulfide linkage, made by a method comprising:
   (a) providing a nucleic acid encoding an antibody heavy chain comprising an amino acid residue in an antibody hinge region capable of forming at least one disulfide linkage;
   (b) modifying the nucleic acid to encode a variant of the antibody lacking at least one amino acid residue in the antibody hinge region capable of forming at least one disulfide linkage; and
   (c) adding to the modified nucleic acid of (b), a nucleic acid encoding a prokaryotic secretion signal sequence or a periplasmic secretion sequence.

2. A prokaryotic host cell comprising
   (i) a nucleic acid comprising the polynucleotide of claim 1;
   (ii) a vector comprising the polynucleotide of claim 1;
   (iii) an expression vector comprising the polynucleotide of claim 1;
   (iv) the nucleic acid of (i), the vector of (ii) or the expression vector of (iii), wherein the prokaryotic host cell is a gram-negative cell or a gram-positive cell; or
   (v) the host cell of (iv), wherein the prokaryotic host cell is an *Escherichia* cell, an *E. coli* cell, a *Bacilli* cell, a *B. subtilis* cell, an *Enterobacteria* cell, a *Pseudomonas* species cell, a *P. aeruginosa* cell, a *Salmonella* sp. cell or an *S. typhimurium* cell, a *Serratia marcescans* cell, a *Klebsiella* sp. cell, a *Proteus* sp. cell, a *Shigella* sp. cell, a *Rhizobia* sp. cell, *Vitreoscilla* sp. cell, or a *Paracoccus* sp. cell; or
   (vi) the nucleic acid of (i), the vector of (ii) or the expression vector of (iii), wherein the prokaryotic host cell is a bacterial, an *Archaebacterial* or a *Eubacterial* cell.

3. A method for producing a prokaryotic cell extract comprising expressing in a prokaryotic host cell a polynucleotide encoding an antibody comprising a variant heavy chain hinge region lacking at least one amino acid capable of forming a disulfide linkage, wherein the polynucleotide comprises the polynucleotide of claim 1 and recovering a prokaryotic cell extract.

4. The polynucleotide of claim 1, wherein the nucleic acid is modified to encode a variant of the antibody lacking at least two amino acid residues in the antibody hinge region capable of forming a disulfide linkage.

5. The polynucleotide of claim 4, wherein the nucleic acid is modified to encode a variant of the antibody lacking all amino acid residues in the antibody hinge region capable of forming a disulfide linkage.

6. The polynucleotide of claim 1, wherein the modification comprises changing the amino acid residue capable of forming a disulfide linkage in the antibody hinge region to a serine residue.

7. The polynucleotide of claim 6, wherein the modification comprises changing all heavy chain hinge region cysteine amino acid residues in the antibody hinge region to a serine residue.

8. A method for producing a prokaryotic cell extract comprising a recombinant heavy chain-light chain dimer antibodies comprising:
   (I)(A) providing a nucleic acid encoding a variant antibody heavy chain lacking at least one amino acid residue in the antibody hinge region capable of forming an inter-chain disulfide linkage,
   wherein the nucleic acid encoding the variant antibody heavy chain is made by a method comprising:
      (i)(a) providing a nucleic acid encoding an antibody heavy chain comprising at least one amino acid residue in the antibody hinge region capable of forming at least one inter-heavy chain disulfide linkage, and
      (b) modifying the nucleic acid to encode a variant of the antibody lacking at least one of the amino acid residues in the antibody hinge region capable of forming at least one inter-heavy chain disulfide linkage;
      (ii) the method of (i), wherein the nucleic acid is modified to encode a variant of the antibody lacking at least two amino acid residues capable of forming a disulfide linkage, or an inter-heavy chain disulfide linkage;
      (iii) the method of (ii), wherein the nucleic acid is modified to encode a variant of the antibody lacking all amino acid residues capable of forming a disulfide linkage, or an inter-heavy chain disulfide linkage;
      (iv) the method of any of (i) to (iii), wherein the modification comprises changing the amino acid residue capable of forming a disulfide linkage, or an inter-heavy chain disulfide linkage, to a serine residue;
      (v) the method of any of (i) to (iv), wherein the modification comprises changing a heavy chain hinge region cysteine amino acid residue to an amino acid residues incapable of forming an inter-heavy chain disulfide linkage;
      (vi) the method of (v), wherein the modification comprises changing a heavy chain hinge region cysteine amino acid residue to a serine amino acid residue;

(vii) the method of any of (i) to (vi), wherein the modified nucleic acid further comprises nucleic acid encoding a secretion signal sequence, or a prokaryotic secretion signal sequence, or a periplasmic secretion sequence;

(viii) the method of any of (i) to (vii), wherein the modified nucleic acid further comprises a transcriptional regulatory sequence and a translation initiation region;

(ix) the method of any of (i) to (viii), wherein the heavy chain is an IgG, an IgA, an IgE, an IgM or an IgD heavy chain;

(x) the method of (viii), wherein the translation initiation region is a Shine-Dalgarno sequence;

(xi) the method of (viii), wherein the transcriptional regulatory sequence for the heavy chain-encoding has the same transcriptional regulatory strength as the transcriptional regulatory sequence for the light chain-encoding nucleic acid;

(xii) the method of (viii), wherein the transcriptional regulatory sequence comprises a prokaryotic promoter, an inducible promoter, a constitutive promoter, a phoA promoter, a tac promoter, a promoter responsive to a culture condition, a promoter responsive to the presence or absence of a nutrient in a culture or a change in temperature in a culture, a beta-galactamase promoter, a lactose promoter, a tryptophan (trp) promoter or a trc promoter; or (xiii) the method of any of (i) to (xii), wherein the heavy chain-encoding nucleic acid comprises a human antibody heavy chain-encoding sequence;

(B) providing a nucleic acid encoding an antibody light chain capable of forming an antibody dimer with the heavy chain of (A); and (C)(i) expressing the nucleic acids of (A) and (B) in a prokaryotic cell extract under conditions wherein the heavy and light chain polypeptides are expressed and form an antibody dimer, or, (ii) expressing the nucleic acids of (A) and (B) in a prokaryotic cell under conditions wherein the heavy and light chain polypeptides are expressed and form an antibody dimer, and then making a prokaryotic cell extract comprising antibody dimers; or (II) the method of (I), wherein the prokaryotic cell or cell extract is a bacterial, an *Archaebacterial* or a *Eubacterial* cell or cell extract.

9. The method of claim 8, wherein the modified nucleic acid encoding the variant heavy chain further comprises a nucleic acid encoding an antibody light chain capable of forming a functional antibody dimer with the heavy chain, and the heavy chain-encoding and light chain-encoding nucleic acids are operatively joined to form a cistron comprising a separate transcriptional regulatory sequence and a separate translation initiation region for each of the heavy chain-encoding and light chain-encoding nucleic acids, and the translation initiation region for the heavy chain-encoding is of similar strength to the translation initiation region for the light chain-encoding nucleic acid.

10. The method of claim 8, wherein
(a) the prokaryotic cell is a gram-negative cell or a gram-positive cell;
(b) the method of (a), wherein the prokaryotic cell is an *Escherichia* cell, an *E. coli* cell, a *Bacilli* cell, a *B. subtilis* cell, an *Enterobacteria* cell, a *Pseudomonas* species cell, a *P. aeruginosa* cell, a *Salmonella* sp. cell or an *S. typhimurium* cell, a *Serratia marcescans* cell, a *Kiebsiella* sp. cell, a *Proteus* sp. cell, a *Shigella* sp. cell, a *Rhizobia* sp. cell, *Vitreoscilla* sp. cell, or a *Paracoccus* sp. cell; or
(c) the method of any of (a) to (b), wherein a prokaryotic cell extract comprising the functional antibody dimers is produced from the prokaryotic cells.

11. The method of claim 8, wherein the nucleic acids of (A) and (B) are cloned into an expression vector.

12. The method of claim 8, wherein
(a) a decreased amount of inter-heavy chain disulfide bonds between the antibody hinge region of the variant heavy chain and another polypeptide are formed, thereby allowing a higher amount of functional antibody dimer to be formed, as compared to the amount of a non-modified antibody heavy chain expressed under similar conditions;
(b) the method of (a), wherein a decreased amount of inter-heavy chain aggregates are formed;
(c) the method of (a) or (b), wherein a decreased amount of inter-heavy chain aggregate is about 5% to 90% less than the amount of non-modified antibody heavy chain expressed under similar conditions; or
(d) the method of (c), wherein the decreased amount of inter-heavy chain aggregates is about 25% less than the amount of non-modified antibody heavy chain expressed under similar conditions.

13. A method for producing recombinant heavy chain-light chain dimer antibodies in a prokaryotic cell, comprising:
(I)(A) providing a nucleic acid encoding a variant antibody heavy chain lacking at least one amino acid residue in the antibody hinge region capable of forming an inter-chain disulfide linkage,
wherein the nucleic acid encoding the variant antibody heavy chain is made by a method comprising:
(i)(a) providing a nucleic acid encoding an antibody heavy chain comprising at least one amino acid residue in the antibody hinge region capable of forming at least one inter-chain disulfide linkage, and
(b) modifying the nucleic acid to encode a variant of the antibody lacking at least one of the amino acid residues in an antibody hinge region capable of forming at least one inter-chain disulfide linkage, and to encode a secretion signal sequence or a periplasmic secretion sequence;
(ii) the method of (i), wherein the nucleic acid is modified to encode a variant of the antibody lacking at least two amino acid residues capable of forming a disulfide linkage, or an inter-heavy chain disulfide linkage;
(iii) the method of (ii), wherein the nucleic acid is modified to encode a variant of the antibody lacking all amino acid residues capable of forming a disulfide linkage, or an inter-heavy chain disulfide linkage;
(iv) the method of any of (i) to (iii), wherein the modification comprises changing the amino acid residue capable of forming a disulfide linkage, or an inter-heavy chain disulfide linkage, to a serine residue;
(v) the method of any of (i) to (iv), wherein the modification comprises changing a heavy chain hinge region cysteine amino acid residue to an amino acid residues incapable of forming an inter-chain disulfide linkage;
(vi) the method of (v), wherein the modification comprises changing a heavy chain hinge region cysteine amino acid residue to a serine amino acid residue;
(vii) the method of any of (i) to (vi), wherein the modified nucleic acid further comprises nucleic acid encoding a prokaryotic secretion signal sequence, or a prokaryotic secretion signal sequence, or a prokaryotic periplasmic secretion sequence;

(viii) the method of any of (i) to (vii), wherein the modified nucleic acid further comprises a transcriptional regulatory sequence and a translation initiation region;

(ix) the method of any of (i) to (viii), wherein the heavy chain is an IgG, an IgA, an IgE, an IgM or an IgD heavy chain;

(x) the method of (viii), wherein the translation initiation region is a Shine-Dalgarno sequence;

(xi) the method of (viii), wherein the transcriptional regulatory sequence for the heavy chain-encoding has the same transcriptional regulatory strength as the transcriptional regulatory sequence for the light chain-encoding nucleic acid;

(xii) the method of (viii), wherein the transcriptional regulatory sequence comprises a prokaryotic promoter, an inducible promoter, a constitutive promoter, a phoA promoter, a tac promoter, a promoter responsive to a culture condition, a promoter responsive to the presence or absence of a nutrient in a culture or a change in temperature in a culture, a beta-galactamase promoter, a lactose promoter, a tryptophan (trp) promoter or a trc promoter; or (xiii) the method of any of (i) to (xii), wherein the heavy chain-encoding nucleic acid comprises a human antibody heavy chain-encoding sequence;

(B) providing a nucleic acid encoding an antibody light chain capable of forming a functional antibody dimer with the heavy chain of (A); and (C) expressing the nucleic acids of (A) and (B) in the prokaryotic cell under conditions wherein the heavy and light chain polypeptides are expressed and form a functional antibody dimer;

wherein the amount of an antibody produced in the prokaryotic cell is at least about 10% greater than the amount of the unmodified antibody heavy chain of (A)(i)(a) expressed under similar conditions, wherein the antibody heavy chain of (A)(i)(a) has a wild type ability to form disulfide linkages; or (II) the method of (I), wherein the prokaryotic cell is a bacterial, an *Archaebacterial* or a *Eubacterial* cell or cell extract.

14. A method for producing a prokaryotic cell extract comprising
    (a) expressing in a prokaryotic host cell a polynucleotide encoding an antibody comprising a variant heavy chain hinge region lacking at least one amino acid capable of forming a disulfide linkage, wherein the polynucleotide comprises the prokaryotic cell of claim 2; and
    (b) recovering a prokaryotic cell extract.

15. The polynucleotide of claim 1, further comprising:
    (a) a transcriptional regulatory sequence and a translation initiation region;
    (b) a nucleic acid encoding an antibody light chain capable of forming an antibody dimer with the heavy chain, wherein the heavy chain-encoding and light chain-encoding nucleic acids are operatively joined to form a cistron comprising a separate transcriptional regulatory sequence and a separate translation initiation region for each of the heavy chain-encoding and light chain-encoding nucleic acids, and the translation initiation region for the heavy chain-encoding is of similar strength to the translation initiation region for the light chain-encoding nucleic acid;
    (c) a translation initiation region comprising a Shine-Dalgarno sequence; or
    (d) a nucleic acid encoding a secretion sequence, or a prokaryotic periplasmic secretion sequence, operatively linked to the heavy chain-encoding and light chain-encoding nucleic acids.

16. The polynucleotide of claim 1, wherein the transcriptional regulatory sequence for the heavy chain-encoding has the same transcriptional regulatory strength as the transcriptional regulatory sequence for the light chain-encoding nucleic acid.

17. The polynucleotide of claim 1, wherein the transcriptional regulatory sequence comprises a prokaryotic promoter, an inducible promoter, a constitutive promoter, a phoA promoter, a tac promoter, a promoter responsive to a culture condition, a promoter responsive to the presence or absence of a nutrient in a culture or a change in temperature in a culture, a beta-galactamase promoter, a lactose promoter, a tryptophan (trp) promoter or a trc promoter.

18. The polynucleotide of claim 1, wherein the heavy chain-encoding or the light chain-encoding nucleic acid comprises a human antibody-encoding sequence.

19. The polynucleotide of claim 1, wherein the heavy chain is an IgG, an IgA, an IgE, an IgM or an IgD heavy chain.

20. The polynucleotide of claim 1, wherein the nucleic acid is modified to encode a variant of the antibody lacking at least one antibody hinge region amino acid residue capable of forming at least one inter-heavy disulfide linkage.

21. The polynucleotide of claim 1, wherein the polynucleotide of any of (i) to (x), wherein at least one antibody cysteine amino acid residue is modified to a different amino acid residue not capable of forming an inter-heavy chain disulfide linkage.

22. The method of claim 13, wherein the amount of an antibody produced in the prokaryotic cell is at least 25% greater than the amount of the unmodified antibody heavy chain of (A)(i)(a) expressed under similar conditions.

23. The method of claim 22, wherein the amount of an antibody produced in the prokaryotic cell is at least 50% greater than the amount of the unmodified antibody heavy chain of (A)(i)(a) expressed under similar conditions.

24. The method of claim 23, wherein the amount of an antibody produced in the prokaryotic cell is at least 90% greater than the amount of the unmodified antibody heavy chain of (A)(i)(a) expressed under similar conditions.

25. The method of claim 24, wherein the amount of an antibody produced in the prokaryotic cell is at least 150% greater than the amount of the unmodified antibody heavy chain of (A)(i)(a) expressed under similar conditions.

26. The method of claim 25, wherein the amount of an antibody produced in the prokaryotic cell is at least 250% greater than the amount of the unmodified antibody heavy chain of (A)(i)(a) expressed under similar conditions.

* * * * *

UNITED STATES PATENT AND TRADEMARK OFFICE
CERTIFICATE OF CORRECTION

PATENT NO.      : 7,655,783 B2                                         Page 1 of 1
APPLICATION NO. : 11/438487
DATED           : February 2, 2010
INVENTOR(S)     : Reilly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 382 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,783 B2 | Page 1 of 1 |
| APPLICATION NO. | : 11/438487 | |
| DATED | : February 2, 2010 | |
| INVENTOR(S) | : Reilly et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this
Twenty-sixth Day of April, 2011

David J. Kappos
*Director of the United States Patent and Trademark Office*

SEQUENCE LISTING

```
<160> NUMBER OF SEQ ID NOS: 37

<210> SEQ ID NO 1
<211> LENGTH: 3300
<212> TYPE: DNA
<213> ORGANISM: Artificial Sequence
<220> FEATURE:
<223> OTHER INFORMATION: anti-TF vector

<400> SEQUENCE: 1
gaattcaact tctccatact ttggataagg aaatacagac atgaaaaatc        50
tcattgctga gttgttattt aagcttgccc aaaaagaaga agagtcgaat       100
gaactgtgtg cgcaggtaga agctttggag attatcgtca ctgcaatgct       150
tcgcaatatg gcgcaaaatg accaacagcg gttgattgat caggtagagg       200
gggcgctgta cgaggtaaag cccgatgcca gcattcctga cgacgatacg       250
gagctgctgc gcgattacgt aaagaagtta ttgaagcatc ctcgtcagta       300
aaaagttaat cttttcaaca gctgtcataa agttgtcacg gccgagactt       350
atagtcgctt tgtttttatt ttttaatgta tttgtaacta gtacgcaagt       400
tcacgtaaaa agggtatcta gaattatgaa gaagaatatc gcatttcttc       450
ttgcatctat gttcgttttt tctattgcta caaacgcgta cgctgatatc       500
cagatgaccc agtccccgag ctccctgtcc gcctctgtgg gcgatagggt       550
caccatcacc tgcagagcca gtcgcgacat caagagctat ctgaactggt       600
atcaacagaa accaggaaaa gctccgaaag tactgattta ctatgctact       650
agtctcgctg aaggagtccc ttctcgcttc tctggatccg gttctgggac       700
ggattacact ctgaccatca gcagtctgca gccagaagac ttcgcaactt       750
attactgtct tcagcacgga gagtctccat ggacatttgg acagggtacc       800
aaggtggaga tcaaacgaac tgtggctgca ccatctgtct tcatcttccc       850
gccatctgat gagcagttga aatctggaac tgcttctgtt gtgtgcctgc       900
```

-continued

| | |
|---|---|
| tgaataactt ctatcccaga gaggccaaag tacagtggaa ggtggataac | 950 |
| gccctccaat cgggtaactc ccaggagagt gtcacagagc aggacagcaa | 1000 |
| ggacagcacc tacagcctca gcagcaccct gacgctgagc aaagcagact | 1050 |
| acgagaaaca caaagtctac gcctgcgaag tcacccatca gggcctgagc | 1100 |
| tcgcccgtca caaagagctt caacagggga gagtgttaat taaatcctct | 1150 |
| acgccggacg catcgtggcg agctcggtac ccggggatct aggcctaacg | 1200 |
| ctcggttgcc gccgggcgtt ttttattgtt gccgacgcgc atctcgaatg | 1250 |
| aactgtgtgc gcaggtagaa gctttggaga ttatcgtcac tgcaatgctt | 1300 |
| cgcaatatgg cgcaaaatga ccaacagcgg ttgattgatc aggtagaggg | 1350 |
| ggcgctgtac gaggtaaagc ccgatgccag cattcctgac gacgatacgg | 1400 |
| agctgctgcg cgattacgta aagaagttat tgaagcatcc tcgtcagtaa | 1450 |
| aaagttaatc ttttcaacag ctgtcataaa gttgtcacgg ccgagactta | 1500 |
| tagtcgcttt gtttttattt tttaatgtat ttgtaactag tacgcaagtt | 1550 |
| cacgtaaaaa gggtatctag aattatgaag aagaatatcg catttcttct | 1600 |
| tgcatctatg ttcgtttttt ctattgctac aaacgcgtac gctgaggttc | 1650 |
| agctggtgga gtcggcggt ggcctggtgc agcagggg ctcactccgt | 1700 |
| ttgtcctgtg cagcttctgg cttcaatatt aaggagtact acatgcactg | 1750 |
| ggtccgtcag gccccgggta agggcctgga atgggttgga ttgattgatc | 1800 |
| cagagcaagg caacacgatc tatgacccga agttccagga ccgtgccact | 1850 |
| ataagcgctg acaattccaa aaacacagca tacctgcaga tgaacagcct | 1900 |
| gcgtgctgag gacactgccg tctattattg tgctcgagac acggccgctt | 1950 |
| acttcgacta ctgggtcaa ggaaccctgg tcaccgtctc ctcggcctcc | 2000 |
| accaagggcc catcggtctt ccccctggca ccctcctcca agagcacctc | 2050 |
| tggggcaca gcggccctgg gctgcctggt caaggactac ttccccgaac | 2100 |
| cggtgacggt gtcgtggaac tcaggcgccc tgaccagcgg cgtgcacacc | 2150 |
| ttcccggctg tcctacagtc ctcaggactc tactccctca gcagcgtggt | 2200 |
| gactgtgccc tctagcagct tgggcaccca gacctacatc tgcaacgtga | 2250 |
| atcacaagcc cagcaacacc aaggtggaca agaaagttga gcccaaatct | 2300 |
| tgtgacaaaa ctcacacatg cccaccgtgc ccagcacctg aactcctggg | 2350 |
| gggaccgtca gtcttcctct tccccccaaa acccaaggac accctcatga | 2400 |
| tctcccggac cctgaggtc acatgcgtgg tggtggacgt gagccacgaa | 2450 |
| gaccctgagg tcaagttcaa ctggtacgtg gacggcgtgg aggtgcataa | 2500 |
| tgccaagaca aagccgcggg aggagcagta caacagcacg taccgtgtgg | 2550 |
| tcagcgtcct caccgtcctg caccaggact ggctgaatgg caaggagtac | 2600 |
| aagtgcaagg tctccaacaa agccctccca gcccccatcg agaaaaccat | 2650 |
| ctccaaagcc aaagggcagc cccgagaacc acaggtgtac accctgcccc | 2700 |
| catcccggga agagatgacc aagaaccagg tcagcctgac ctgcctggtc | 2750 |
| aaaggcttct atcccagcga catcgccgtg gagtgggaga gcaatgggca | 2800 |
| gccggagaac aactacaaga ccacgcctcc cgtgctggac tccgacggct | 2850 |
| ccttcttcct ctacagcaag ctcaccgtgg acaagagcag gtggcagcag | 2900 |

```
gggaacgtct tctcatgctc cgtgatgcat gaggctctgc acaaccacta      2950
cacgcagaag agcctctccc tgtctccggg taaataagca tgcgacggcc      3000
ctagagtccc taacgctcgg ttgccgccgg gcgttttta ttgttaactc       3050 atgtttgaca gcttatcatc gataagcttt aatgcggtag tttatcacag      3100
ttaaattgct aacgcagtca ggcaccgtgt atgaaatcta acaatgcgct      3150
catcgtcatc ctcggcaccg tcaccctgga tgctgtaggc ataggcttgg      3200
ttatgccggt actgccgggc ctcttgcggg atatcgtcca ttccgacagc      3250
atcgccagtc actatggcgt gctgctagcg ctatatgcgt tgatgcaatt      3300
```

<210> SEQ ID NO 2
<211> LENGTH: 237
<212> TYPE: PRT
<213> ORGANISM: Artificial Sequence
<220> FEATURE:
<223> OTHER INFORMATION: anti-TF light chain

<400> SEQUENCE: 2

```
Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Ser Leu Ser Ala Ser Val Gly Asp Arg Val Thr Ile Thr
                 35                  40                  45

Cys Arg Ala Ser Arg Asp Ile Lys Ser Tyr Leu Asn Trp Tyr Gln
                 50                  55                  60

Gln Lys Pro Gly Lys Ala Pro Lys Val Leu Ile Tyr Tyr Ala Thr
                 65                  70                  75

Ser Leu Ala Glu Gly Val Pro Ser Arg Phe Ser Gly Ser Gly Ser
                 80                  85                  90

Gly Thr Asp Tyr Thr Leu Thr Ile Ser Ser Leu Gln Pro Glu Asp
                 95                 100                 105

Phe Ala Thr Tyr Tyr Cys Leu Gln His Gly Glu Ser Pro Trp Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
                170                 175                 180

Asn Ser Gln Glu Ser Val Thr Glu Gln Asp Ser Lys Asp Ser Thr
                185                 190                 195

Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys
                230                 235
```

<210> SEQ ID NO 3
<211> LENGTH: 470
<212> TYPE: PRT

-continued

<213> ORGANISM: Artificial Sequence
<220> FEATURE:
<223> OTHER INFORMATION: anti-TF heavy chain

<400> SEQUENCE: 3

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
                20                  25                  30

Gly Gly Gly Leu Val Gln Pro Gly Gly Ser Leu Arg Leu Ser Cys
                35                  40                  45

Ala Ala Ser Gly Phe Asn Ile Lys Glu Tyr Tyr Met His Trp Val
                50                  55                  60

Arg Gln Ala Pro Gly Lys Gly Leu Glu Trp Val Gly Leu Ile Asp
                65                  70                  75

Pro Glu Gln Gly Asn Thr Ile Tyr Asp Pro Lys Phe Gln Asp Arg
                80                  85                  90

Ala Thr Ile Ser Ala Asp Asn Ser Lys Asn Thr Ala Tyr Leu Gln
                95                 100                 105

Met Asn Ser Leu Arg Ala Glu Asp Thr Ala Val Tyr Tyr Cys Ala
               110                 115                 120

Arg Asp Thr Ala Ala Tyr Phe Asp Tyr Trp Gly Gln Gly Thr Leu
               125                 130                 135

Val Thr Val Ser Ser Ala Ser Thr Lys Gly Pro Ser Val Phe Pro
               140                 145                 150

Leu Ala Pro Ser Ser Lys Ser Thr Ser Gly Gly Thr Ala Ala Leu
               155                 160                 165

Gly Cys Leu Val Lys Asp Tyr Phe Pro Glu Pro Val Thr Val Ser
               170                 175                 180

Trp Asn Ser Gly Ala Leu Thr Ser Gly Val His Thr Phe Pro Ala
               185                 190                 195

Val Leu Gln Ser Ser Gly Leu Tyr Ser Leu Ser Ser Val Val Thr
               200                 205                 210

Val Pro Ser Ser Ser Leu Gly Thr Gln Thr Tyr Ile Cys Asn Val
               215                 220                 225

Asn His Lys Pro Ser Asn Thr Lys Val Asp Lys Lys Val Glu Pro
               230                 235                 240

Lys Ser Cys Asp Lys Thr His Thr Cys Pro Pro Cys Pro Ala Pro
               245                 250                 255

Glu Leu Leu Gly Gly Pro Ser Val Phe Leu Phe Pro Pro Lys Pro
               260                 265                 270

Lys Asp Thr Leu Met Ile Ser Arg Thr Pro Glu Val Thr Cys Val
               275                 280                 285

Val Val Asp Val Ser His Glu Asp Pro Glu Val Lys Phe Asn Trp
               290                 295                 300

Tyr Val Asp Gly Val Glu Val His Asn Ala Lys Thr Lys Pro Arg
               305                 310                 315

Glu Glu Gln Tyr Asn Ser Thr Tyr Arg Val Val Ser Val Leu Thr
               320                 325                 330

Val Leu His Gln Asp Trp Leu Asn Gly Lys Glu Tyr Lys Cys Lys
               335                 340                 345

Val Ser Asn Lys Ala Leu Pro Ala Pro Ile Glu Lys Thr Ile Ser
               350                 355                 360

Lys Ala Lys Gly Gln Pro Arg Glu Pro Gln Val Tyr Thr Leu Pro
```

```
                 365                 370                 375
Pro Ser Arg Glu Glu Met Thr Lys Asn Gln Val Ser Leu Thr Cys
            380                 385                 390

Leu Val Lys Gly Phe Tyr Pro Ser Asp Ile Ala Val Glu Trp Glu
            395                 400                 405

Ser Asn Gly Gln Pro Glu Asn Asn Tyr Lys Thr Thr Pro Pro Val
            410                 415                 420

Leu Asp Ser Asp Gly Ser Phe Phe Leu Tyr Ser Lys Leu Thr Val
            425                 430                 435

Asp Lys Ser Arg Trp Gln Gln Gly Asn Val Phe Ser Cys Ser Val
            440                 445                 450

Met His Glu Ala Leu His Asn His Tyr Thr Gln Lys Ser Leu Ser
            455                 460                 465

Leu Ser Pro Gly Lys
            470

<210> SEQ ID NO 4
<211> LENGTH: 3242
<212> TYPE: DNA
<213> ORGANISM: Artificial sequence
<220> FEATURE:
<223> OTHER INFORMATION: Anti-TF vector

<400> SEQUENCE: 4
gaattcaact tctccatact ttggataagg aaatacagac atgaaaaatc          50
tcattgctga gttgttattt aagcttgccc aaaaagaaga gagtcgaat           100 gaactgtgtg cgcaggtaga agctttggag attatcgtca ctgcaatgct          150
tcgcaatatg gcgcaaaatg accaacagcg gttgattgat caggtagagg          200
gggcgctgta cgaggtaaag cccgatgcca gcattcctga cgacgatacg          250
gagctgctgc gcgattacgt aaagaagtta ttgaagcatc ctcgtcagta          300
aaaagttaat cttttcaaca gctgtcataa agttgtcacg gccgagactt          350
atagtcgctt tgtttttatt ttttaatgta tttgtaacta gtacgcaagt          400
tcacgtaaaa agggtatcta gaattatgaa gaaaaacatc gcttttcttc          450
ttgcatctat gttcgttttt tctattgcta caaacgcgta cgctgatatc          500
cagatgaccc agtccccgag ctccctgtcc gcctctgtgg gcgatagggt          550
caccatcacc tgcagagcca gtcgcgacat caagagctat ctgaactggt          600
atcaacagaa accaggaaaa gctccgaaag tactgattta ctatgctact          650
agtctcgctg aaggagtccc ttctcgcttc tctggatccg gttctgggac          700
ggattacact ctgaccatca gcagtctgca gccagaagac ttcgcaactt          750
attactgtct tcagcacgga gagtctccat ggacatttgg acagggtacc          800
aaggtggaga tcaaacgaac tgtggctgca ccatctgtct tcatcttccc          850
gccatctgat gagcagttga aatctggaac tgcttctgtt gtgtgcctgc          900
tgaataactt ctatcccaga gaggccaaag tacagtggaa ggtggataac          950
gccctccaat cgggtaactc ccaggagagt gtcacagagc aggacagcaa          1000
ggacagcacc tacagcctca gcagcaccct gacgctgagc aaagcagact          1050
acgagaaaca caaagtctac gcctgcgaag tcacccatca gggcctgagc          1100
tcgcccgtca caaagagctt caacagggga gagtgttaat taaatcctct          1150
```

-continued

```
acgccggacg catcgtggcg agctcggtac ccggggatct aggcctaacg      1200
ctcggttgcc gccgggcgtt ttttattgtt gccgacgcgc atctcgaatg      1250
aactgtgtgc gcaggtagaa gctttggaga ttatcgtcac tgcaatgctt      1300
cgcaatatgg cgcaaaatga ccaacagcgg ttgattgatc aggtagaggg      1350
ggcgctgtac gaggtaaagc ccgatgccag cattcctgac gacgatacgg      1400
agctgctgcg cgattacgta aagaagttat tgaagcatcc tcgtcagtaa      1450
aaagttaatc ttttcaacag ctgtcataaa gttgtcacgg ccgagactta      1500
tagtcgcttt gttttatttt tttaatgtat ttgtaactag tacgcaagtt      1550
cacgtaaaaa gggtatctag aattatgaag aaaaacatcg cttttcttct      1600
tgcatctatg ttcgtttttt ctattgctac aaacgcgtac gctgaggttc      1650
agctggtgga gtctggcggt ggcctggtgc agccaggggg ctcactccgt      1700
ttgtcctgtg cagcttctgg cttcaatatt aaggagtact acatgcactg      1750
ggtccgtcag gccccgggta agggcctgga atgggttgga ttgattgatc      1800
cagagcaagg caacacgatc tatgacccga agttccagga ccgtgccact      1850
ataagcgctg acaattccaa aaacacagca tacctgcaga tgaacagcct      1900
gcgtgctgag gacactgccg tctattattg tgctcgagac acggccgctt      1950
acttcgacta ctggggtcaa ggaaccctgg tcaccgtctc ctcggcctcc      2000
accaagggcc catcggtctt ccccctggca ccctcctcca agagcacctc      2050
tgggggcaca gcggccctgg gctgcctggt caaggactac ttccccgaac      2100
cggtgacggt gtcgtggaac tcaggcgccc tgaccagcgg cgtgcacacc      2150
ttcccggctg tcctacagtc ctcaggactc tactccctca gcagcgtggt      2200
gactgtgccc tctagcagct tgggcaccca gacctacatc tgcaacgtga      2250
atcacaagcc cagcaacacc aaggtggaca agaaagttga gcccaaatct      2300
tgtgacaaaa ctcacacatg cccaccgtgc ccagcacctg aactcctggg      2350
gggaccgtca gtcttcctct tccccccaaa acccaaggac accctcatga      2400
tctcccggac ccctgaggtc acatgcgtgg tggtggacgt gagccacgaa      2450
gaccctgagg tcaagttcaa ctggtacgtg gacggcgtgg aggtgcataa      2500
tgccaagaca aagccgcggg aggagcagta caacagcacg taccgtgtgg      2550
tcagcgtcct caccgtcctg caccaggact ggctgaatgg caaggagtac      2600
aagtgcaagg tctccaacaa agccctccca gcccccatcg agaaaaccat      2650
ctccaaagcc aaagggcagc cccgagaacc acaggtgtac accctgcccc      2700
catcccggga agagatgacc aagaaccagg tcagcctgac ctgcctggtc      2750
aaaggcttct atcccagcga catcgccgtg gagtgggaga gcaatgggca      2800
gccggagaac aactacaaga ccacgcctcc cgtgctggac tccgacggct      2850
ccttcttcct ctacagcaag ctcaccgtgg acaagagcag gtggcagcag      2900
gggaacgtct tctcatgctc cgtgatgcat gaggctctgc acaaccacta      2950
cacgcagaag agcctctccc tgtctccggg taaataagca tgcgacggcc      3000
ctagagtccc taacgctcgg ttgccgccgg gcgttttttta ttgttaactc      3050
atgtttgaca gcttatcatc gataagcttt aatgcggtag tttatcacag      3100
ttaaattgct aacgcagtca ggcaccgtgt atgaaatcta acaatgcgct      3150
```
catcgtcatc tcggcaccg tcacctgga tgctgtaggc ataggcttgg          3200
ttatgccggt actgccgggc ctcttgcggg atatcgtcca tt                3242

<210> SEQ ID NO 5
<211> LENGTH: 237
<212> TYPE: PRT
<213> ORGANISM: Artificial sequence
<220> FEATURE:
<223> OTHER INFORMATION: Anti-TF light chain

<400> SEQUENCE: 5

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ala Ser Arg Asp Ile Lys Ser Tyr Leu Asn Trp Tyr Gln
                50                  55                  60

Gln Lys Pro Gly Lys Ala Pro Lys Val Leu Ile Tyr Tyr Ala Thr
                65                  70                  75

Ser Leu Ala Glu Gly Val Pro Ser Arg Phe Ser Gly Ser Gly Ser
                80                  85                  90

Gly Thr Asp Tyr Thr Leu Thr Ile Ser Ser Leu Gln Pro Glu Asp
                95                 100                 105

Phe Ala Thr Tyr Tyr Cys Leu Gln His Gly Glu Ser Pro Trp Thr
               110                 115                 120

Phe Gly Gln Gly Thr Lys Val Glu Ile Lys Arg Thr Val Ala Ala
               125                 130                 135

Pro Ser Val Phe Ile Phe Pro Pro Ser Asp Glu Gln Leu Lys Ser
               140                 145                 150

Gly Thr Ala Ser Val Val Cys Leu Leu Asn Asn Phe Tyr Pro Arg
               155                 160                 165

Glu Ala Lys Val Gln Trp Lys Val Asp Asn Ala Leu Gln Ser Gly
               170                 175                 180

Asn Ser Gln Glu Ser Val Thr Glu Gln Asp Ser Lys Asp Ser Thr
               185                 190                 195

Tyr Ser Leu Ser Ser Thr Leu Thr Leu Ser Lys Ala Asp Tyr Glu
               200                 205                 210

Lys His Lys Val Tyr Ala Cys Glu Val Thr His Gln Gly Leu Ser
               215                 220                 225

Ser Pro Val Thr Lys Ser Phe Asn Arg Gly Glu Cys
               230                 235

<210> SEQ ID NO 6
<211> LENGTH: 470
<212> TYPE: PRT
<213> ORGANISM: Artificial sequence
<220> FEATURE:
<223> OTHER INFORMATION: Anti-TF heavy chain

<400> SEQUENCE: 6

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
                20                  25                  30

-continued

```
Gly Gly Gly Leu Val Gln Pro Gly Gly Ser Leu Arg Leu Ser Cys
             35                  40                  45

Ala Ala Ser Gly Phe Asn Ile Lys Glu Tyr Tyr Met His Trp Val
             50                  55                  60

Arg Gln Ala Pro Gly Lys Gly Leu Glu Trp Val Gly Leu Ile Asp
             65                  70                  75

Pro Glu Gln Gly Asn Thr Ile Tyr Asp Pro Lys Phe Gln Asp Arg
             80                  85                  90

Ala Thr Ile Ser Ala Asp Asn Ser Lys Asn Thr Ala Tyr Leu Gln
             95                 100                 105

Met Asn Ser Leu Arg Ala Glu Asp Thr Ala Val Tyr Tyr Cys Ala
            110                 115                 120

Arg Asp Thr Ala Ala Tyr Phe Asp Tyr Trp Gly Gln Gly Thr Leu
            125                 130                 135

Val Thr Val Ser Ser Ala Ser Thr Lys Gly Pro Ser Val Phe Pro
            140                 145                 150

Leu Ala Pro Ser Ser Lys Ser Thr Ser Gly Gly Thr Ala Ala Leu
            155                 160                 165

Gly Cys Leu Val Lys Asp Tyr Phe Pro Glu Pro Val Thr Val Ser
            170                 175                 180

Trp Asn Ser Gly Ala Leu Thr Ser Gly Val His Thr Phe Pro Ala
            185                 190                 195

Val Leu Gln Ser Ser Gly Leu Tyr Ser Leu Ser Ser Val Val Thr
            200                 205                 210

Val Pro Ser Ser Ser Leu Gly Thr Gln Thr Tyr Ile Cys Asn Val
            215                 220                 225

Asn His Lys Pro Ser Asn Thr Lys Val Asp Lys Lys Val Glu Pro
            230                 235                 240

Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg
            305                 310                 315

Glu Glu Gln Tyr Asn Ser Thr Tyr Arg Val Val Ser Val Leu Thr
            320                 325                 330

Val Leu His Gln Asp Trp Leu Asn Gly Lys Glu Tyr Lys Cys Lys
            335                 340                 345

Val Ser Asn Lys Ala Leu Pro Ala Pro Ile Glu Lys Thr Ile Ser
            350                 355                 360

Lys Ala Lys Gly Gln Pro Arg Glu Pro Gln Val Tyr Thr Leu Pro
            365                 370                 375

Pro Ser Arg Glu Glu Met Thr Lys Asn Gln Val Ser Leu Thr Cys
            380                 385                 390

Leu Val Lys Gly Phe Tyr Pro Ser Asp Ile Ala Val Glu Trp Glu
            395                 400                 405

Ser Asn Gly Gln Pro Glu Asn Asn Tyr Lys Thr Thr Pro Pro Val
            410                 415                 420

Leu Asp Ser Asp Gly Ser Phe Phe Leu Tyr Ser Lys Leu Thr Val
```

```
                425                 430                 435
Asp Lys Ser Arg Trp Gln Gln Gly Asn Val Phe Ser Cys Ser Val
            440                 445                 450

Met His Glu Ala Leu His Asn His Tyr Thr Gln Lys Ser Leu Ser
            455                 460                 465

Leu Ser Pro Gly Lys
            470

<210> SEQ ID NO 7
<211> LENGTH: 3300
<212> TYPE: DNA
<213> ORGANISM: Artificial Sequence
<220> FEATURE:
<223> OTHER INFORMATION: anti-VEGF vector

<400> SEQUENCE: 7
gaattcaact ctccatact  ttggataagg aaatacagac atgaaaaatc          50
tcattgctga gttgttattt aagcttgccc aaaaagaaga agagtcgaat          100
gaactgtgtg cgcaggtaga agctttggag attatcgtca ctgcaatgct          150
tcgcaatatg gcgcaaaatg accaacagcg gttgattgat caggtagagg          200
gggcgctgta cgaggtaaag cccgatgcca gcattcctga cgacgatacg          250
gagctgctgc gcgattacgt aaagaagtta ttgaagcatc ctcgtcagta          300
aaaagttaat cttttcaaca gctgtcataa agttgtcacg gccgagactt          350
atagtcgctt tgttttttatt ttttaatgta tttgtaacta gtacgcaagt         400
tcacgtaaaa agggtatcta gaattatgaa gaagaatatc gcatttcttc          450
ttgcatctat gttcgttttt tctattgcta caaacgcgta cgctgatatc          500
cagttgaccc agtccccgag ctccctgtcc gcctctgtgg gcgatagggt          550
caccatcacc tgcagcgcaa gtcaggatat tagcaactat ttaaactggt          600
atcaacagaa accaggaaaa gctccgaaag tactgattta cttcacctcc          650
tctctccact ctggagtccc ttctcgcttc tctggatccg gttctgggac          700
ggatttcact ctgaccatca gcagtctgca gccagaagac ttcgcaactt          750
attactgtca acagtatagc accgtgccgt ggacgtttgg acagggtacc          800
aaggtggaga tcaaacgaac tgtggctgca ccatctgtct tcatcttccc          850
gccatctgat gagcagttga aatctggaac tgcttctgtt gtgtgcctgc          900
tgaataactt ctatcccaga gaggccaaag tacagtggaa ggtggataac          950
gccctccaat cgggtaactc ccaggagagt gtcacagagc aggacagcaa          1000
ggacagcacc tacagcctca gcagcaccct gacgctgagc aaagcagact          1050
acgagaaaca caaagtctac gcctgcgaag tcacccatca gggcctgagc          1100
tcgcccgtca caaagagctt caacagggga gagtgttaat aaatcctct            1150 acgccggacg catcgtggcg agctcggtac ccggggatct aggcctaacg          1200
ctcggttgcc gccgggcgtt ttttattgtt gccgacgcgc atctcgaatg          1250
aactgtgtgc gcaggtagaa gctttggaga ttatcgtcac tgcaatgctt          1300
cgcaatatgg cgcaaaatga ccaacagcgg ttgattgatc aggtagaggg          1350
ggcgctgtac gaggtaaagc ccgatgccag cattcctgac gacgatacgg          1400
agctgctgcg cgattacgta aagaagttat tgaagcatcc tcgtcagtaa          1450
```

-continued

| | |
|---|---|
| aaagttaatc ttttcaacag ctgtcataaa gttgtcacgg ccgagactta | 1500 |
| tagtcgcttt gttttatt tttaatgtat ttgtaactag tacgcaagtt | 1550 |
| cacgtaaaaa gggtatctag aattatgaag aagaatatcg catttcttct | 1600 |
| tgcatctatg ttcgtttttt ctattgctac aaacgcgtac gctgaggttc | 1650 |
| agctggtgga gtctggcggt ggcctggtgc agccaggggg ctcactccgt | 1700 |
| ttgtcctgtg cagcttctgg ctacgacttc acgcactacg gtatgaactg | 1750 |
| ggtccgtcag gccccgggta agggcctgga atgggttgga tggattaaca | 1800 |
| cctataccgg tgaaccgacc tatgctgcgg atttcaaacg tcgtttcact | 1850 |
| ttttctttag acacctccaa aagcacagca tacctgcaga tgaacagcct | 1900 |
| gcgcgctgag gacactgccg tctattactg tgcaaagtac ccgtactatt | 1950 |
| acggcacgag ccactggtat ttcgacgtct ggggtcaagg aaccctggtc | 2000 |
| accgtctcct cggcctccac caagggccca tcggtcttcc cctggcacc | 2050 |
| ctcctccaag agcacctctg ggggcacagc ggccctgggc tgcctggtca | 2100 |
| aggactactt ccccgaaccg gtgacggtgt cgtggaactc aggcgccctg | 2150 |
| accagcggcg tgcacacctt cccggctgtc ctacagtcct caggactcta | 2200 |
| ctccctcagc agcgtggtga ctgtgccctc tagcagcttg gcacccaga | 2250 |
| cctacatctg caacgtgaat cacaagccca gcaacaccaa ggtggacaag | 2300 |
| aaagttgagc ccaaatcttg tgacaaaact cacacatgcc caccgtgccc | 2350 |
| agcacctgaa ctcctggggg gaccgtcagt cttcctcttc cccccaaaac | 2400 |
| ccaaggacac cctcatgatc tcccggaccc ctgaggtcac atgcgtggtg | 2450 |
| gtggacgtga gccacgaaga ccctgaggtc aagttcaact ggtacgtgga | 2500 |
| cggcgtggag gtgcataatg ccaagacaaa gccgcgggag gagcagtaca | 2550 |
| acagcacgta ccgtgtggtc agcgtcctca ccgtcctgca ccaggactgg | 2600 |
| ctgaatggca aggagtacaa gtgcaaggtc tccaacaaag ccctcccagc | 2650 |
| ccccatcgag aaaaccatct ccaaagccaa agggcagccc cgagaaccac | 2700 |
| aggtgtacac cctgccccca tcccgggaag agatgaccaa gaaccaggtc | 2750 |
| agcctgacct gcctggtcaa aggcttctat cccagcgaca tcgccgtgga | 2800 |
| gtgggagagc aatgggcagc cggagaacaa ctacaagacc acgcctcccg | 2850 |
| tgctggactc cgacggctcc ttcttcctct acagcaagct caccgtggac | 2900 |
| aagagcaggt ggcagcaggg gaacgtcttc tcatgctccg tgatgcatga | 2950 |
| ggctctgcac aaccactaca cgcagaagag cctctccctg tctccgggta | 3000 |
| aataagcatg cgacggccct agagtcccta acgctcggtt ccgccgggc | 3050 |
| gttttttatt gttaactcat gtttgacagc ttatcatcga taagctttaa | 3100 |
| tgcggtagtt tatcacagtt aaattgctaa cgcagtcagg caccgtgtat | 3150 |
| gaaatctaac aatgcgctca tcgtcatcct cggcaccgtc accctggatg | 3200 |
| ctgtaggcat aggcttggtt atgccggtac tgccgggcct cttgcgggat | 3250 |
| atcgtccatt ccgacagcat cgccagtcac tatggcgtgc tgctagcgct | 3300 |

<210> SEQ ID NO 8
<211> LENGTH: 237
<212> TYPE: PRT
<213> ORGANISM: Artificial Sequence

```
<220> FEATURE:
<223> OTHER INFORMATION: anti-VEGF light chain

<400> SEQUENCE: 8

Met Lys Lys Asn Ile Ala Phe Leu Leu Ala Ser Met Phe Val Phe
  1               5                  10                  15

Ser Ile Ala Thr Asn Ala Tyr Ala Asp Ile Gln Leu Thr Gln Ser
                 20                  25                  30

Pro Ser Ser Leu Ser Ala Ser Val Gly Asp Arg Val Thr Ile Thr
                 35                  40                  45

Cys Ser Ala Ser Gln Asp Ile Ser Asn Tyr Leu Asn Trp Tyr Gln
                 50                  55                  60

Gln Lys Pro Gly Lys Ala Pro Lys Val Leu Ile Tyr Phe Thr Ser
                 65                  70                  75

Ser Leu His Ser Gly Val Pro Ser Arg Phe Ser Gly Ser Gly Ser
                 80                  85                  90

Gly Thr Asp Phe Thr Leu Thr Ile Ser Ser Leu Gln Pro Glu Asp
                 95                 100                 105

Phe Ala Thr Tyr Tyr Cys Gln Gln Tyr Ser Thr Val Pro Trp Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
                170                 175                 180

Asn Ser Gln Glu Ser Val Thr Glu Gln Asp Ser Lys Asp Ser Thr
                185                 190                 195

Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys
                230                 235

<210> SEQ ID NO 9
<211> LENGTH: 476
<212> TYPE: PRT
<213> ORGANISM: Artificial Sequence
<220> FEATURE:
<223> OTHER INFORMATION: anti-VEGF heavy chain

<400> SEQUENCE: 9

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Ala Ser Gly Tyr Asp Phe Thr His Tyr Gly Met Asn Trp Val
                 50                  55                  60

Arg Gln Ala Pro Gly Lys Gly Leu Glu Trp Val Gly Trp Ile Asn
                 65                  70                  75

Thr Tyr Thr Gly Glu Pro Thr Tyr Ala Ala Asp Phe Lys Arg Arg
```

```
                80                  85                  90
Phe Thr Phe Ser Leu Asp Thr Ser Lys Ser Thr Ala Tyr Leu Gln
                95                 100                 105
Met Asn Ser Leu Arg Ala Glu Asp Thr Ala Val Tyr Tyr Cys Ala
               110                 115                 120
Lys Tyr Pro Tyr Tyr Gly Thr Ser His Trp Tyr Phe Asp Val
               125                 130                 135
Trp Gly Gln Gly Thr Leu Val Thr Val Ser Ser Ala Ser Thr Lys
               140                 145                 150
Gly Pro Ser Val Phe Pro Leu Ala Pro Ser Ser Lys Ser Thr Ser
               155                 160                 165
Gly Gly Thr Ala Ala Leu Gly Cys Leu Val Lys Asp Tyr Phe Pro
               170                 175                 180
Glu Pro Val Thr Val Ser Trp Asn Ser Gly Ala Leu Thr Ser Gly
               185                 190                 195
Val His Thr Phe Pro Ala Val Leu Gln Ser Ser Gly Leu Tyr Ser
               200                 205                 210
Leu Ser Ser Val Val Thr Val Pro Ser Ser Ser Leu Gly Thr Gln
               215                 220                 225
Thr Tyr Ile Cys Asn Val Asn His Lys Pro Ser Asn Thr Lys Val
               230                 235                 240
Asp Lys Lys Val Glu Pro Lys Ser Cys Asp Lys Thr His Thr Cys
               245                 250                 255
Pro Pro Cys Pro Ala Pro Glu Leu Leu Gly Gly Pro Ser Val Phe
               260                 265                 270
Leu Phe Pro Pro Lys Pro Lys Asp Thr Leu Met Ile Ser Arg Thr
               275                 280                 285
Pro Glu Val Thr Cys Val Val Val Asp Val Ser His Glu Asp Pro
               290                 295                 300
Glu Val Lys Phe Asn Trp Tyr Val Asp Gly Val Glu Val His Asn
               305                 310                 315
Ala Lys Thr Lys Pro Arg Glu Glu Gln Tyr Asn Ser Thr Tyr Arg
               320                 325                 330
Val Val Ser Val Leu Thr Val Leu His Gln Asp Trp Leu Asn Gly
               335                 340                 345
Lys Glu Tyr Lys Cys Lys Val Ser Asn Lys Ala Leu Pro Ala Pro
               350                 355                 360
Ile Glu Lys Thr Ile Ser Lys Ala Lys Gly Gln Pro Arg Glu Pro
               365                 370                 375
Gln Val Tyr Thr Leu Pro Pro Ser Arg Glu Glu Met Thr Lys Asn
               380                 385                 390
Gln Val Ser Leu Thr Cys Leu Val Lys Gly Phe Tyr Pro Ser Asp
               395                 400                 405
Ile Ala Val Glu Trp Glu Ser Asn Gly Gln Pro Glu Asn Asn Tyr
               410                 415                 420
Lys Thr Thr Pro Pro Val Leu Asp Ser Asp Gly Ser Phe Phe Leu
               425                 430                 435
Tyr Ser Lys Leu Thr Val Asp Lys Ser Arg Trp Gln Gln Gly Asn
               440                 445                 450
Val Phe Ser Cys Ser Val Met His Glu Ala Leu His Asn His Tyr
               455                 460                 465
Thr Gln Lys Ser Leu Ser Leu Ser Pro Gly Lys
               470                 475
```

<210> SEQ ID NO 10
<211> LENGTH: 3255
<212> TYPE: DNA
<213> ORGANISM: Artificial sequence
<220> FEATURE:
<223> OTHER INFORMATION: Anti-VEGF vector

<400> SEQUENCE: 10

| | |
|---|---|
| gaattcaact tctccatact ttggataagg aaatacagac atgaaaaatc | 50 |
| tcattgctga gttgttattt aagcttgccc aaaaagaaga agagtcgaat | 100 |
| gaactgtgtg cgcaggtaga agctttggag attatcgtca ctgcaatgct | 150 |
| tcgcaatatg gcgcaaaatg accaacagcg gttgattgat caggtagagg | 200 |
| gggcgctgta cgaggtaaag cccgatgcca gcattcctga cgacgatacg | 250 |
| gagctgctgc gcgattacgt aaagaagtta ttgaagcatc ctcgtcagta | 300 |
| aaaagttaat cttttcaaca gctgtcataa agttgtcacg gccgagactt | 350 |
| atagtcgctt tgttttatt ttttaatgta tttgtaacta gtacgcaagt | 400 |
| tcacgtaaaa agggtatcta gaattatgaa gaagaatatc gcatttcttc | 450 |
| ttgcatctat gttcgttttt tctattgcta caaacgcgta cgctgatatc | 500 |
| cagttgaccc agtccccgag ctccctgtcc gcctctgtgg gcgatagggt | 550 |
| caccatcacc tgcagcgcaa gtcaggatat tagcaactat ttaaactggt | 600 |
| atcaacagaa accaggaaaa gctccgaaag tactgattta cttcacctcc | 650 |
| tctctccact ctggagtccc ttctcgcttc tctggatccg ttctgggac | 700 |
| ggatttcact ctgaccatca gcagtctgca gccagaagac ttcgcaactt | 750 |
| attactgtca acagtatagc accgtgccgt ggacgtttgg acagggtacc | 800 |
| aaggtggaga tcaaacgaac tgtggctgca ccatctgtct tcatcttccc | 850 |
| gccatctgat gagcagttga aatctggaac tgcttctgtt gtgtgcctgc | 900 |
| tgaataactt ctatcccaga gaggccaaag tacagtggaa ggtggataac | 950 |
| gccctccaat cgggtaactc ccaggagagt gtcacagagc aggacagcaa | 1000 |
| ggacagcacc tacagcctca gcagcaccct gacgctgagc aaagcagact | 1050 |
| acgagaaaca caaagtctac gcctgcgaag tcacccatca gggcctgagc | 1100 |
| tcgcccgtca caaagagctt caacagggga gagtgttaat taaatcctct | 1150 |
| acgccggacg catcgtggcg agctcggtac ccggggatct aggcctaacg | 1200 |
| ctcggttgcc gccgggcgtt ttttattgtt gccgacgcgc atctcgaatg | 1250 |
| aactgtgtgc gcaggtagaa gctttggaga ttatcgtcac tgcaatgctt | 1300 |
| cgcaatatgg cgcaaaatga ccaacagcgg ttgattgatc aggtagaggg | 1350 |
| ggcgctgtac gaggtaaagc ccgatgccag cattcctgac gacgatacgg | 1400 |
| agctgctgcg cgattacgta aagaagttat tgaagcatcc tcgtcagtaa | 1450 |
| aaagttaatc ttttcaacag ctgtcataaa gttgtcacgg ccgagactta | 1500 |
| tagtcgcttt gttttattt tttaatgtat tgtaactag tacgcaagtt | 1550 |
| cacgtaaaaa gggtatctag aattatgaag aagaatatcg catttcttct | 1600 |
| tgcatctatg ttcgtttttt ctattgctac aaacgcgtac gctgaggttc | 1650 |
| agctggtgga gtctggcggt ggcctggtgc agccaggggg ctcactccgt | 1700 |

-continued

```
ttgtcctgtg cagcttctgg ctataccttc accaactatg gtataaactg      1750
ggtccgtcag gccccgggta agggcctgga atgggttgga tggattaaca      1800
cctataccgg tgaaccgacc tatgctgcgg atttcaaacg tcgtttcact      1850
ttttctttag acacctccaa aagcacagca tacctgcaga tgaacagcct      1900
gcgcgctgag acactgccg tctattactg tgcaaagtac ccgcactatt       1950
atgtgaacga gcggaagagc cactggtatt tcgacgtctg gggtcaagga      2000
accctggtca ccgtctcctc ggcctccacc aagggcccat cggtcttccc      2050
cctggcaccc tcctccaaga gcacctctgg gggcacagcg gccctgggct      2100
gcctggtcaa ggactacttc cccgaaccgg tgacggtgtc gtggaactca      2150
ggcgccctga ccagcggcgt gcacaccttc ccggctgtcc tacagtcctc      2200
aggactctac tccctcagca gcgtggtgac tgtgccctct agcagcttgg      2250
gcacccagac ctacatctgc aacgtgaatc acaagcccag caacaccaag      2300
gtggacaaga agttgagcc caaatcttgt gacaaaactc acacatgccc       2350
accgtgccca gcacctgaac tcctgggggg accgtcagtc ttcctcttcc      2400
ccccaaaacc caaggacacc ctcatgatct cccggacccc tgaggtcaca      2450
tgcgtggtgg tggacgtgag ccacgaagac cctgaggtca agttcaactg      2500
gtacgtggac ggcgtggagg tgcataatgc caagacaaag ccgcgggagg      2550
agcagtacaa cagcacgtac cgtgtggtca gcgtcctcac cgtcctgcac      2600
caggactggc tgaatggcaa ggagtacaag tgcaaggtct ccaacaaagc      2650
cctcccagcc cccatcgaga aaaccatctc caaagccaaa gggcagcccc      2700
gagaaccaca ggtgtacacc ctgccccat cccgggaaga gatgaccaag       2750
aaccaggtca gcctgacctg cctggtcaaa ggcttctatc ccagcgacat      2800
cgccgtggag tgggagagca atgggcagcc ggagaacaac tacaagacca      2850
cgcctcccgt gctggactcc gacggctcct tcttcctcta cagcaagctc      2900
accgtggaca agagcaggtg gcagcagggg aacgtcttct catgctccgt      2950
gatgcatgag gctctgcaca accactacac gcagaagagc ctctccctgt      3000
ctccgggtaa ataagcatgc gacggcccta gagtccctaa cgctcggttg      3050
ccgccgggcg ttttttattg ttaactcatg tttgacagct tatcatcgat      3100
aagctttaat gcggtagttt atcacagtta aattgctaac gcagtcaggc      3150
accgtgtatg aaatctaaca atgcgctcat cgtcatcctc ggcaccgtca      3200
ccctggatgc tgtaggcata ggcttggtta tgccggtact gccgggcctc      3250
ttgcg                                                        3255
```

<210> SEQ ID NO 11
<211> LENGTH: 237
<212> TYPE: PRT
<213> ORGANISM: Artificial sequence
<220> FEATURE:
<223> OTHER INFORMATION: Anti-VEGF light chain

<400> SEQUENCE: 11

```
Met Lys Lys Asn Ile Ala Phe Leu Leu Ala Ser Met Phe Val Phe
  1               5                  10                  15

Ser Ile Ala Thr Asn Ala Tyr Ala Asp Ile Gln Leu Thr Gln Ser
             20                  25                  30
```

```
Pro Ser Ser Leu Ser Ala Ser Val Gly Asp Arg Val Thr Ile Thr
            35                  40                  45

Cys Ser Ala Ser Gln Asp Ile Ser Asn Tyr Leu Asn Trp Tyr Gln
        50                  55                  60

Gln Lys Pro Gly Lys Ala Pro Lys Val Leu Ile Tyr Phe Thr Ser
            65                  70                  75

Ser Leu His Ser Gly Val Pro Ser Arg Phe Ser Gly Ser Gly Ser
        80                  85                  90

Gly Thr Asp Phe Thr Leu Thr Ile Ser Ser Leu Gln Pro Glu Asp
            95                 100                 105

Phe Ala Thr Tyr Tyr Cys Gln Gln Tyr Ser Thr Val Pro Trp Thr
           110                 115                 120

Phe Gly Gln Gly Thr Lys Val Glu Ile Lys Arg Thr Val Ala Ala
           125                 130                 135

Pro Ser Val Phe Ile Phe Pro Pro Ser Asp Glu Gln Leu Lys Ser
           140                 145                 150

Gly Thr Ala Ser Val Val Cys Leu Leu Asn Asn Phe Tyr Pro Arg
           155                 160                 165

Glu Ala Lys Val Gln Trp Lys Val Asp Asn Ala Leu Gln Ser Gly
           170                 175                 180

Asn Ser Gln Glu Ser Val Thr Glu Gln Asp Ser Lys Asp Ser Thr
           185                 190                 195

Tyr Ser Leu Ser Ser Thr Leu Thr Leu Ser Lys Ala Asp Tyr Glu
           200                 205                 210

Lys His Lys Val Tyr Ala Cys Glu Val Thr His Gln Gly Leu Ser
           215                 220                 225

Ser Pro Val Thr Lys Ser Phe Asn Arg Gly Glu Cys
           230                 235

<210> SEQ ID NO 12
<211> LENGTH: 479
<212> TYPE: PRT
<213> ORGANISM: Artificial sequence
<220> FEATURE:
<223> OTHER INFORMATION: Anti-VEGF heavy chain

<400> SEQUENCE: 12

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
             20                  25                  30

Gly Gly Gly Leu Val Gln Pro Gly Gly Ser Leu Arg Leu Ser Cys
         35                  40                  45

Ala Ala Ser Gly Tyr Thr Phe Thr Asn Tyr Gly Ile Asn Trp Val
         50                  55                  60

Arg Gln Ala Pro Gly Lys Gly Leu Glu Trp Val Gly Trp Ile Asn
         65                  70                  75

Thr Tyr Thr Gly Glu Pro Thr Tyr Ala Ala Asp Phe Lys Arg Arg
         80                  85                  90

Phe Thr Phe Ser Leu Asp Thr Ser Lys Ser Thr Ala Tyr Leu Gln
         95                 100                 105

Met Asn Ser Leu Arg Ala Glu Asp Thr Ala Val Tyr Tyr Cys Ala
        110                 115                 120

Lys Tyr Pro His Tyr Tyr Val Asn Glu Arg Lys Ser His Trp Tyr
        125                 130                 135
```

Phe Asp Val Trp Gly Gln Gly Thr Leu Val Thr Val Ser Ser Ala
            140                 145                 150

Ser Thr Lys Gly Pro Ser Val Phe Pro Leu Ala Pro Ser Ser Lys
            155                 160                 165

Ser Thr Ser Gly Gly Thr Ala Ala Leu Gly Cys Leu Val Lys Asp
            170                 175                 180

Tyr Phe Pro Glu Pro Val Thr Val Ser Trp Asn Ser Gly Ala Leu
            185                 190                 195

Thr Ser Gly Val His Thr Phe Pro Ala Val Leu Gln Ser Ser Gly
            200                 205                 210

Leu Tyr Ser Leu Ser Ser Val Val Thr Val Pro Ser Ser Ser Leu
            215                 220                 225

Gly Thr Gln Thr Tyr Ile Cys Asn Val Asn His Lys Pro Ser Asn
            230                 235                 240

Thr Lys Val Asp Lys Lys Val Glu Pro Lys Ser Cys Asp Lys Thr
            245                 250                 255

His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu
            305                 310                 315

Val His Asn Ala Lys Thr Lys Pro Arg Glu Glu Gln Tyr Asn Ser
            320                 325                 330

Thr Tyr Arg Val Val Ser Val Leu Thr Val Leu His Gln Asp Trp
            335                 340                 345

Leu Asn Gly Lys Glu Tyr Lys Cys Lys Val Ser Asn Lys Ala Leu
            350                 355                 360

Pro Ala Pro Ile Glu Lys Thr Ile Ser Lys Ala Lys Gly Gln Pro
            365                 370                 375

Arg Glu Pro Gln Val Tyr Thr Leu Pro Pro Ser Arg Glu Glu Met
            380                 385                 390

Thr Lys Asn Gln Val Ser Leu Thr Cys Leu Val Lys Gly Phe Tyr
            395                 400                 405

Pro Ser Asp Ile Ala Val Glu Trp Glu Ser Asn Gly Gln Pro Glu
            410                 415                 420

Asn Asn Tyr Lys Thr Thr Pro Pro Val Leu Asp Ser Asp Gly Ser
            425                 430                 435

Phe Phe Leu Tyr Ser Lys Leu Thr Val Asp Lys Ser Arg Trp Gln
            440                 445                 450

Gln Gly Asn Val Phe Ser Cys Ser Val Met His Glu Ala Leu His
            455                 460                 465

Asn His Tyr Thr Gln Lys Ser Leu Ser Leu Ser Pro Gly Lys
            470                 475

<210> SEQ ID NO 13
<211> LENGTH: 1139
<212> TYPE: DNA
<213> ORGANISM: Artificial sequence
<220> FEATURE:
<223> OTHER INFORMATION: Synthetic

<400> SEQUENCE: 13

```
atcgatgaat tcatgctgtg gtgtcatggt cggtgatcgc cagggtgccg      50
acgcgcatct cgactgcacg gtgcaccaat gcttctggcg tcaggcagcc     100
atcggaagct gtggtatggc tgtgcaggtc gtaaatcact gcataattcg     150
tgtcgctcaa ggcgcactcc cgttctggat aatgttttt gcgccgacat      200
cataacggtt ctggcaaata ttctgaaatg agctgttgac aattaatcat     250
cgaactagtt taatgtgtgg aattgtgagc ggataacaat taagcttagg     300
attctagagg gaagatttat gaaatcactg tttaaagtaa cgctgctggc     350
gaccacaatg gccgttgccc tgcatgcacc aatcactttt gctgctgaag     400
ctgcaaaacc tgctacagct gctgacagca agcagcgtt caaaaatgac       450
gatcagaaat cagcttatgc actgggtgcc tcgctgggtc gttacatgga     500
aaactctcta aaagaacaag aaaaactggg catcaaactg gataaagatc     550
agctgatcgc tggtgttcag gatgcatttg ctgataagag caaactctcc     600
gaccaagaga tcgaacagac tctacaagca ttcgaagctc gcgtgaagtc     650
ttctgctcag gcgaagatgg aaaaagacgc ggctgataac gaagcaaaag     700
gtaaagagta ccgcgagaaa tttgccaaag agaaaggtgt gaaaacctct     750
tcaactggtc tggtttatca ggtagtagaa gccggtaaag gcgaagcacc     800
gaaagacagc gatactgttg tagtgaacta caaaggtacg ctgatcgacg     850
gtaaagagtt cgacaactct tacacccgtg gtgaaccgct ttctttccgt     900
ctggacggtg ttatcccggg ttggacagaa ggtctgaaga acatcaagaa     950
aggcggtaag atcaaactgg ttattccacc agaactggct tacggcaaag    1000
cgggtgttcc ggggatccca ccgaattcta ccctggtgtt tgacgtagag    1050
ctgctggatg tgaaaccagc gccgaaggct gatgcaaagc cggaagctga    1100
tgcgaaagcc gcagattctg ctaaaaaata aaagctagc                1139
```

<210> SEQ ID NO 14
<211> LENGTH: 1139
<212> TYPE: DNA
<213> ORGANISM: Artificial Sequence
<220> FEATURE:
<223> OTHER INFORMATION: Synthetic
<400> SEQUENCE: 14

```
tagctactta agtacgacac cacagtacca gccactagcg gtcccacggc       50
tgcgcgtaga gctgacgtgc cacgtggtta cgaagaccgc agtccgtcgg      100
tagccttcga caccataccg acacgtccag catttagtga cgtattaagc      150
acagcgagtt ccgcgtgagg gcaagaccta ttacaaaaaa cgcggctgta      200
gtattgccaa gaccgtttat aagactttac tcgacaactg ttaattagta      250
gcttgatcaa attacacacc ttaacactcg cctattgtta attcgaatcc      300
taagatctcc cttctaaata ctttagtgac aaatttcatt gcgacgaccg      350
ctggtgttac cggcaacggg acgtacgtgg ttagtgaaaa cgacgacttc      400
gacgttttgg acgatgtcga cgactgtcgt ttcgtcgcaa gttttttactg     450
ctagtcttta gtcgaatacg tgacccacgg agcgacccag caatgtacct      500
tttgagagat tttcttgttc ttttttgaccc gtagtttgac ctatttctag    550
```

-continued

```
tcgactagcg accacaagtc ctacgtaaac gactattctc gtttgagagg         600
ctggttctct agcttgtctg agatgttcgt aagcttcgag cgcacttcag         650
aagacgagtc cgcttctacc tttttctgcg ccgactattg cttcgttttc         700
catttctcat ggcgctcttt aaacggtttc tctttccaca cttttggaga         750
agttgaccag accaaatagt ccatcatctt cggccatttc cgcttcgtgg         800
ctttctgtcg ctatgacaac atcacttgat gtttccatgc gactagctgc         850
catttctcaa gctgttgaga atgtgggcac cacttggcga agaaaggca          900 gacctgccac aatagggccc aacctgtctt ccagacttct tgtagttctt         950
tccgccattc tagtttgacc aataaggtgg tcttgaccga atgccgtttc         1000
gcccacaagg cccctagggt ggcttaagat gggaccacaa actgcatctc         1050
gacgacctac actttggtcg cggcttccga ctacgtttcg gccttcgact         1100
acgctttcgg cgtctaagac gattttttat tttcgatcg                     1139
```

<210> SEQ ID NO 15
<211> LENGTH: 270
<212> TYPE: PRT
<213> ORGANISM: E. coli

<400> SEQUENCE: 15

```
Met Lys Ser Leu Phe Lys Val Thr Leu Leu Ala Thr Thr Met Ala
 1               5                  10                  15

Val Ala Leu His Ala Pro Ile Thr Phe Ala Ala Glu Ala Ala Lys
                20                  25                  30

Pro Ala Thr Ala Ala Asp Ser Lys Ala Ala Phe Lys Asn Asp Asp
                35                  40                  45

Gln Lys Ser Ala Tyr Ala Leu Gly Ala Ser Leu Gly Arg Tyr Met
                50                  55                  60

Glu Asn Ser Leu Lys Glu Gln Glu Lys Leu Gly Ile Lys Leu Asp
                65                  70                  75

Lys Asp Gln Leu Ile Ala Gly Val Gln Asp Ala Phe Ala Asp Lys
                80                  85                  90

Ser Lys Leu Ser Asp Gln Glu Ile Glu Gln Thr Leu Gln Ala Phe
                95                 100                 105

Glu Ala Arg Val Lys Ser Ser Ala Gln Ala Lys Met Glu Lys Asp
               110                 115                 120

Ala Ala Asp Asn Glu Ala Lys Gly Lys Glu Tyr Arg Glu Lys Phe
               125                 130                 135

Ala Lys Glu Lys Gly Val Lys Thr Ser Ser Thr Gly Val Leu Tyr
               140                 145                 150

Gln Val Val Glu Ala Gly Lys Gly Glu Ala Pro Lys Asp Ser Asp
               155                 160                 165

Thr Val Val Asn Tyr Lys Gly Thr Leu Ile Asp Gly Lys Glu
               170                 175                 180

Phe Asp Asn Ser Tyr Thr Arg Gly Glu Pro Leu Ser Phe Arg Leu
               185                 190                 195

Asp Gly Val Ile Pro Gly Trp Thr Glu Gly Leu Lys Asn Ile Lys
               200                 205                 210

Lys Gly Gly Lys Ile Lys Leu Val Ile Pro Glu Leu Ala Tyr
               215                 220                 225

Gly Lys Ala Gly Val Pro Gly Ile Pro Pro Asn Ser Thr Leu Val
               230                 235                 240
```

Phe Asp Val Glu Leu Leu Asp Val Lys Pro Ala Pro Lys Ala Asp
               245                 250                 255

Ala Lys Pro Glu Ala Asp Ala Lys Ala Ala Asp Ser Ala Lys Lys
               260                 265                 270

<210> SEQ ID NO 16
<211> LENGTH: 3000
<212> TYPE: DNA
<213> ORGANISM: Artificial sequence
<220> FEATURE:
<223> OTHER INFORMATION: Anti-TF vector

<400> SEQUENCE: 16

| | | |
|---|---|---|
| gaattcaact tctccatact ttggataagg aaatacagac atgaaaaatc | 50 |
| tcattgctga gttgttattt aagcttgccc aaaaagaaga agagtcgaat | 100 |
| gaactgtgtg cgcaggtaga agctttggag attatcgtca ctgcaatgct | 150 |
| tcgcaatatg gcgcaaaatg accaacagcg gttgattgat caggtagagg | 200 |
| gggcgctgta cgaggtaaag cccgatgcca gcattcctga cgacgatacg | 250 |
| gagctgctgc gcgattacgt aaagaagtta ttgaagcatc ctcgtcagta | 300 |
| aaaagttaat cttttcaaca gctgtcataa agttgtcacg gccgagactt | 350 |
| atagtcgctt tgttttatt ttttaatgta tttgtaacta gtacgcaagt | 400 |
| tcacgtaaaa agggtatcta gaattatgaa aaagaatatc gcatttcttc | 450 |
| ttgcatctat gttcgttttt tctattgcta caaacgcgta cgctgatatc | 500 |
| cagatgaccc agtccccgag ctccctgtcc gcctctgtgg gcgatagggt | 550 |
| caccatcacc tgcagagcca gtcgcgacat caagagctat ctgaactggt | 600 |
| atcaacagaa accaggaaaa gctccgaaag tactgattta ctatgctact | 650 |
| agtctcgctg aaggagtccc ttctcgcttc tctggatccg gttctgggac | 700 |
| ggattacact ctgaccatca gcagtctgca gccagaagac ttcgcaactt | 750 |
| attactgtct tcagcacgga gagtctccat ggacatttgg acagggtacc | 800 |
| aaggtggaga tcaaacgaac tgtggctgca ccatctgtct tcatcttccc | 850 |
| gccatctgat gagcagttga aatctggaac tgcttctgtt gtgtgcctgc | 900 |
| tgaataactt ctatcccaga gaggccaaag tacagtggaa ggtggataac | 950 |
| gccctccaat cgggtaactc ccaggagagt gtcacagagc aggacagcaa | 1000 |
| ggacagcacc tacagcctca gcagcaccct gacgctgagc aaagcagact | 1050 |
| acgagaaaca caaagtctac gcctgcgaag tcacccatca gggcctgagc | 1100 |
| tcgcccgtca caaagagctt caacagggga gagtgttaat taaatcctct | 1150 |
| acgccggacg catcgtggcg agctcggtac ccggggatct aggcctaacg | 1200 |
| ctcggttgcc gccgggcgtt ttttattgtt gccgacgcgc atctcgactg | 1250 |
| cacggtgcac caatgcttct ggcgtcaggc agccatcgga agctgtggta | 1300 |
| tggctgtgca ggtcgtaaat cactgcataa ttcgtgtcgc tcaaggcgca | 1350 |
| ctcccgttct ggataatgtt ttttgcgccg acatcataac ggttctggca | 1400 |
| aatattctga aatgagctgt tgacaattaa tcatcgaact agtttaatgt | 1450 |
| gtggaattgt gagcggataa caattaagct taggatctag aattatgaag | 1500 |
| aagaatattg cgttcctact tgcctctatg tttgtctttt ctatagctac | 1550 |

|  |  |
|---|---|
| aaacgcgtac gctgaggttc agctggtgga gtctggcggt ggcctggtgc | 1600 |
| agccaggggg ctcactccgt tgtcctgtg cagcttctgg cttcaatatt | 1650 |
| aaggagtact acatgcactg ggtccgtcag gccccgggta agggcctgga | 1700 |
| atgggttgga ttgattgatc cagagcaagg caacacgatc tatgacccga | 1750 |
| agttccagga ccgtgccact ataagcgctg acaattccaa aaacacagca | 1800 |
| tacctgcaga tgaacagcct gcgtgctgag gacactgccg tctattattg | 1850 |
| tgctcgagac acggccgctt acttcgacta ctggggtcaa ggaaccctgg | 1900 |
| tcaccgtctc ctcggcctcc accaagggcc catcggtctt ccccctggca | 1950 |
| ccctcctcca agagcacctc tgggggcaca gcggccctgg gctgcctggt | 2000 |
| caaggactac ttccccgaac cggtgacggt gtcgtggaac tcaggcgccc | 2050 |
| tgaccagcgg cgtgcacacc ttcccggctg tcctacagtc ctcaggactc | 2100 |
| tactccctca gcagcgtggt gactgtgccc tctagcagct gggcaccca | 2150 |
| gacctacatc tgcaacgtga atcacaagcc cagcaacacc aaggtggaca | 2200 |
| agaaagttga gcccaaatct tgtgacaaaa ctcacacatg cccaccgtgc | 2250 |
| ccagcacctg aactcctggg gggaccgtca gtcttcctct tccccccaaa | 2300 |
| acccaaggac accctcatga tctcccggac ccctgaggtc acatgcgtgg | 2350 |
| tggtggacgt gagccacgaa gaccctgagg tcaagttcaa ctggtacgtg | 2400 |
| gacggcgtgg aggtgcataa tgccaagaca aagccgcggg aggagcagta | 2450 |
| caacagcacg taccgtgtgg tcagcgtcct caccgtcctg caccaggact | 2500 |
| ggctgaatgg caaggagtac aagtgcaagg tctccaacaa agccctccca | 2550 |
| gcccccatcg agaaaaccat ctccaaagcc aaagggcagc cccgagaacc | 2600 |
| acaggtgtac accctgcccc catcccggga agagatgacc aagaaccagg | 2650 |
| tcagcctgac ctgcctggtc aaaggcttct atcccagcga catcgccgtg | 2700 |
| gagtgggaga gcaatgggca gccggagaac aactacaaga ccacgcctcc | 2750 |
| cgtgctggac tccgacggct ccttcttcct ctacagcaag ctcaccgtgg | 2800 |
| acaagagcag gtggcagcag gggaacgtct tctcatgctc cgtgatgcat | 2850 |
| gaggctctgc acaaccacta cacgcagaag agcctctccc tgtctccggg | 2900 |
| taaataagca tgcgacggcc ctagagtccc taacgctcgg ttgccgccgg | 2950 |
| gcgttttta ttgttaactc atgtttgaca gcttatcatc gataagcttt | 3000 |

<210> SEQ ID NO 17
<211> LENGTH: 237
<212> TYPE: PRT
<213> ORGANISM: Artificial sequence
<220> FEATURE:
<223> OTHER INFORMATION: Anti-TF light chain

<400> SEQUENCE: 17

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ala Ser Arg Asp Ile Lys Ser Tyr Leu Asn Trp Tyr Gln
                50                  55                  60

Gln Lys Pro Gly Lys Ala Pro Lys Val Leu Ile Tyr Tyr Ala Thr
            65                  70                  75

Ser Leu Ala Glu Gly Val Pro Ser Arg Phe Ser Gly Ser Gly Ser
            80                  85                  90

Gly Thr Asp Tyr Thr Leu Thr Ile Ser Ser Leu Gln Pro Glu Asp
            95                 100                 105

Phe Ala Thr Tyr Tyr Cys Leu Gln His Gly Glu Ser Pro Trp Thr
           110                 115                 120

Phe Gly Gln Gly Thr Lys Val Glu Ile Lys Arg Thr Val Ala Ala
           125                 130                 135

Pro Ser Val Phe Ile Phe Pro Pro Ser Asp Glu Gln Leu Lys Ser
           140                 145                 150

Gly Thr Ala Ser Val Val Cys Leu Leu Asn Asn Phe Tyr Pro Arg
           155                 160                 165

Glu Ala Lys Val Gln Trp Lys Val Asp Asn Ala Leu Gln Ser Gly
           170                 175                 180

Asn Ser Gln Glu Ser Val Thr Glu Gln Asp Ser Lys Asp Ser Thr
           185                 190                 195

Tyr Ser Leu Ser Ser Thr Leu Thr Leu Ser Lys Ala Asp Tyr Glu
           200                 205                 210

Lys His Lys Val Tyr Ala Cys Glu Val Thr His Gln Gly Leu Ser
           215                 220                 225

Ser Pro Val Thr Lys Ser Phe Asn Arg Gly Glu Cys
           230                 235

<210> SEQ ID NO 18
<211> LENGTH: 470
<212> TYPE: PRT
<213> ORGANISM: Artificial sequence
<220> FEATURE:
<223> OTHER INFORMATION: Anti-TF heavy chain

<400> SEQUENCE: 18

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
            20                  25                  30

Gly Gly Gly Leu Val Gln Pro Gly Gly Ser Leu Arg Leu Ser Cys
            35                  40                  45

Ala Ala Ser Gly Phe Asn Ile Lys Glu Tyr Tyr Met His Trp Val
            50                  55                  60

Arg Gln Ala Pro Gly Lys Gly Leu Glu Trp Val Gly Leu Ile Asp
            65                  70                  75

Pro Glu Gln Gly Asn Thr Ile Tyr Asp Pro Lys Phe Gln Asp Arg
            80                  85                  90

Ala Thr Ile Ser Ala Asp Asn Ser Lys Asn Thr Ala Tyr Leu Gln
            95                 100                 105

Met Asn Ser Leu Arg Ala Glu Asp Thr Ala Val Tyr Tyr Cys Ala
           110                 115                 120

Arg Asp Thr Ala Ala Tyr Phe Asp Tyr Trp Gly Gln Gly Thr Leu
           125                 130                 135

Val Thr Val Ser Ser Ala Ser Thr Lys Gly Pro Ser Val Phe Pro
           140                 145                 150

Leu Ala Pro Ser Ser Lys Ser Thr Ser Gly Gly Thr Ala Ala Leu
           155                 160                 165

```
Gly Cys Leu Val Lys Asp Tyr Phe Pro Glu Pro Val Thr Val Ser
                170                 175                 180

Trp Asn Ser Gly Ala Leu Thr Ser Gly Val His Thr Phe Pro Ala
            185                 190                 195

Val Leu Gln Ser Ser Gly Leu Tyr Ser Leu Ser Ser Val Val Thr
        200                 205                 210

Val Pro Ser Ser Ser Leu Gly Thr Gln Thr Tyr Ile Cys Asn Val
    215                 220                 225

Asn His Lys Pro Ser Asn Thr Lys Val Asp Lys Lys Val Glu Pro
230                 235                 240

Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg
305                 310                 315

Glu Glu Gln Tyr Asn Ser Thr Tyr Arg Val Val Ser Val Leu Thr
                320                 325                 330

Val Leu His Gln Asp Trp Leu Asn Gly Lys Glu Tyr Lys Cys Lys
            335                 340                 345

Val Ser Asn Lys Ala Leu Pro Ala Pro Ile Glu Lys Thr Ile Ser
        350                 355                 360

Lys Ala Lys Gly Gln Pro Arg Glu Pro Gln Val Tyr Thr Leu Pro
    365                 370                 375

Pro Ser Arg Glu Glu Met Thr Lys Asn Gln Val Ser Leu Thr Cys
380                 385                 390

Leu Val Lys Gly Phe Tyr Pro Ser Asp Ile Ala Val Glu Trp Glu
                395                 400                 405

Ser Asn Gly Gln Pro Glu Asn Asn Tyr Lys Thr Thr Pro Pro Val
            410                 415                 420

Leu Asp Ser Asp Gly Ser Phe Phe Leu Tyr Ser Lys Leu Thr Val
        425                 430                 435

Asp Lys Ser Arg Trp Gln Gln Gly Asn Val Phe Ser Cys Ser Val
    440                 445                 450

Met His Glu Ala Leu His Asn His Tyr Thr Gln Lys Ser Leu Ser
455                 460                 465

Leu Ser Pro Gly Lys
                470

<210> SEQ ID NO 19
<211> LENGTH: 3000
<212> TYPE: DNA
<213> ORGANISM: Artificial sequence
<220> FEATURE:
<223> OTHER INFORMATION: Anti-TF vector

<400> SEQUENCE: 19
gaattcaact tctccatact ttggataagg aaatacagac atgaaaaatc         50
tcattgctga gttgttattt aagcttgccc aaaaagaaga agagtcgaat        100
gaactgtgtg cgcaggtaga agctttggag attatcgtca ctgcaatgct        150
```

```
tcgcaatatg gcgcaaaatg accaacagcg gttgattgat caggtagagg        200
gggcgctgta cgaggtaaag cccgatgcca gcattcctga cgacgatacg        250
gagctgctgc gcgattacgt aaagaagtta ttgaagcatc ctcgtcagta        300
aaaagttaat cttttcaaca gctgtcataa agttgtcacg gccgagactt        350
atagtcgctt tgttttttatt ttttaatgta tttgtaacta gtacgcaagt       400
tcacgtaaaa agggtatcta gaattatgaa aaagaatatc gcatttcttc        450
ttgcatctat gttcgttttt tctattgcta caaacgcgta cgctgatatc        500
cagatgaccc agtccccgag ctccctgtcc gcctctgtgg gcgatagggt        550
caccatcacc tgcagagcca gtcgcgacat caagagctat ctgaactggt       600
atcaacagaa accaggaaaa gctccgaaag tactgattta ctatgctact        650
agtctcgctg aaggagtccc ttctcgcttc tctggatccg gttctgggac        700
ggattacact ctgaccatca gcagtctgca gccagaagac ttcgcaactt        750
attactgtct tcagcacgga gagtctccat ggacatttgg acagggtacc        800
aaggtggaga tcaaacgaac tgtggctgca ccatctgtct tcatcttccc        850
gccatctgat gagcagttga atctggaac tgcttctgtt gtgtgcctgc         900
tgaataactt ctatcccaga gaggccaaag tacagtggaa ggtggataac        950
gccctccaat cgggtaactc ccaggagagt gtcacagagc aggacagcaa        1000
ggacagcacc tacagcctca gcagcaccct gacgctgagc aaagcagact        1050
acgagaaaca caaagtctac gcctgcgaag tcacccatca gggcctgagc        1100
tcgcccgtca caaagagctt caacagggga gagtgttaat taaatcctct        1150
acgccggacg catcgtggcg agctcggtac ccggggatct aggcctaacg        1200
ctcggttgcc gccgggcgtt ttttattgtt gccgacgcgc atctcgactg        1250
cacggtgcac caatgcttct ggcgtcaggc agccatcgga agctgtggta        1300
tggctgtgca ggtcgtaaat cactgcataa ttcgtgtcgc tcaaggcgca        1350
ctcccgttct ggataatgtt ttttgcgccg acatcataac ggttctggca        1400
aatattctga aatgagctgt tgacaattaa tcatcgaact agtttaatgt        1450
gtggaattgt gagcggataa caattaagct taggatctag aattatgaag        1500
aagaatattg cgttcctact gcctctatg tttgtctttt ctatagctac         1550
aaacgcgtac gctgaggttc agctggtgga gtctggcggt ggcctggtgc        1600
agccaggggg ctcactccgt ttgtcctgtg cagcttctgg cttcaatatt        1650
aaggagtact acatgcactg ggtccgtcag gccccgggta agggcctgga       1700
atgggttgga ttgattgatc cagagcaagg caacacgatc tatgacccga       1750
agttccagga ccgtgccact ataagcgctg acaattccaa aaacacagca       1800
tacctgcaga tgaacagcct gcgtgctgag gacactgccg tctattattg       1850
tgctcgagac acggccgctt acttcgacta ctggggtcaa ggaaccctgg       1900
tcaccgtctc ctcggcctcc accaagggcc catcggtctt ccccctggca       1950
ccctcctcca agagcacctc tgggggcaca gcggccctgg gctgcctggt       2000
caaggactac ttccccgaac cggtgacggt gtcgtggaac tcaggcgccc       2050
tgaccagcgg cgtgcacacc ttcccggctg tcctacagtc ctcaggactc       2100
```

-continued

| | |
|---|---|
| tactccctca gcagcgtggt gactgtgccc tctagcagct tgggcaccca | 2150 |
| gacctacatc tgcaacgtga atcacaagcc cagcaacacc aaggtggaca | 2200 |
| agaaagttga gcccaaatct tgtgacaaaa ctcacactag tccaccgtct | 2250 |
| ccagcacctg aactcctggg gggaccgtca gtcttcctct tccccccaaa | 2300 |
| acccaaggac accctcatga tctcccggac ccctgaggtc acatgcgtgg | 2350 |
| tggtggacgt gagccacgaa gaccctgagg tcaagttcaa ctggtacgtg | 2400 |
| gacggcgtgg aggtgcataa tgccaagaca aagccgcggg aggagcagta | 2450 |
| caacagcacg taccgtgtgg tcagcgtcct caccgtcctg caccaggact | 2500 |
| ggctgaatgg caaggagtac aagtgcaagg tctccaacaa agccctccca | 2550 |
| gcccccatcg agaaaaccat ctccaaagcc aagggcagc cccgagaacc | 2600 |
| acaggtgtac accctgcccc catcccggga agagatgacc aagaaccagg | 2650 |
| tcagcctgac ctgcctggtc aaaggcttct atcccagcga catcgccgtg | 2700 |
| gagtgggaga gcaatgggca gccggagaac aactacaaga ccacgcctcc | 2750 |
| cgtgctggac tccgacggct ccttcttcct ctacagcaag ctcaccgtgg | 2800 |
| acaagagcag gtggcagcag gggaacgtct tctcatgctc cgtgatgcat | 2850 |
| gaggctctgc acaaccacta cacgcagaag agcctctccc tgtctccggg | 2900 |
| taaataagca tgcgacggcc ctagagtccc taacgctcgg ttgccgccgg | 2950 |
| gcgttttta ttgttaactc atgtttgaca gcttatcatc gataagcttt | 3000 |

<210> SEQ ID NO 20
<211> LENGTH: 237
<212> TYPE: PRT
<213> ORGANISM: Artificial sequence
<220> FEATURE:
<223> OTHER INFORMATION: Anti-TF light chain

<400> SEQUENCE: 20

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ala Ser Arg Asp Ile Lys Ser Tyr Leu Asn Trp Tyr Gln
                50                  55                  60

Gln Lys Pro Gly Lys Ala Pro Lys Val Leu Ile Tyr Tyr Ala Thr
                65                  70                  75

Ser Leu Ala Glu Gly Val Pro Ser Arg Phe Ser Gly Ser Gly Ser
                80                  85                  90

Gly Thr Asp Tyr Thr Leu Thr Ile Ser Ser Leu Gln Pro Glu Asp
                95                  100                 105

Phe Ala Thr Tyr Tyr Cys Leu Gln His Gly Glu Ser Pro Trp Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

-continued

Glu Ala Lys Val Gln Trp Lys Val Asp Asn Ala Leu Gln Ser Gly
            170                 175                 180

Asn Ser Gln Glu Ser Val Thr Glu Gln Asp Ser Lys Asp Ser Thr
            185                 190                 195

Tyr Ser Leu Ser Ser Thr Leu Thr Leu Ser Lys Ala Asp Tyr Glu
            200                 205                 210

Lys His Lys Val Tyr Ala Cys Glu Val Thr His Gln Gly Leu Ser
            215                 220                 225

Ser Pro Val Thr Lys Ser Phe Asn Arg Gly Glu Cys
            230                 235

<210> SEQ ID NO 21
<211> LENGTH: 470
<212> TYPE: PRT
<213> ORGANISM: Artificial sequence
<220> FEATURE:
<223> OTHER INFORMATION: Anti-TF heavy chain

<400> SEQUENCE: 21

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
             20                  25                  30

Gly Gly Gly Leu Val Gln Pro Gly Gly Ser Leu Arg Leu Ser Cys
             35                  40                  45

Ala Ala Ser Gly Phe Asn Ile Lys Glu Tyr Tyr Met His Trp Val
             50                  55                  60

Arg Gln Ala Pro Gly Lys Gly Leu Glu Trp Val Gly Leu Ile Asp
             65                  70                  75

Pro Glu Gln Gly Asn Thr Ile Tyr Asp Pro Lys Phe Gln Asp Arg
             80                  85                  90

Ala Thr Ile Ser Ala Asp Asn Ser Lys Asn Thr Ala Tyr Leu Gln
             95                 100                 105

Met Asn Ser Leu Arg Ala Glu Asp Thr Ala Val Tyr Tyr Cys Ala
            110                 115                 120

Arg Asp Thr Ala Ala Tyr Phe Asp Tyr Trp Gly Gln Gly Thr Leu
            125                 130                 135

Val Thr Val Ser Ser Ala Ser Thr Lys Gly Pro Ser Val Phe Pro
            140                 145                 150

Leu Ala Pro Ser Ser Lys Ser Thr Ser Gly Gly Thr Ala Ala Leu
            155                 160                 165

Gly Cys Leu Val Lys Asp Tyr Phe Pro Glu Pro Val Thr Val Ser
            170                 175                 180

Trp Asn Ser Gly Ala Leu Thr Ser Gly Val His Thr Phe Pro Ala
            185                 190                 195

Val Leu Gln Ser Ser Gly Leu Tyr Ser Leu Ser Ser Val Val Thr
            200                 205                 210

Val Pro Ser Ser Ser Leu Gly Thr Gln Thr Tyr Ile Cys Asn Val
            215                 220                 225

Asn His Lys Pro Ser Asn Thr Lys Val Asp Lys Lys Val Glu Pro
            230                 235                 240

Lys Ser Cys Asp Lys Thr His Thr Ser Pro Pro Ser Pro Ala Pro
            245                 250                 255

Glu Leu Leu Gly Gly Pro Ser Val Phe Leu Phe Pro Pro Lys Pro
            260                 265                 270

-continued

```
Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg
        305                 310                 315

Glu Glu Gln Tyr Asn Ser Thr Tyr Arg Val Val Ser Val Leu Thr
        320                 325                 330

Val Leu His Gln Asp Trp Leu Asn Gly Lys Glu Tyr Lys Cys Lys
        335                 340                 345

Val Ser Asn Lys Ala Leu Pro Ala Pro Ile Glu Lys Thr Ile Ser
        350                 355                 360

Lys Ala Lys Gly Gln Pro Arg Glu Pro Gln Val Tyr Thr Leu Pro
        365                 370                 375

Pro Ser Arg Glu Glu Met Thr Lys Asn Gln Val Ser Leu Thr Cys
        380                 385                 390

Leu Val Lys Gly Phe Tyr Pro Ser Asp Ile Ala Val Glu Trp Glu
        395                 400                 405

Ser Asn Gly Gln Pro Glu Asn Asn Tyr Lys Thr Thr Pro Pro Val
        410                 415                 420

Leu Asp Ser Asp Gly Ser Phe Phe Leu Tyr Ser Lys Leu Thr Val
        425                 430                 435

Asp Lys Ser Arg Trp Gln Gln Gly Asn Val Phe Ser Cys Ser Val
        440                 445                 450

Met His Glu Ala Leu His Asn His Tyr Thr Gln Lys Ser Leu Ser
        455                 460                 465

Leu Ser Pro Gly Lys
            470
```

<210> SEQ ID NO 22
<211> LENGTH: 44
<212> TYPE: DNA
<213> ORGANISM: Artificial sequence
<220> FEATURE:
<223> OTHER INFORMATION: Synthetic

<400> SEQUENCE: 22
caaatcttgt gacaaaactc acactagtcc accgtctcca gcac            44

<210> SEQ ID NO 23
<211> LENGTH: 45
<212> TYPE: DNA
<213> ORGANISM: Artificial sequence
<220> FEATURE:
<223> OTHER INFORMATION: Synthetic

<400> SEQUENCE: 23
tcgggtttag aacactgttt tgagtgtgat caggtggcag aggtc            45

<210> SEQ ID NO 24
<211> LENGTH: 63
<212> TYPE: DNA
<213> ORGANISM: Artificial sequence
<220> FEATURE:
<223> OTHER INFORMATION: Synthetic

<400> SEQUENCE: 24
cccaccgtcg ccggcacctg aactcctggg gggaccgtca gtcttcctct            50
tccccccaaa acc            63

<210> SEQ ID NO 25
<211> LENGTH: 71
<212> TYPE: DNA
<213> ORGANISM: Artificial sequence
<220> FEATURE:
<223> OTHER INFORMATION: Synthetic

<400> SEQUENCE: 25
gtacgggtgg cagcggccgt ggacttgagg accccctgg cagtcagaag        50 gagaaggggg gttttgggtt c        71

<210> SEQ ID NO 26
<211> LENGTH: 63
<212> TYPE: DNA
<213> ORGANISM: Artificial sequence
<220> FEATURE:
<223> OTHER INFORMATION: Synthetic

<400> SEQUENCE: 26
cccaccgtcg ccggcacctg aactcctggg gggaccgtca gtcttcctct        50 tcccccaaa acc        63

<210> SEQ ID NO 27
<211> LENGTH: 71
<212> TYPE: DNA
<213> ORGANISM: Artificial sequence
<220> FEATURE:
<223> OTHER INFORMATION: Synthetic

<400> SEQUENCE: 27
gtacgggtgg cagcggccgt ggacttgagg accccctgg cagtcagaag        50 gagaaggggg gttttgggtt c        71

<210> SEQ ID NO 28
<211> LENGTH: 67
<212> TYPE: DNA
<213> ORGANISM: Artificial sequence
<220> FEATURE:
<223> OTHER INFORMATION: Synthetic

<400> SEQUENCE: 28
ctagtccacc gtgcccagca cctgaactcc tgggggacc gtcagtcttc        50 ctcttccccc caaaacc        67

<210> SEQ ID NO 29
<211> LENGTH: 67
<212> TYPE: DNA
<213> ORGANISM: Artificial sequence
<220> FEATURE:
<223> OTHER INFORMATION: Synthetic

<400> SEQUENCE: 29
aggtggcacg ggtcgtggac ttgaggaccc ccctggcagt cagaaggaga        50
aggggggttt tgggttc        67

<210> SEQ ID NO 30
<211> LENGTH: 67
<212> TYPE: DNA
<213> ORGANISM: Artificial sequence
<220> FEATURE:
<223> OTHER INFORMATION: Synthetic

<400> SEQUENCE: 30
ctagtccacc gtgcccagca cctgaactcc tgggggacc gtcagtcttc         50 ctcttccccc caaaacc                                            67

<210> SEQ ID NO 31
<211> LENGTH: 67
<212> TYPE: DNA
<213> ORGANISM: Artificial sequence
<220> FEATURE:
<223> OTHER INFORMATION: Synthetic

<400> SEQUENCE: 31
aggtggcacg ggtcgtggac ttgaggaccc ccctggcagt cagaaggaga         50
aggggggttt tgggttc                                            67

<210> SEQ ID NO 32
<211> LENGTH: 44
<212> TYPE: DNA
<213> ORGANISM: Artificial sequence
<220> FEATURE:
<223> OTHER INFORMATION: Synthetic

<400> SEQUENCE: 32
tagctacaaa cgcgtatgcc tcgaagttaa aagtgcctga actg              44

<210> SEQ ID NO 33
<211> LENGTH: 38
<212> TYPE: DNA
<213> ORGANISM: Artificial sequence
<220> FEATURE:
<223> OTHER INFORMATION: Synthetic

<400> SEQUENCE: 33
gctgaaatgg gccccacatg cacggaggtg ttgaaaga                     38

<210> SEQ ID NO 34
<211> LENGTH: 62
<212> TYPE: DNA
<213> ORGANISM: Artificial sequence
<220> FEATURE:
<223> OTHER INFORMATION: Synthetic

<400> SEQUENCE: 34
catttcaaca atcaacccct ctcctccatc caaggagtct cacaaatctc         50
cagctcctaa cc                                                 62

<210> SEQ ID NO 35
<211> LENGTH: 70
<212> TYPE: DNA
<213> ORGANISM: Artificial sequence
<220> FEATURE:
<223> OTHER INFORMATION: Synthetic

<400> SEQUENCE: 35
ccgggtaaag ttgttagttg gggagaggag gtaggttcct cagagtgttt         50
agaggtcgag gattggagct                                         70

<210> SEQ ID NO 36
<211> LENGTH: 35
<212> TYPE: DNA
<213> ORGANISM: Artificial sequence
<220> FEATURE:
<223> OTHER INFORMATION: Synthetic -continued

```
<400> SEQUENCE: 36
catactggta ccaggatcta gagggaagat ttatg                                35

<210> SEQ ID NO 37
<211> LENGTH: 28
<212> TYPE: DNA
<213> ORGANISM: Artificial sequence
<220> FEATURE:
<223> OTHER INFORMATION: Synthetic

<400> SEQUENCE: 37
ctggtgagta ctcaaccaag tcattctg                                        28
```